United States Patent
Johnson et al.

(10) Patent No.: US 12,223,021 B2
(45) Date of Patent: *Feb. 11, 2025

(54) SYSTEMS AND METHODS FOR CONTROLLING A DIGITAL ECOSYSTEM USING DIGITAL GENOMIC DATA SETS

(71) Applicant: Quantum Digital Solutions Corporation, Marina Del Rey, CA (US)

(72) Inventors: William C. Johnson, Marina Del Rey, CA (US); Gurgen Khachatryan, Marina Del Rey, CA (US); Karen Ispiryan, Santa Monica, CA (US)

(73) Assignee: Quantum Digital Solutions Corporation, Marina Del Rey, CA (US)

( * ) Notice: Subject to any disclaimer, the term of this patent is extended or adjusted under 35 U.S.C. 154(b) by 447 days.

This patent is subject to a terminal disclaimer.

(21) Appl. No.: 17/497,167

(22) Filed: Oct. 8, 2021

(65) Prior Publication Data

US 2022/0100835 A1    Mar. 31, 2022

Related U.S. Application Data

(63) Continuation-in-part of application No. PCT/US2021/016617, filed on Feb. 4, 2021.
(Continued)

(51) Int. Cl.
*H04L 29/06* (2006.01)
*G06F 8/30* (2018.01)
(Continued)

(52) U.S. Cl.
CPC .............. *G06F 21/32* (2013.01); *G06F 8/315* (2013.01); *G16B 50/00* (2019.02); *G16B 99/00* (2019.02);
(Continued)

(58) Field of Classification Search
CPC ......... G06F 21/32; G06F 8/315; G06F 21/602
See application file for complete search history.

(56) References Cited

U.S. PATENT DOCUMENTS

| 8,094,817 B2 | 1/2012 | Blom et al. |
| 8,633,797 B2 | 1/2014 | Farris et al. |

(Continued)

FOREIGN PATENT DOCUMENTS

| AU | 2019201785 A1 | 2/2020 |
| CN | 102025482 A | 4/2011 |

(Continued)

OTHER PUBLICATIONS

Huang, Zhicong, et al. "Genoguard: Protecting genomic data against brute-force attacks." 2015 IEEE Symposium on Security and Privacy. IEEE, 2015. (Year: 2015).*

(Continued)

*Primary Examiner* — Shawnchoy Rahman
(74) *Attorney, Agent, or Firm* — RMCK Law Group, PLC

(57) ABSTRACT

Techniques for performing genomic security-related control of a digital ecosystem are disclosed. In embodiments, the digital ecosystem includes an ecosystem VDAX that maintains a progenitor genomic data set corresponding to the digital ecosystem, generates a plurality of respective progeny genomic data sets based on the progenitor genomic data set, and allocates the progeny genomic data set to a respective progeny VDAX of a plurality of progeny VDAXs, wherein the progeny VDAX establishes unique non-recurring engagements with other progeny VDAXs in the digital ecosystem based on the respective progeny genomic data set allocated to the progeny VDAX without any further interaction from the ecosystem VDAX. The ecosystem VDAX also controls a genomic topology of the ecosystem by selectively updating one or more of the progeny genomic (Continued)

data sets to affect an ability of specific progeny VDAXs to engage with other VDAXs in the ecosystem.

30 Claims, 13 Drawing Sheets

Related U.S. Application Data

(60) Provisional application No. 63/145,860, filed on Feb. 4, 2021, provisional application No. 62/970,304, filed on Feb. 5, 2020.

(51) Int. Cl.
*G06F 21/32* (2013.01)
*G16B 50/00* (2019.01)
*G16B 99/00* (2019.01)
*G16Z 99/00* (2019.01)
*H03M 7/00* (2006.01)
*H04L 9/40* (2022.01)

(52) U.S. Cl.
CPC ............... *G16Z 99/00* (2019.02); *H03M 7/00* (2013.01); *H04L 63/0428* (2013.01); *H04L 63/205* (2013.01)

(56) References Cited

U.S. PATENT DOCUMENTS 8,832,808 B2 9/2014 Liu et al.
8,898,479 B2 11/2014 Shaw
8,903,090 B2 12/2014 Bikel et al.
9,043,596 B2 5/2015 Jung et al.
9,449,191 B2 9/2016 MacCarthy et al.
9,548,860 B2 1/2017 Zhang et al.
9,596,220 B2 3/2017 Hassan et al.
9,807,570 B1 10/2017 Lazarini et al.
9,922,320 B2 3/2018 Bonalle et al.
10,007,660 B2 6/2018 Sarikaya et al.
10,031,679 B2 7/2018 O'Hare et al.
10,131,280 B2 11/2018 Wind et al.
10,169,574 B2 1/2019 Nesher et al.
10,419,215 B2 9/2019 Hassan
10,469,260 B2 11/2019 Hassan
10,552,620 B2 2/2020 Desai et al.
10,601,596 B2 3/2020 Costa et al.
10,615,967 B2 4/2020 Basmov et al.
10,630,467 B1 4/2020 Gilbert et al.
10,652,743 B2 5/2020 Fitzgibbon
10,664,583 B2 5/2020 Proulx et al.
10,700,865 B1 6/2020 Hendrick et al.
10,708,046 B1 7/2020 Ashrafi
10,769,615 B2 9/2020 Li et al.
10,777,605 B2 9/2020 Freedman et al.
10,817,590 B1 10/2020 Daly et al.
10,826,877 B2 11/2020 Nayshtut et al.
10,832,072 B1 11/2020 Fraser
10,860,302 B2 12/2020 Nightingale et al.
10,862,870 B2 12/2020 Maier et al.
10,875,420 B2 12/2020 Grimm et al.
10,880,340 B2 12/2020 Harrison
10,891,849 B1 1/2021 Kumar et al.
10,903,541 B2 1/2021 Abdo et al.
10,903,868 B2 1/2021 Perthuis et al.
10,904,256 B2 1/2021 Brickell
10,910,087 B2 2/2021 Cho et al.
10,934,748 B2 3/2021 Harajli et al.
10,936,303 B2 3/2021 Bonar et al.
10,936,731 B2 3/2021 Linton et al.
10,944,559 B2 3/2021 Fitzgibbon et al.
10,951,578 B1 3/2021 Nainar et al.
10,951,609 B2 3/2021 Komperla et al.
10,956,609 B2 3/2021 Kochura et al.
10,956,828 B2 3/2021 Chow et al.
10,957,420 B2 3/2021 Agrawal et al.
10,972,452 B2 4/2021 Mathaiyan et al.
10,972,538 B2 4/2021 Chen et al.
10,977,372 B2 4/2021 Sood et al.
10,992,338 B1 4/2021 Priyantha et al.
11,000,213 B2 5/2021 Kamath et al.
11,005,810 B2 5/2021 Souhrada et al.
11,019,048 B2 5/2021 Callaghan
11,022,625 B2 6/2021 Tanaka
11,023,558 B1 6/2021 Kurien et al.
11,023,622 B2 6/2021 Rozas et al.
11,343,318 B2 5/2022 Lee et al.
11,424,009 B2 8/2022 Philippe et al.
2002/0029280 A1 3/2002 Holden et al.
2002/0078352 A1 6/2002 Angwin et al.
2003/0217165 A1 11/2003 Buch et al.
2005/0026117 A1 2/2005 Judson et al.
2009/0070281 A1 3/2009 Solomon
2010/0318800 A1 12/2010 Simon et al.
2011/0016318 A1 1/2011 Syngkon et al.
2012/0124387 A1 5/2012 Skocic
2013/0044876 A1 2/2013 Shaw et al.
2013/0166518 A1 * 6/2013 Mande .................. G16B 50/50
707/693
2013/0185806 A1 7/2013 Hatakeyama
2013/0254255 A1 9/2013 Nilsson et al.
2014/0298461 A1 10/2014 Hohndel et al.
2016/0024556 A1 1/2016 Zhang
2016/0085916 A1 3/2016 Smith
2017/0236520 A1 8/2017 Borgstrom et al.
2017/0242961 A1 8/2017 Shukla et al.
2017/0261518 A1 9/2017 Paczesny
2018/0046766 A1 2/2018 Deonarine et al.
2018/0068000 A1 3/2018 Messaoud et al.
2018/0201998 A1 7/2018 Xiang et al.
2019/0289038 A1 9/2019 Li et al.
2019/0318816 A1 10/2019 Witchey
2019/0394243 A1 12/2019 Wiig et al.
2020/0007345 A1 1/2020 Barry et al.
2020/0184489 A1 6/2020 Negi et al.
2020/0311816 A1 10/2020 Calvin
2021/0050995 A1 2/2021 Ragan et al.
2022/0103529 A1 3/2022 Johnson et al.

FOREIGN PATENT DOCUMENTS

CN 102075931 B 4/2013
CN 105046636 B 5/2017
CN 110971403 A 4/2020
CN 108847932 B 7/2020
CN 108599934 B 9/2020
CN 108134772 B 11/2020
CN 115702560 A * 2/2023 ............... H04L 9/30
DE 102019108328 A1 10/2020
WO WO-2015080987 A1 * 6/2015 ............ G06F 19/28
WO 2018007525 A2 1/2018
WO 2018096559 A1 5/2018
WO 2019107129 A1 6/2019
WO 2020209988 A2 10/2020
WO 2021013736 A1 1/2021
WO 2021158791 A1 8/2021

OTHER PUBLICATIONS

Briscoe, G. et al., "Digital Ecosystems: Ecosystem-Oriented Architectures," Dec. 2011, arXiv preprint arXiv:1112.0204v1, 39 pages.
Briscoe, G. et al., "Digital Ecosystems: Self-Organisation of Evolving Agent Populations," Oct. 2009, arXiv preprint arXiv:0803.2675v4, 5 pages.
Hadzic, M. et al., "Methodology Framework for the Design of Digital Ecosystems," IEEE International Conference on Systems, Man and Cybernetics, 2007, pp. 7-12.
Hedin, Y. et al., "Security in Multi-Agent Systems," Procedia Computer Science, vol. 60, 2015, pp. 1604-1612.
Lobo, L.M.R.J. et al., "Use of Genetic Algorithm in Network Security," International Journal of Computer Applications (0975-8887), vol. 53, No. 8, Sep. 2012, pp. 1-7.

(56) References Cited

OTHER PUBLICATIONS

PCT International Search Report and Written Opinion dated May 17, 2021 for International Application No. PCT/US2021/016617, 17 pages.
Shaw, H., "A Cryptographic System Based upon the Principles of Gene Expression," 2017 Cryptography 1(3), 21, www.mdpi.com/journal/cryptography, 18 pages.
Carlini, F. et al., "The Genesy Model for a Blockchain-Based Fair Ecosystem of Genomic Data," Frontiers in Blockchain, Technology and Code, vol. 3, Dec. 2020, 14 pages.
Heesch, M.V. et al., "Towards Quantum-Safe VPNs and Internet," IACR Cryptol. ePrint Arch., 2019, 1277, 8 pages.
PCT International Search Report and Written Opinion dated Apr. 22, 2022 for International Application No. PCT/US2022/015109, 17 pages.
Paganini, P., "DNA Contains Instructions for Biological and Computer Viruses," Aug. 2017, https://securityaffairs.co/wordpress/61940/hacking/dna-contains-instructions-biological-computer-viruses.html, 6 pages.
Sharma, D. et al., "Encoding Scheme For Data Storage And Retrieval On DNA Computers," IET Nanobiotechnology, E-First on Sep. 2, 2020, vol. 14, Iss. 7, pp. 635-641.
U.S. Appl. No. 17/668,897, filed Feb. 10, 2022, Johnson et al.
U.S. Appl. No. 17/668,929, filed Feb. 10, 2022, Johnson et al.
U.S. Appl. No. 17/668,965, filed Feb. 10, 2022, Johnson et al.
U.S. Appl. No. 17/668,989, filed Feb. 10, 2022, Johnson et al.
U.S. Appl. No. 17/669,021, filed Feb. 10, 2022, Johnson et al.
U.S. Appl. No. 17/497,205, filed Oct. 8, 2021, Johnson et al.
U.S. Appl. No. 17/497,241, filed Oct. 8, 2021, Johnson et al.
U.S. Appl. No. 17/497,315, filed Oct. 8, 2021, Johnson et al.
Extended European Search Report dated Jan. 26, 2024 for EP Application No. 21750703.7, 7 pages.

* cited by examiner

CYPHERGENICS (CG): TECHNOLOGY ENABLES COMPREHENSIVE POST QUANTUM SECURITY:

| | PKI : POST QUANTUM | QKD : POST QUANTUM | CYPHERGENICS : POST QUANTUM |
|---|---|---|---|
| SECURITY COHORT ID ATTRIBUTES | | | |
| Authentication : Facilitation | Trusted Third Party | Trusted Third Party | Digital-Cohort to Digital-Cohort |
| Non-Repudiation : Facilitation | Trusted Third Party | Trusted Third Party | Digital-Cohort to Digital-Cohort |
| Integrity : Facilitation | Message | Message | Digital Object by Digital Object |
| SECURITY TECHNOLOGY ATTRIBUTES | | | |
| Key Mgmt. : Basis | Under Development | Quantum Phenomena | Virtual Binary Language Script (VBLS) |
| Encryption : Basis | Under Development | Quantum Phenomena | Virtual Binary Language Script (VBLS) |
| Engagement : Scalability | One to Many | One to One | Many to Many |
| SECURITY APPLICATION ATTRIBUTES | | | |
| Domain | Network | Optical Communications Networks | Global Digital Ecosystems |
| Function | Data Transport | Data Transport | Security-Instance by Security-Instances |
| Engagement | Device to Device | Photon Detector to Photon Detector | Digital-Cohort to Digital-Cohort |
| Primary Application | Session Managed Engagement | Session Managed Engagement | Security Architecture Generation |
| SECURITY ENGAGEMENT ATTRIBUTES | | | |
| Session Coordination | Per Engagement | Per Engagement | Obsoleted by VBLS |
| Secret Key Generation | Per Engagement | Per Engagement | Obsoleted by VBLS |
| Secret Key Exchange | Per Engagement | Per Engagement | Obsoleted by VBLS |
| Secret Key Retention | Per Engagement | Per Engagement | Obsoleted by VBLS |

FIG. 3

SYSTEMS AND METHODS FOR CONTROLLING A DIGITAL ECOSYSTEM USING DIGITAL GENOMIC DATA SETS

CROSS-REFERENCE TO RELATED APPLICATIONS

This application is a bypass continuation-in-part of PCT International Application No. PCT/US2021/016617, filed Feb. 4, 2021, entitled "Information Theory Genomics-Enabled Hyper-Scalability," which claims priority to U.S. Provisional Patent Application Ser. No. 62/970,304, filed Feb. 5, 2020, entitled "Genomic-Based Security Platforms". This application claims priority to U.S. Provisional Patent Application Ser. No. 63/145,860, filed Feb. 4, 2021, entitled "Information Theory Genomics-Enabled Hyper-Scalability". All of the above applications are hereby incorporated by reference in their entirety.

FIELD

The present disclosure relates to Information Theory-facilitated security platforms and corresponding digital genomic constructions that exhibit controlled entropy yet are subject to digital modification and reconstruction by computationally complex functions and processes without loss of genomic integrity. These constructions enable formation of comprehensively secure hyper-scalable digital ecosystems, enclaves, and/or digital cohorts having mutual identity of interests, and application specific security architectures based on genomic network topologies that are interoperable with contemporary application and networks stacks.

BACKGROUND

The requirement to distinguish the Noble from the Nefarious has grown in urgency as the ARPAnet community of adjunct-nodes breached their perimeter into a world-wide-web comprised of virtual digital ecosystems supported by an interoperable Digital Monoculture. By the time the material consequences faced by this new machine-connected-world became apparent, first responder technologies (e.g., Firewalls, Analytics, Forensics, PM, Proxies, and Monitoring) were already relegated to network perimeter patrol and rapid recovery services.

Experts broadly agree cryptography offers the only provable machine-connected-world security solution. Quantum, Homomorphic, and Obfuscation-based cryptographic research have garnered huge investment but no more than hoped for impact. Nevertheless, the most essential but indomitably complex of all cryptographic disciplines—hyper-scalability—remains unattended. Efforts to update PM to post quantum status abound, even as its linear scalability perseveres.

Applicant has developed and has disclosed herein, Cyphergenics (CG) technologies, which comprehensively resolves the heretofore intractable hyper-scalability dilemma, descriptions of which are disclosed in this document. As will be discussed, Cyphergenics enables unlimited deployment of cryptographic-based digital ecosystem security for di minimis overhead and bandwidth, while fully preserving interoperability. Importantly, hyper-scalability directly facilitates functional homomorphic cryptography and functional indistinguishable obfuscation.

SUMMARY

The artificial bifurcation of attacks on cyber infrastructure and assaults on privacy has been and remains misguided, as both leverage the same digital ecosystem (machine-connected-world) and digital monoculture (everything-interoperable-with-everything). Security solutions remain pedestrian kluges, expert at postmortem forensics and anemic at interdiction despite brilliant adaptations and extensions of vintage security technologies and methods. The limited capability of these technologies to thwart subversion, espionage, interloping, piracy, and assaults on privacy (whether covert or clandestine surveillance enabled) is well documented. Increasingly larger digital attack surfaces and powerful new variants of weaponized malware and processor exploits, and ultimately quantum computer assisted Cryptanalysis and artificial intelligence-informed subversive algorithms portend new levels of catastrophe.

Noble engagement has facilitated heretofore unimaginable virtualization of products, services, and knowledge, and redefined efficiency and efficacy. From within the same network centric campus, Nefarious engagement foments catastrophic cyber-attacks (e.g., subversion, espionage, interloping, and piracy) and pervasive assaults-on-privacy (e.g., covert and clandestine mass surveillance, profiling, and assimilation). It is substantially the common-machine-language and inherent hyper-scalability essential to their network centric missions that they share, which renders the noble and nefarious effectively indistinguishable.

Applicant submits that the most critical network centric competency is not the digital ecosystem comprised of various digital cohorts (e.g., networks, grids, clouds, systems, devices, appliances, sensors, IoT, applications, files, and data) nor its interoperable Digital Monoculture. It is the common-machine-language and hyper-scalability they share in order to scale their ubiquitous on-demand engagement (e.g., connection, communication, collaboration, and coordination) that accounts for hundreds of billions of unattended security instances: a huge permutation of billions of cohorts by millions of points-of-control by hundreds of billions of security instances per day.

It remains impractical to rebuild the digital ecosystem and Digital Monoculture, as well as interminably disruptive and financially imprudent. A technology capable of changing the common-machine-language based on computationally quantum-proof cryptography would offer highly effective security while eviscerating hyper-scalability essential to Digital Monoculture interoperability.

Cyphergenics (CG), a wholly new technology based on computationally complex genomic constructions, liberates modern cryptography from its intractably bounded but powerful computationally complex foundation. In embodiments, CG enables virtual unboundedness by generating information theory-constructed genomic constructions exhibiting computational complexity which can be directly regulated as are bio-chemical enabled constructions. Importantly, CG digital rendering preserves bio-chemical unbounded properties while vastly expanding the range of their inherent differences and correlation. CG preserves the ability of genomic constructions based on different Digital-DNA to be strategically regulated absent compromise of computational integrity. FIG. 1 illustrates attributes of Cyphergenics-based digital ecosystems in relation to related attributes of organic ecosystems and modern digital ecosystems, according to some embodiments of the present disclosure.

In embodiments, unique genomic and cryptographic properties amalgamated by information theory principles enable Cyphergenics-based technology to achieve highly functional hyper-scalability exhibiting unbounded differences (affiliation) and correlation (authentication). These properties in turn give rise to Virtual Affiliation, Virtual Authentication, Virtual Agility, Virtual Organic Engagement, and Virtual Trusted Execution Domains—powerful attributes whose applications far exceed security.

In embodiments, Cyphergenics enables hyper-scalability of specific digital ecosystems, enclaves, and cohorts, having mutual identity of interests (Digital-DNA related and regulated), which form the active basis of their engagement. These domain resident ecosystems, enclaves, and cohorts engage on the basis of hyper-scalable digital data objects and digital coder objects exhibiting unique, non-recurring, and computationally quantum-proof attributes reflecting their mutual identity of interest called Virtual Binary Language Script (VBLS) they share with impunity to nefarious intent.

While the Cyphergenics (CG) technology may be supported by a wide range of digital capable platforms and component configurations, some embodiments of the present disclosure are configured to ensure the orderly prosecution of critical computationally complex genomic construction and Digital-DNA regulation functions and processes. In embodiments, Cyphergenics Ecosystem security platform (CG-ESP) may be comprised of modules which control specific computational and genomic construction, and digital DNA regulation functions. In embodiments, this adaptability is critical given Cyphergenics functions may be rendered by ciphers, without any ciphers, or in combination.

In embodiments, Cyphergenics supports applications beyond network centric interests, such that its modules-based rendering may serve multiple purposes. For example, they allow individual genomic information theory enabled construction and regulation processes and functions to be re-imagined and incrementally improved or modified without compromising hyper-scalability, and they allow for computational and functional innovation among Cyphergenics application ready attributes.

Security applications with few exceptions must endure the network configurations over which they transact and the vulnerabilities these networks often induce, e.g., NAT circumvention of IP-SEC security to extend exhausted IP-IV addresses. Cyphergenics VBLS attribute enables powerful new, security application-centric genomic network topologies to operate simultaneously, interoperably, and on-demand over existing network configurations. Cyphergenics enables many security centric genomic network topologies to include Directed Architectures, Spontaneous Architectures, Ephemeral Architectures, Interledger Architecture, and others. FIG. 2 demonstrates an example of this adaptability and shows a Cyphergenics-enabled security stack that may be applied coextensively at various layers of commonly known application and network stacks and examples of Cyphergenics-facilitated genomic architectures of digital ecosystems that may result from such application, according to some embodiments of the present disclosure.

In embodiments, Cyphergenics's range of information theory-enabled genomic construction allows for digital-cohort to be spawned as progeny of a specific enterprise and/or enclave prior to their own conception. In embodiments, Cyphergenics-enabled digital ecosystems may be rendered gnomically flat or hierarchical, with or without orientation to order, e.g., time. In embodiments, a Cyphergenics cohort can serve the role of Cambrian Genome carrier—preserving instructions for subsequent construction of its own species-specific Ecosystem, Enclaves, and Progeny (reverse procreation), for which it must still undergo genomic regulation to achieve correlation and differentiation.

The differences between Cyphergenics—which implementation and practice are explained in the details of this patent—and the search for postmodern (quantum proof) cryptography technology is summarized below, examples of which may be observed in FIG. 3. Even if successful, contemporary efforts to defeat quantum computer enhanced cryptanalysis only stand to preserve the status quo, no matter that network centric security challenges continue to markedly and materially escalate.

In embodiments, Cyphergenics-based technology may displace the underlying approaches as opposed to developing variants of the existing technology and its inherent limitations.

The present disclosure relates to different implementations of Cyphergenics-based technologies and security platforms that are applied in myriad digital ecosystems having different and wide-ranging mutual identities of interest and topologies. In embodiments of the present disclosure, instances of Cyphergenics-based security platforms may be configured for the different types of digital ecosystems with different architectures to optimize different aspects of the respective ecosystem which they serve.

According to some embodiments of the present disclosure, an ecosystem security platform is disclosed. The ecosystem security platform is executed by a processing system of a VDAX. The ecosystem security platform includes a root DNA module, a link module, a sequence mapping module, and a binary transformation module. The root DNA module is configured to manage a digitally generated genomic data set assigned to the VDAX. The genomic data set is unique to the VDAX and includes a genomic eligibility object, a genomic correlation object, and a genomic differentiation object. The root DNA module is configured to modify the genomic data set using one or more computationally complex functions. The link module is configured to receive a link from a second VDAX. The link contains encoded genomic regulation instructions. The link module is configured to decode the link based on the genomic eligibility object and a modified genomic correlation object to obtain decoded genomic regulation instructions. The modified genomic correlation object is modified from the genomic correlation object by the root DNA module. The sequence mapping module is configured to obtain a sequence from a digital object that is to be provided to the second VDAX. The sequence is extracted from a first portion of the digital object. The sequence mapping module is configured to map the sequence into a modified genomic differentiation object to obtain a genomic engagement factor. The modified genomic differentiation object is modified from the genomic differentiation object by the root DNA module based on the decoded genomic regulation instructions. The binary transformation module is configured to encode a second portion of the digital object based on the genomic engagement factor to obtain an encoded digital object. The binary transformation module is configured to generate a virtual binary language script (VBLS) object that includes the encoded digital object and the first portion of the digital object. The VBLS object is provided to the second VDAX as part of a series of VBLS objects.

In some embodiments, the digital object may be part of a series of digital objects that are each encoded into a respective VBLS object of the series of respective VBLS objects. Each digital object may be encoded using a different respective genomic engagement factor. In some embodiments, the sequence mapping module may obtain a respective sequence from each respective digital object and may map the respective sequence into the modified genomic differentiation object to obtain the respective genomic engagement factor that may be used to encode the respective digital object. In some embodiments, the series of VBLS objects may be a non-recurring language that is unique to the VDAX and the second VDAX. In some embodiments, the sequence may be a public sequence that is defined in the first portion of the digital object in accordance with a publicly known protocol and format. In some embodiments, the sequence may be a private sequence that may be defined in the first portion of the digital object in accordance with a proprietary protocol and format that may not be publicly available.

In some embodiments, the binary transformation module may include a disambiguation module that encodes the second portion of the digital object based on the genomic engagement factor by determining a disjunctive union of the second portion and the genomic engagement factor using an XOR operation. In some embodiments, the binary transformation module may include an encryption module that encodes the second portion of the digital object based on the genomic engagement factor by encrypting the second portion of the digital object using an encryption function and the genomic engagement factor.

In some embodiments, the link module may decode the link from the second VDAX as part of a link exchange process with the second VDAX. The link exchange process may be a one-time process. In some embodiments, the link exchange process may include authenticating an ecosystem member associated with the second VDAX based on the genomic eligibility object of the VDAX. In some embodiments, the link module may be further configured to spawn a second link that contains second encoded genomic regulation instructions. The second link may be provided to the second VDAX as part of the link exchange process. In some embodiments, the link exchange process may be a di-symmetric process such that the second link may be spawned independent of the link received from the second VDAX. In some embodiments, in spawning the second link, the link module may be further configured to determine second genomic regulation instructions. The link module may be further configured to encode the second genomic regulation instructions using a link genomic engagement factor to obtain the second encoded genomic regulation instructions. The link genomic engagement factor may be determined by the sequence mapping module based on a link mapping sequence and a second modified genomic correlation object that may be modified from the genomic correlation object by the root DNA module. The link module may be further configured to generate genomic engagement cargo that contains the link mapping sequence, the second encoded genomic regulation instructions, and encoded link decoding information. The link mapping sequence may not be obfuscated in the genomic engagement cargo and the second link may contain the genomic engagement cargo. The link module may be further configured to provide the second link to the second VDAX. The second VDAX may decode the second encoded genomic regulation instructions based on the link mapping sequence, the encoded link decoding information, and a second genomic data set that is assigned to the second VDAX. In some embodiments, the link mapping sequence may be left unencoded in the genomic engagement cargo. In some embodiments, the binary transformation module may be further configured to receive a second VBLS object from the second VDAX. The second VBLS object may contain a second encoded digital object and unencoded metadata. The binary transformation module may be further configured to decode the second digital object based on a second genomic engagement factor to obtain an unencoded second digital object. The second genomic engagement factor may be determined by the sequence mapping module based on a second sequence and a second modified genomic differentiation object that may be derived from the genomic differentiation object of the genomic data set by the root DNA module based on the second genomic regulation instructions.

In some embodiments, the link module may be configured to perform a link exchange process across a set of interoperable digital communications media. In some embodiments, the link module may be configured to perform a link exchange process across a set of interoperable digital networks. In some embodiments, the link module may be configured to perform a link exchange process across a set of interoperable digital devices. In some embodiments, the link module may be configured to perform a link exchange that may be executed asynchronously with respect to the second VDAX. In some embodiments, the link module may be configured to perform a link exchange process in a symmetric manner such that the VDAX may not provide a second link to the second VDAX. In some embodiments, the link module may be further configured to confirm eligibility correlation with respect to the second VDAX based on the genomic eligibility correlation object of the VDAX. In some embodiments, the link module may be further configured to confirm link-exchange correlation with respect to the second VDAX based on the link received from the second VDAX and the genomic correlation object of the VDAX. In some embodiments, the link module may be configured to prosecute a secure exchange of link information using a set of computationally complex functions. The set of computationally complex functions may be one of cipher-based functions, cipherless functions, or hybrid functions that may include at least one cipher-based function and at least one cipherless function. In some embodiments, the link module may be configured to execute a set of processes to securely exchange link information with the second VDAX to enable a di-symmetric engagement. The exchange of link information may exhibit a same level entropy as the di-symmetric engagement. In some embodiments, the link module may include a static link module that may be configured to spawn and decode static links. The static link module may generate static links in accordance with rules and processes prescribed by a highest-class ecosystem VDAX in the digital ecosystem. In some embodiments, the link module may include a dynamic link module that may be configured to spawn and decode dynamic links. The link received from the second VDAX may be a dynamic link that further includes an instruction set that, when executed by the VDAX, may override a respective configuration of at least one of the root DNA module, the sequence mapping module, or the binary transformation module. The modified configurations may be executed only when generating VBLS that may be provided to the second VDAX.

In some embodiments, the sequence mapping module may be configured to select public sequences from respective first portions of respective digital objects that may be formatted in accordance with a publicly available protocol. In some embodiments, in mapping the sequence into the modified genomic differentiation object, the sequence mapping module may be configured to processes the sequence to derive an intermediate value. The sequence mapping module may be configured to generate the genomic engagement factor based on the intermediate value and the modified genomic differentiation object using a set of information theory-facilitated computationally complex functions. In example embodiments, the set of information theory-facilitated computationally complex functions may be one of cipher-based functions, cipherless functions, or hybrid functions that include at least one cipher-based function and at least one cipherless function. In example embodiments, the genomic engagement factor may be a binary vector exhibiting specific entropy. The specific entropy of the genomic engagement factor may be greater than or equal to an inherent entropy of the sequence. In example embodiments, the sequence mapping module may be configured to select sequences from respective first portions of respective digital objects that may be formatted in accordance with a proprietary protocol.

In some embodiments, the root DNA module may include a CNA module that may formulate and construct the genomic eligibility object. The CNA module may be configured to employ information-theory-facilitated genomic processes to establish a specific relationship with other VDAXs in a respective digital ecosystem. In some embodiments, the link module may use the genomic eligibility object to confirm genomic engagement integrity with the second VDAX. In some embodiments, the genomic eligibility object may be a CNA object that exhibits specific entropy. The CNA object may enable difference and correlation-based genomic processes. The CNA object may be an N-dimensional binary vector that exhibits the specific entropy. The specific entropy of the CNA object may be configurable by a community owner. In some embodiments, the CNA module may be configured to generate a set of respective CNA objects based on the PNA object of the VDAX. The set of respective CNA objects may be respectively allocated to a set of respective progeny VDAXs and each CNA object may exhibit specific entropy that is equal to the entropy of the CNA object of the VDAX. In some embodiments, the CNA module may be configured to prosecute eligibility correlation with respect to another VDAX based on the CNA object and engagement information provided by the other VDAX using a set of information theory-facilitated computationally complex functions. The set of information theory-facilitated computationally complex functions may be one of cipher-based functions, cipherless functions, or hybrid functions that include at least one cipher-based function and at least one cipherless function. In some embodiments, the CNA module may be configured to establish specific relationships between other VDAXs in a digital ecosystem to which the VDAX belongs based in part on the CNA object of the VDAX.

In some embodiments, the root DNA module may include a PNA module that formulates and constructs the genomic eligibility object. The PNA module may be configured to employ information theory-facilitated genomic processes to establish a specific relationship with other VDAXs in a respective digital ecosystem. In some embodiments, the link module may use the genomic eligibility object to confirm genomic engagement eligibility with the second VDAX. The genomic eligibility object may be a PNA object that exhibits specific entropy. The PNA object may enable difference and correlation-based genomic processes. In some embodiments, the PNA object may include a first N-dimensional binary vector and a second N-dimensional binary vector that exhibit the specific entropy. The first N-dimensional vector may consist of M randomly chosen binary primitive polynomials of degree T such that M×T is equal to N, and the second N-dimensional vector is determined based on the first N-dimensional binary vector. In some embodiments, the specific entropy of the PNA object may be configurable by a community owner. In some embodiments, the PNA module may be configured to generate a set of respective PNA objects based on the PNA object of the VDAX. The set of respective PNA objects may be respectively allocated to a set of respective progeny VDAXs and each PNA object may exhibit specific entropy that is equal to the entropy of the PNA object of the VDAX. In some embodiments, the PNA module may be configured to prosecute eligibility correlation with respect to another VDAX based on the PNA object and engagement information provided by the other VDAX using a set of information-theory based computationally complex functions. The set of information theory-facilitated computationally complex functions may be one of cipher-based functions, cipherless functions, and hybrid functions that include at least one cipher-based function and at least one cipherless function. In some embodiments, the PNA module may be configured to establish specific relationships between other VDAXs in a digital ecosystem to which the VDAX belongs based in part on the PNA object of the VDAX.

In some embodiments, the root DNA module may include an LNA module that formulates and constructs the genomic correlation object. The LNA module may be configured to employ information theory-facilitated genomic processes to establish a specific relationship with other VDAXs in a respective digital ecosystem. In some embodiments, the link module may use the genomic eligibility object to confirm link exchange correlation with the second VDAX based on the link. In some embodiments, the genomic eligibility object may be an LNA object that exhibits specific entropy. The LNA object may enable difference and correlation-based genomic processes that may be performed during link exchange. The LNA object may be sufficiently correlated with a second LNA object of the second VDAX. In some embodiments, the specific entropy of the LNA object may be configurable by a community owner. In some embodiments, the LNA object may be an N-dimensional binary vector that exhibits the specific entropy. In some embodiments, the LNA module may be configured to prosecute link eligibility correlation with respect to another VDAX based on the LNA object and genomic engagement cargo provided in a respective link provided by the other VDAX using a set of information-theory based computationally complex functions. In some embodiments, the set of information theory-facilitated computationally complex functions may be one of cipher-based functions, cipherless functions, and hybrid functions that include at least one cipher-based function and at least one cipherless function. In some embodiments, the LNA module may be configured to establish specific relationships between other VDAXs in a digital ecosystem to which the VDAX belongs based in part on the LNA object of the VDAX. In some embodiments, the LNA module may be configured to generate a set of respective LNA objects based on the LNA object of the VDAX. The set of respective LNA objects may be respectively allocated to a set of respective progeny VDAXs. Each LNA object may be exhibit specific entropy that is equal to the entropy of the LNA object of the VDAX. In some embodiments, the LNA module may be configured to modify the genomic correlation object based on a set of specific set of instructions using a set of information theory-facilitated computationally complex functions. The set of information theory-facilitated computationally complex functions may be one of cipher-based functions, cipherless functions and hybrid functions that include at least one cipher-based function and at least one cipherless function. In some embodiments, the LNA module may modify the genomic correlation object based on the set of instructions received from a progenitor VDAX. The modification to the genomic correlation object may be used to establish future engagements with respect to a digital ecosystem to which the VDAX belongs while previously established engagements may not be affected. In some embodiments, the LNA module may modify the genomic correlation object based on the set of instructions received from the second VDAX in the link to obtain the modified genomic correlation object. The modified genomic correlation object may be used to determine a link genomic engagement factor that may be used to decode the encoded GRI.

In some embodiments, the root DNA module may include an XNA module that performs genomic processes involving the genomic correlation object, including at least one of generation of new genomic correlation objects and modification of the genomic correlation object of the VDAX. In some embodiments, the XNA module may be configured to employ information theory-facilitated genomic processes to modify the genomic differentiation object of the VDAX in an identical manner as the second VDAX in accordance with the genomic regulation instructions decoded from the link obtained from the second VDAX. In some embodiments, the genomic eligibility object may be an XNA object that exhibits specific entropy. In some embodiments, the XNA object may be sufficiently correlated with a second XNA object of the second VDAX. In some embodiments, the specific entropy of the XNA object may be configurable by a community owner. In some embodiments, the XNA object may be an N-dimensional binary vector that exhibits the specific entropy. In some embodiments, the XNA object may be used to establish future differentiation with other VDAX in possession of sufficiently correlated XNA objects. In some embodiments, the XNA module may be configured to generate a set of respective XNA objects based on the XNA object of the VDAX. The set of respective XNA objects may be respectively allocated to a set of respective progeny VDAXs. Each XNA object may exhibit specific entropy that is equal to the entropy of the XNA object of the VDAX. In some embodiments, the XNA module may be configured to modify the XNA based on a set of specific instructions using a set of information theory-facilitated computationally complex functions. In some embodiments, the XNA module may update the XNA based on the set of instructions received from a progenitor VDAX, such that the updated XNA may be used to establish future differentiation with respect to other VDAXs in a digital ecosystem to which the VDAX belongs. In some embodiments, the second VDAX may be unable to establish future differentiation with the VDAX unless the second VDAX is in possession of sufficiently correlated persistently updated XNA. In some embodiments, the set of information theory-facilitated computationally complex functions may be one of cipher-based functions, cipherless functions and hybrid functions that include at least one cipher-based function and at least one cipherless function.

In some embodiments, the ecosystem security platform may further include an authentication module that prosecutes secure genomic-based engagement correlation with respect to the second VDAX in accordance with information theory-facilitated computationally complex functions. The information theory-facilitated computationally complex functions may be one of cipher-based functions, cipherless functions, and hybrid functions that may include at least one cipher-based function and at least one cipherless function. In some embodiments, the ecosystem security platform may further include a master integrity controller that may include a genomic process controller, an authorization module, and an engagement instances module. The genomic process controller may have a master controller genomic data set assigned thereto.

In some embodiments, the genomic process controller may be configured to engage with one or more platform modules to authenticate and confirm integrity of the one or more platform modules. In some embodiments, the genomic process controller may confirm the integrity and authenticate the one or more platform modules based on the master controller genomic data set and a set of computationally complex functions. In some embodiments, the genomic process controller may confirm the integrity and authenticate the one or more platform modules without determining any processes or functions performed by the one or more platform modules. In some embodiments, the genomic process controller may be further configured to confirm integrity and authenticate any underlying operational processes and functions that connect the one or more platform modules using the set of computationally complex functions. In some embodiments, the genomic process controller may be further configured to confirm, disqualify, or initiate modification of the one or more platform modules and the underlying operational processes and functions.

In some embodiments, the authorization module may be configured to confirm or deny an operational configuration of another VDAX in a digital ecosystem based on the genomic controller genomic data and a set of information theory-facilitated computationally complex functions. In response to determining to deny the operational configuration of the other VDAX, the authorization module may disqualify or initiate modification of the operational configuration of the other VDAX.

In some embodiments, the engagement instances module may be configured to track security instances in a digital ecosystem of the VDAX in accordance with a set of one or more engagement tracking policies that define one or more definitions of a security instance. In some embodiments, the engagement instances module may be further configured to determine a number of security instances in the digital ecosystem of the VDAX in accordance with a set of one or more engagement accounting policies that respectively define a manner by which security instances are counted. In some embodiments, the engagement instances modules may be further configured to determine a report of the number of security instances in the digital ecosystem to another VDAX in accordance with a set of one or more engagement reporting policies that respectively define a manner by which the security instances are reported, to which VDAXs to report the security instances and how often to report the security instances.

In some of the embodiments, the VDAX is a member of a digital ecosystem. In some of these embodiments, the digital ecosystem is a cloud services system. In some of these embodiments, the digital ecosystem is an enterprise information technology system. In some of these embodiments, the digital ecosystem is a computing device and the progeny VDAXs respectively correspond to hardware components and digital components of the computing device. In some of these embodiments, the digital ecosystem is a classified computing infrastructure. In some embodiments, the digital ecosystem is a traffic grid. In some embodiments, the digital ecosystem is a home network.

According to some embodiments of the present disclosure, a system for performing genomic security-related control of a digital ecosystem is disclosed. The system includes an ecosystem VDAX that is executed by a processing system associated with an owner of the digital ecosystem. The ecosystem VAX is configured with an ecosystem instance of an ecosystem security platform, wherein the ecosystem VDAX is configured to maintain a progenitor genomic data set corresponding to the digital ecosystem that includes one or more different digitally generated progenitor genomic data objects, wherein each progenitor genomic data object exhibits a respective specific entropy. The ecosystem VAX is further configured to generate a plurality of respective progeny genomic data sets based on the progenitor genomic data set, wherein each respective progeny genomic data set includes one or more different progeny genomic data objects that were respectively derived from the one or more digitally generated progenitor genomic data objects and exhibit the respective specific entropy of the progenitor genomic data object from which it was derived. In these embodiments, the ecosystem VAX is configured to, for each respective progeny genomic data set, allocate the progeny genomic data set to a respective progeny VDAX of a plurality of progeny VDAXs, wherein the progeny VDAX establishes unique non-recurring engagements with other progeny VDAXs in the digital community based on the respective progeny genomic data set allocated to the progeny VDAX without any further interaction from the ecosystem VDAX. The ecosystem VDAX is further configured to control a genomic topology of the digital ecosystem by selectively updating one or more of the progeny genomic data sets to affect an ability of specific progeny VDAXs to engage with other VDAXs in the digital ecosystem.

In some of the embodiments, the progenitor genomic data set includes a progenitor genomic differentiation object and each progeny genomic data set includes a respective progeny genomic differentiation object. In some of these embodiments, a pair of progeny VDAXs from the plurality of progeny VDAXs can exchange virtual binary language script (VBLS) only if the respective progeny genomic differentiation objects of the pair of progeny VDAXs are sufficiently correlated.

In some of these embodiments, the pair of progeny VDAXs are prevented from future exchange of VBLS when a first progeny genomic differentiation object of a first progeny VDAX of the pair of progeny VDAXs is updated and a second progeny genomic differentiation object of a second progeny VDAX of the pair of progeny VDAXs is not updated.

In some embodiments, the progenitor genomic differentiation and the respective progeny genomic differentiation objects are XNA objects. In some of the embodiments, the digital ecosystem is at least one of a static ecosystem, wherein the ecosystem platform is configured in accordance with a directed architecture; an interactive ecosystem, wherein the ecosystem platform is configured in accordance with a free form architecture; or a dynamic ecosystem, wherein the ecosystem platform is configured in accordance with a dynamic-state spontaneous architecture. In some of these embodiments, a set of one or more enclave VDAXs, wherein each enclave VDAX corresponds to a respective digital enclave of the digital ecosystem and is allocated a respective enclave-specific XNA object with which the enclave VDAX controls an enclave genomic topology of the respective enclave. In some of these embodiments, each respective digital enclave includes one or more progeny VDAXs that respectively represent one or more respective cohorts that are admitted to the digital enclave, wherein each respective progeny VDAX that is included in the respective digital enclave is allocated a progeny enclave-specific XNA object that is derived from the enclave-specific XNA object of the enclave VDAX and is sufficiently correlated with respective progeny enclave XNA objects of other progeny VDAXs that are included in the digital enclave. In some of these embodiments, a respective enclave VDAX controls membership to the corresponding respective digital enclave by allocating enclave-specific XNA objects to the cohorts of the digital enclave.

In some embodiments, each enclave VDAX is further allocated a respective enclave genomic correlation object that is derived from a progenitor correlation object of the progenitor genomic data set. In some of these embodiments, each progeny VDAX in a digital enclave is allocated a respective progeny enclave-specific genomic correlation object that is derived from the enclave from the respective enclave genomic correlation object of the enclave VDAX of the digital enclave. In some of these embodiments, each progeny VDAX is allocated the respective enclave-specific genomic correlation object directly from the enclave VDAX of the digital enclave. In some embodiments, each progeny VDAX is allocated the respective enclave-specific genomic correlation object directly from the ecosystem VDAX.

In some embodiments, each progeny VDAXs uses its respective progeny enclave-specific genomic correlation object to spawn links that respectively establish unique non-recurring engagements with other progeny VDAXs that are formed with respect to the respective digital enclave. In some embodiments, each spawned link by the progeny VDAX provides unique genomic regulation instructions that define a manner by which a link hosting progeny VDAX modifies its enclave-specific XNA object to generate non-recurring VBLS that only the progeny VDAX can decode. In some embodiments, each progeny VDAXs uses its respective progeny enclave-specific genomic correlation object to host links provided by other progeny VDAXs in the digital ecosystem, wherein the other progeny VDAXs provide the links to the progeny VDAX to establish unique non-recurring engagements with the progeny VDAX with respect to the respective digital enclave.

In some of these embodiments, each hosted link by the progeny VDAX provides unique genomic regulation instructions that define a manner by which the progeny VDAX modifies its enclave-specific genomic differentiation object to generate non-recurring VBLS that only the other progeny VDAX that provided the link can decode.

In some of the embodiments, the enclave VDAX controls the genomic network topology by selectively updating progeny enclave-specific genomic data objects of a subset of progeny VDAXs that participate in the digital enclave. In some of the embodiments, the enclave VDAX controls the genomic network topology of the digital enclave without requiring modification to a physical network topology of the digital enclave. In some embodiments, wherein the digital ecosystem includes multiple genomic topologies that overlay one or more physical network topologies, wherein the multiple genomic topologies exist simultaneously and interoperably. In some embodiments, the ecosystem VDAX constructs and controls a genomic network topology that supports applications having dynamic state attributes.

In some embodiments, the system further comprises a set of one or more enclave VDAXs, wherein each enclave VDAX corresponds to a respective digital enclave of the digital ecosystem and is allocated a respective enclave-specific genomic data set with which the enclave VDAX controls portions of the genomic network topology that are responsible for ecosystem-designated functions and processes of the digital ecosystem.

In some of these embodiments, the system further includes a set of cohort VDAXs that participate in the digital ecosystem, wherein the set of cohort VDAXs include one or more cohorts that respectively control respective subportions of the genomic network topology that are responsible for specific ecosystem-designated and/or enclave-designated functions and processes. In some of these embodiments, interactions by the set of cohort VDAXs are controlled by respective cohort genomic data sets allocated to respective cohort VDAXs of the set of cohort VDAXs.

In some embodiments, the set of progeny VDAXs include the set of cohort VDAXs.

In some of these embodiments, the cohort genomic data set of each cohort of the set of cohort VDAXs include: one or more cohort genomic eligibility objects that include one or both of one unique CNA object and one unique PNA object; one or more cohort genomic correlation objects that include one or more LNA objects, wherein each LNA object corresponds to a respective enclave to which the cohort VDAX is admitted; and one or more cohort genomic differentiation objects that include one or more XNA objects, wherein each XNA object corresponds to a respective enclave to which the cohort VDAX is admitted.

In some of these embodiments, the digital ecosystem is a dynamic ecosystem and the ecosystem security platform is configured in accordance with a spontaneous architecture that retains its operational integrity regardless of a frequency in which one or more metric states of the dynamic ecosystem is updated.

In some of these embodiments, the ecosystem VDAX and the progeny VDAXs collectively control the genomic network topology in response to specific dynamic metric states. In some embodiments, the genomic digital network topology is constructed to realize controlled levels of interoperability. In some of the embodiments, the supports multiple genomic network topologies overlaid on a physical network topology that exist simultaneously.

In some embodiments, the progenitor genomic differentiation and the respective progeny genomic differentiation objects are ZNA objects. In some of these embodiments, the digital ecosystem is a virtual trusted execution domain implemented with respect to a device having one or more processors and the progeny VDAXs correspond to respective components of the device including at least one of one or more hardware components and one or more digital components, wherein the one or more hardware components include one or more of a system on chip (SoC), a core, or a disk and the one or more digital components include one or more of an operating system, a process, a thread, a library, or an application programming interface (API). In some of these embodiments, the progeny VDAXs from the plurality of progeny VDAXs are configured to perform component binary isolation (CBI) with respect to the virtual trusted execution domain.

In some embodiments, the system further includes the set of progeny VDAXs. In these embodiments, each progeny VDAX is configured with a respective progeny instance of the ecosystem security platform, such that each progeny instance of the ecosystem security platform is configured with a respective set of functionally congruent modules that are respectively configured to execute one or more information theory-facilitated computationally complex functions.

In some of these embodiments, the set of modules of each progeny instance of the ecosystem security platform includes a DNA module that is configured to manage the genomic data set of the progeny VDAX and perform a set of genomic processes based on the genomic data set. In some of the embodiments, the set of modules includes a link module that is configured to facilitate secure exchange of links with another VDAX to facilitate unique di-symmetric engagement.

In some of the embodiments, the set of modules include a sequence mapping module that is configured to genomically process sequences to derive genomic engagement factors having specific entropy, wherein the genomic engagement factors are used to encode digital objects in a non-recurring manner, and wherein the sequences are at least one of public sequences or private sequences. In some of these embodiments, the set of modules include a binary transformation module that is configured to encode digital objects into VBLS objects based on genomic engagement factors determined by the sequence mapping module, wherein each VBLS object contains an encoded digital object and metadata that is indicative of a public or private sequence that was used to generate a respective genomic engagement factor that was used to encode the encoded digital object. In some of these embodiments, the binary transformation module is further configured to decode received encoded digital objects that are included in received VBLS objects based on respective recreated genomic engagement factors.

In some embodiments, the ecosystem instance of the ecosystem security platform is configured with a respective set of modules that are each configured to execute a respective set of computationally complex information theory-facilitated computationally complex functions. In some of these embodiments, each set of information theory-facilitated based computationally complex functions is selected from cipher-based functions, cipherless functions, and hybrid functions that include at least one stage of at least one stage that is performed using a cipher-based function and at least one stage is performed using a cipherless function. In some of these embodiments, the set of modules of the ecosystem instance includes a root DNA module that manages the progenitor genomic data set and generates the progeny genomic data set.

In some of the embodiments, the digital ecosystem is a cloud services system. In some of the embodiments, the digital ecosystem is an enterprise information technology system. In some of the embodiments, the digital ecosystem is a computing device and the progeny VDAXs respectively correspond to hardware components and digital components of the computing device. In some of the embodiments, the digital ecosystem is a classified computing infrastructure. In some embodiments, the digital ecosystem is a traffic grid. In some of these embodiments, the traffic grid is an air traffic control grid. In some of these embodiments, the traffic grid is an autonomous vehicle traffic grid.

According to some embodiments of the present disclosure, a method for managing a set of digital entities in a digital ecosystem is disclosed. The method includes generating, by a processing system of an ecosystem VDAX, a progenitor genomic data set having specific entropy, wherein the progenitor genomic data set is assigned to the ecosystem VDAX. The method further includes generating, by the processing system, a plurality of different progeny genomic data sets that each exhibit the specific entropy. The method also includes, for each progeny of the plurality of different progeny genomic data sets, allocating, by the processing system, the progeny genomic data set to a respective digital entity of the set of digital entities, wherein the set of digital entities are enabled to achieve precision control of differences and correlation based on the respective progeny genomic data set of each respective digital entity.

In some embodiments, any pair of digital entities in the set of digital entities are configured to confirm correlation of the respective genomic data sets of the pair of digital entities and differentiate the respective progeny genomic data sets from any other progeny genomic data set based on the confirmed correlation of the progeny genomic data sets of the pair of digital entities to form a unique non-recurring relationship within the digital community. In some of these embodiments, the pair of digital entities are each configured to independently confirm correlation using a specific set of information theory-facilitated computationally complex functions.

In some of the embodiments, the set of information theory-facilitated computationally complex functions is one of cipher-based functions, cipherless functions, and hybrid functions that include at least one cipher-based function and at least one cipherless functions. In some of the embodiments, each digital entity of the pair of digital entities is configured to independently differentiate its respective progeny genomic data set using a second set of information theory-facilitated computationally complex functions.

In some of these embodiments, the second set of computationally complex functions are one of cipher-based functions, cipherless functions, and hybrid functions that include at least one cipher-based function and at least one cipherless function.

In some of the embodiments, in response to forming a unique non-recurring relationship, the pair of entities engage by generating and exchanging unique non-recurring virtual binary language script (VBLS) that is only decodable by the pair of entities based on the differentiated progeny genomic data. In some of these embodiments, the VBLS is comprised of encoded digital objects that retain information theory-facilitated genomic attributes of the respective genomic data sets of the pair of digital entities.

In some of the embodiments, the specific entropy is a configurable level of entropy that is defined by a community owner associated with the ecosystem VDAX. In some of the embodiments, the digital entities collectively enable virtual authentication, virtual affiliation, and virtual agility.

In some of the embodiments, the progeny genomic data set includes a genomic correlation object that exhibits the specific entropy and a genomic differentiation object that exhibits the specific entropy. In some of these embodiments, each progeny genomic data set includes a respective genomic eligibility object that exhibits the specific entropy.

In some of the embodiments, the digital ecosystem includes one or more digital enclaves that are formed on a respective mutual identity of interest expressed by controlled differences and correlation in the progeny genomic data sets. In some of these embodiments, each digital enclave includes one or more cohorts that share the respective mutual interest expressed by the controlled differences and correlation in the progeny genomic data sets.

A more complete understanding of the disclosure will be appreciated from the description and accompanying drawings and the claims, which follow.

BRIEF DESCRIPTION OF THE DRAWINGS

The accompanying drawings, which are included to provide a better understanding of the disclosure, illustrate embodiments of the disclosure and together with the description serve to explain the principle of the disclosure. In the drawings:

FIG. 3 illustrates attributes of Cyphergenics-based technologies in relation to the attributes (and potential shortcomings) of current and developing security-related technologies, according to some embodiments of the present disclosure.

DETAILED DESCRIPTION

Figure 1:
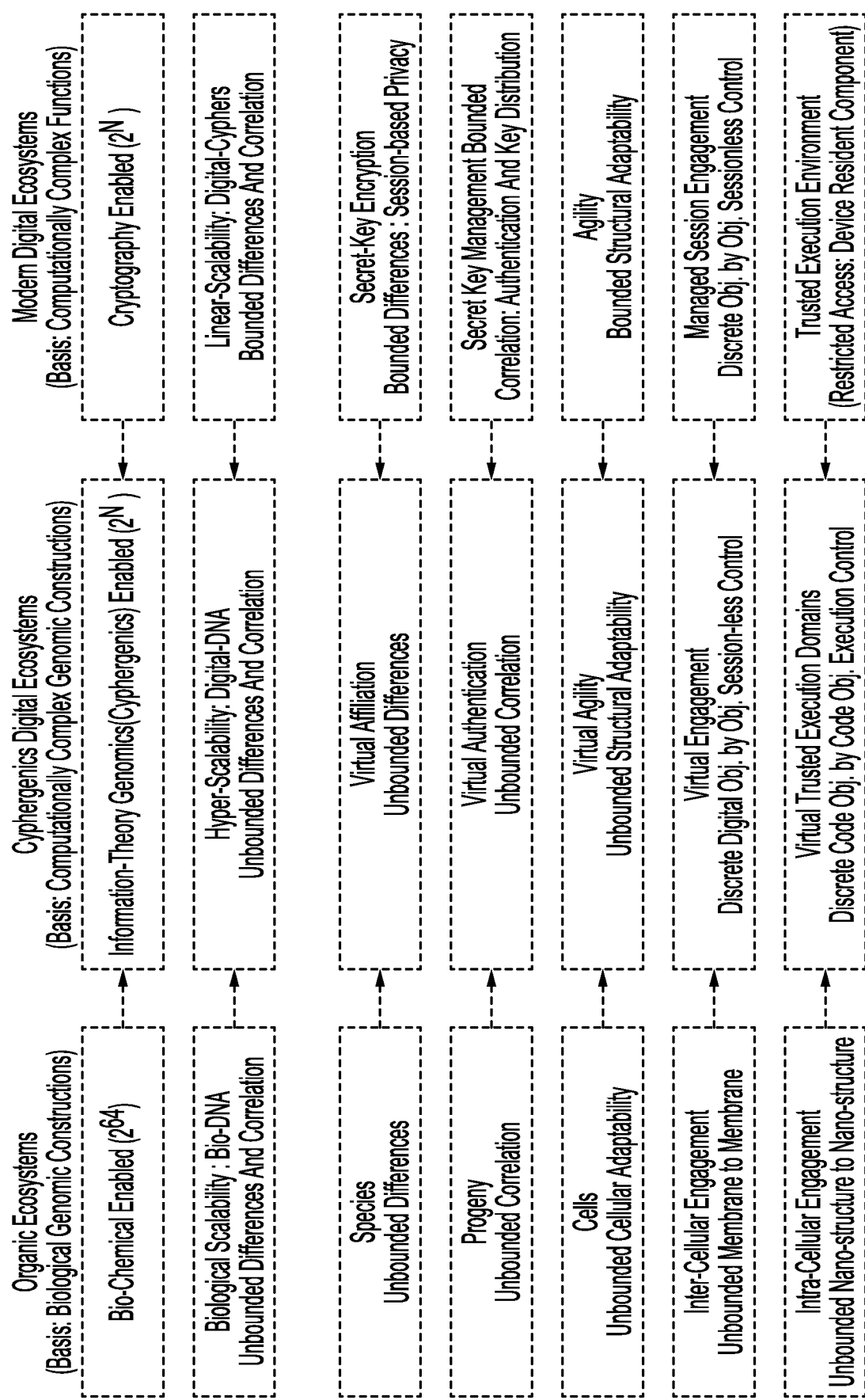
FIG. 1 is a schematic illustrating features of Cyphergenics-based digital ecosystems in relation to organic ecosystems and modern digital ecosystems, according to some embodiments of the present disclosure.
Figure 2:
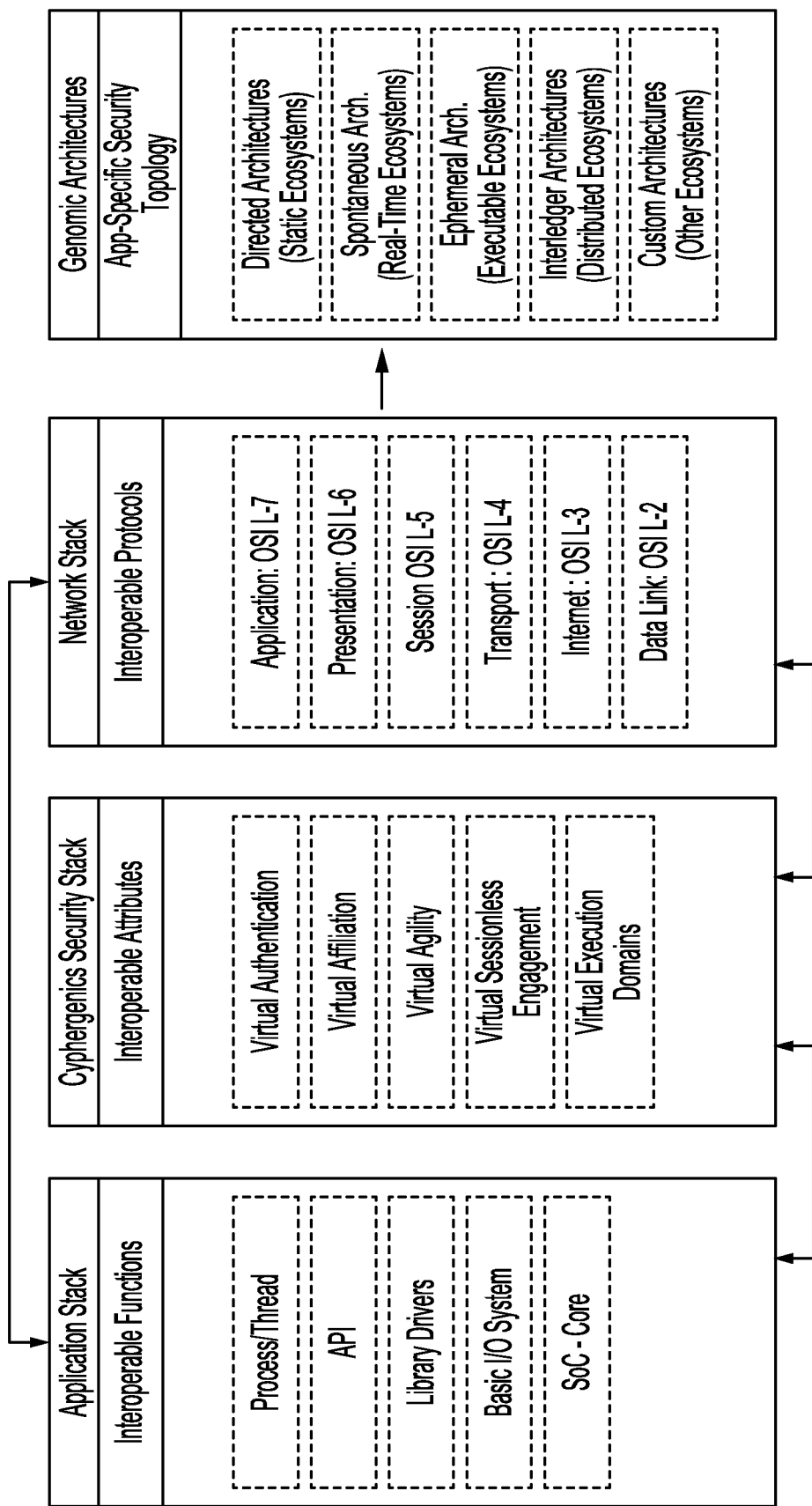
FIG. 2 illustrates a Cyphergenics-enabled security stack that may be applied coextensively with commonly known application and network stacks and examples of Cyphergenics-facilitated genomic architectures of digital ecosystems that may result from such application, according to some embodiments of the present disclosure.

It is submitted that hyper-scalability (e.g., where N digital cohorts have the ability to directly establish mutual identity of interest exhibiting high entropy with N different digital cohorts) is important to all things network-centric and the missing link to comprehensive security of dynamic-state-virtualization of digital ecosystems. Hyper-scalability (e.g., many-to-many) may facilitate wholly new network-centric virtualized products and services in addition to comprehensive security that prevailing linearly scalable technologies e.g., public key infrastructure (one-to-many) and quantum key distribution (one-to-one) cannot, no matter whether they achieve quantum resistant status or not.

As discussed herein, Cyphergenics-enabled hyper-scalability, which requires di minimis additional overhead or bandwidth, is equally effective and computationally undaunted across all Network and Application stack level although N×N engagement-instances might increase to increase to $N^X$ '$N^Y$. In embodiments, outcomes of hyper-scalable direct digital-cohort-to-digital-cohort virtual authentication and virtual affiliation are similar in outcome as hyper-scalable biological-progeny-to-biological-progeny virtual correlation and virtual differentiation, no matter the profoundly different base technologies by which each is accomplished. The same holds true for other digital attributes (e.g., virtual agility, virtual data objects, and virtual code objects), enabled by CG-based hyper-scalability.

Discussion of Cyphergenics, a wholly digitally fulfilled technology, is substantially assisted by adoption of corollary genomic terminology, having wholly bio-chemical fulfillment that is likely and hopefully more familiar to all but a few at this time. While the specific bio-chemical processes do not technically inform Cyphergenics, their ability to address similar challenges and levels of complexity added merit, after the fact, to Cyphergenics underlying propositions. Non-limiting examples of where Cyphergenics-based terms and computationally complex digital functions and processes and bio-chemical-based functions and processes share corollary genomic expression amongst others may include:

Genomic Information: numerical, narrative, or other such scripts, which elements in the aggregate exhibit little to no computationally discernable order or relationship.

Genomic Entropy: computationally assessable and confirmable degree to which recurring or predictable patterns are absent from the genomic information.

Genomic Construction: The ability to rearrange or reconfigure genomic information from its original sequence or relational basis to specific subsets without loss of relative entropy.

Genomic Modification: The ability to process genomic information based on computationally complex functions and processes, which computational properties remain provable if not observable, and consistent across the modified genomic information base.

Genomic Regulation: The ability to conditionally and temporarily modify a complete genomic information base or specific subset(s) in order to accomplish a specific objective (e.g., digital-cohort precision uncoordinated revocation), which requires pre-requisite knowledge of the then (i.e., modified) current base.

Genomic Revision: The ability to derive a subset of genomic information by reconstruction, modification, or regulation, which enable unique, computationally quantum proof, non-recurring transformation of digital-data-objects and digital-code-objects that nevertheless retain specific genomic correlation and differentiation attributes.

The present disclosure relates to various embodiments of Cyphergenics ecosystem security platforms (also referred to as "CG-ESPs", "security platforms", or "genomic security platforms") and CG-facilitated processes and techniques. In embodiments, a CG-ESP provides the computational resources and process control with which genomic information, genomic entropy, genomic construction, genomic modification, genomic regulation, and genomic revision uniquely collaborate to render computationally complex hyper-scalability. In embodiments, hyper-scalability, in turn, enables digital ecosystems, enclaves, and digital cohorts to engage on a genomic basis in order to achieve virtual authentication, virtual affiliation, virtual agility, virtual session-less engagement, and/or virtual execution domain attributes. In some embodiments, these attributes in turn facilitate application specific genomic network security topologies without replacement or reconfiguration of hardware connectivity.

In embodiments, instances of a CG-ESP may be parameterized with specific information theory-constructed genomic attributes (e.g., digital genomic data sets reflecting one or more mutual identities of interest of specific digital communities comprised in whole or in-part of ecosystem, enclaves, and/or digital cohorts (or "cohorts")). In embodiments, the parameterization of a CG-ESP instance with specific information theory-constructed genomic attributes configures a respective Virtual Anonymity Exchange controller (or "VDAX"), which may be executed by a processing system to enable the VDAX to perform a role within a respective digital community. In embodiments, a CG-ESP may enable multiple VDAXs no matter their having disparate or overlapping mutual identity of interests.

In embodiments, CG-ESPs may be configured to construct and manage digital correlation and differentiation functions on behalf of a digital ecosystem or components thereof. In embodiments, a digital ecosystem may refer to a digital community having one or more enclaves each having a mutual identity of interest. In embodiments, an enclave may refer to a set of one or more cohorts having a mutual identity of interest. In embodiments, the term "cohorts" may refer to independent cohorts and/or dependent cohorts. In some embodiments, independent cohorts may refer to a collection of one or more devices that operate as an independent entity. In some of these embodiments, independent cohorts may include, but are not limited to, grids, networks, cloud services, systems, computers, appliances, devices, and IoT devices. A dependent cohort may refer to an individual digital entity which is enabled by an independent cohort that acts as a surrogate on behalf of the individual digital entity. Examples of dependent cohorts include, but are not limited to, sensors, applications (apps), data, files, and content. As will be discussed, the designation of independent and dependent cohorts may vary across different types of architectures and ecosystems. For example, according to some embodiments of an ephemeral architectures (discussed below) certain device components (e.g., processors, processor cores, cameras, and the like) and software instances may be designated independent cohorts, while other device components and software instances may be designated dependent cohorts. It is noted that in some embodiments, these types of designations may be decided by a community owner associated with the digital ecosystem.

In example embodiments, a Cyphergenics-based ecosystem security platform ("CG-ESP") forms an ecosystem with one or more enclaves and manages membership of a collection of independent and dependent cohorts having a mutual identity of interest. In embodiments, a GC-ESP provides one or more core competences, such as a platform competence that controls and manages genomic functions and processes, and a link-exchange competence, which provides a means by which link data (e.g., genomic engagement cargo) is exchanged. In embodiments, a mutual identity of interest may be defined in accordance with any logical commonality between the cohorts within an enclave, which may be defined by or on behalf of a community owner. For example, mutual identities of interest may exist between user devices, servers, printers, documents, applications (e.g., cohorts) that form business units (e.g., enclaves) within an enterprise organization (e.g., digital ecosystem). In another example, mutual identities of interest may exist between the user devices, smart devices, gaming devices, sensors, wearable devices, files, and applications (e.g., cohorts) that operate on a home network (e.g., an ecosystem), such that the home network may have one or more enclaves (e.g., a work-related enclave used for a home office and a personal enclave for an individual or family's devices, applications, and files). In another example, mutual identity of interest may exist between autonomous vehicles (e.g., cohorts) that are driving on a particular grid (e.g., enclave) of a smart transportation system (ecosystem) managed by a regional authority (e.g., community owner). The foregoing are non-limiting examples of ecosystems, enclaves, cohorts, and identities of interest, and many other examples will be discussed throughout the document. Furthermore, it is noted that because a digital entity may be considered a cohort in a first ecosystem (e.g., a mobile device in an enterprise ecosystem), a digital entity may serve different roles within an ecosystem or across multiple ecosystems. For instance, a mobile device in an enterprise ecosystem may be considered an enterprise ecosystem cohort but may define an entire digital ecosystem in an executable ecosystem.

As will be discussed in greater detail, a configuration of CG-ESP may be defined by the community owner of a digital ecosystem. When referencing a "community owner" throughout the disclosure, the term may refer to the entity that administers, maintains, or owns the community (e.g., company, organization, government, individual human, or the like) and/or representatives thereof (e.g., network administrator, CIO, IT administrator, homeowner, consultant, security expert, artificial intelligence software acting on behalf of the community owner, or any other suitable representative). Furthermore, in some embodiments, a CG-ESP may be pre-configured and sold to the community owner, whereby the community owner may or may not be able to make decisions regarding community membership and/or decisions regarding the functionalities of the CG-ESP (e.g., which CG-ESP modules and configurations are used in the CG-ESP).

In the context of biology, core biological genomic competences, which include biological differentiation and correlation, provide a convenient corollary to describe formulation of CG-ESP digital processes. It is understood, however, that any reference to or derivations of "genomic" cohorts (e.g., genomic data sets, DNA, sequence mapping, mutating, cloning, and/or the like) in the context of Cyphergenics-related technologies is not intended to suggest that these processes mimic or inherent any or all specific properties of biological genomic constructions or processes. In embodiments, a CG-ESP executes genomic processes that may include digital generation, modification, corroboration, and/or allocation of specific types of genomic data. In embodiments, these genomic processes and data enable computation of differences and correlation exhibiting user-controlled entropy. In these embodiments, these digital genomic processes rely upon specific information theory-facilitated constructions. In some implementations, these constructions may be referred to as digital DNA (or genomic data). In embodiments, digital DNA may include one or more information theory-facilitated constructions, such as LNA (genomic correlation), CNA (genomic engagement-integrity), PNA (genomic engagement-eligibility), XNA (genomic differentiation), and/or ZNA (genomic code isolation/cloaking). As will be discussed, these Cyphergenics-based (or "CG-based") processes and constructions facilitate hyper-scalability across a wide array of digital ecosystems. Examples of CG-based processes may include, but are not limited to, CG-based link processes, CG-based sequence mapping, and/or CG-based transformations, example implementations of which are discussed throughout the disclosure.

In embodiments, genomic digital links (or "links") enable exchange of information necessary for a Virtual Digital Anonymity Exchange controller ("VDAX") (discussed further below) to perform higher level computationally complex genomic functions. In embodiments, CG-based genomic link processes may include link spawning, link hosting, and/or link updating, example implementations of which are described throughout the disclosure. These CG-based link processes provide attribute-specific genomic construction information, such as LNA (genomic correlation), CNA (genomic engagement-integrity), and PNA (genomic engagement-eligibility).

In embodiments, CG-based sequence mapping may refer to techniques used in the computational transformation of digital sequences (e.g., public or private protocol sequences) into genomic engagement factors. In embodiments, these genomic engagement factors may be unique and non-recurring. While different types of sequences may be broadly disparate, sequences may be processed in a manner that results in genomic engagement factors exhibiting specific levels of entropy. In embodiments, CG-based sequence mapping processes, compatible with a broad range of protocols and formats, may be initiated with respect to sequences exhibiting preexisting entropy, whereby sequences are respectively transformed by computationally complex CG-functions and processed into unique genomic engagement factors. These genomic engagement factors may then be used to encode digital objects into VBLS.

As will be discussed, embodiments of CG-ESPs may facilitate a number of hyper-scalable attributes that are not possible with modern cryptography and related security systems. These attributes may include, but are not limited to, virtual affiliation (unbounded differences), virtual authentication (unbounded correlation), virtual agility (unbounded structural adaptability), and Virtual Binary Language Script (VBLS), which enables virtual engagement (discrete data object-by-object session-less control), and virtual trusted execution domains (discrete code object by code object execution control). It is noted that the term "unbounded", as used herein implies unbounded in any practical sense of the word, while recognizing that it may be theoretically possible to describe a "bounded" scenario.

Hyper-Scalability: In some embodiments, hyper-scalability may refer to the ability to comprehensively associate N cohorts (or other community members) by M points of contact over T instances (M×N×T). Considering that there are billions of potential cohorts making countless points of contact and communicating over countless instances, hyper-scalability of such magnitude requires a fundamental breakthrough in modern cryptography. The CG-based systems described herein will create a significant reduction in computational expense and session states. In embodiments, these significant reductions come at the expense of relatively insignificant overhead and/or bandwidth.

Virtual Authentication: In embodiments, virtual authentication of ecosystem members (e.g., ecosystem, enclave, cohorts, etc.) may require hyper-scalability technologies. In embodiments, hyper-scalability technology enables ecosystem, enclave, and/or cohort engagement where precise and unique correlation (e.g., "who's who") may be required. In some of these embodiments, precise and unique correlation may refer to a specific set of information theory-facilitated genomic processes where a digital community (e.g., a cohort, enclave, ecosystem, or the like) to uniquely verify an identity of another member (e.g., another cohort, enclave, ecosystem, and/or the like). In embodiments, virtual authentication may refer to the ability to authenticate an unbounded number of ecosystem members (e.g., ecosystem, enclave, cohorts, and the like). As will be discussed, CG-enabled ecosystems may achieve unbounded correlation for the members of the ecosystem (e.g., enclaves, cohorts, dependent cohorts), which in turn provides for an unbounded amount of unique relationships to be formed. In some embodiments, of the present disclosure, cohorts from different ecosystems may also be configured to authenticate one another in an unbounded manner. As will be described, unbounded correlation may be achieved by genomic information theory-facilitated constructions and processes (also referred to as "Cyphergenics-based" or "CG-based" or "CG-enabled" constructions and/or processes).

Virtual Affiliation: In embodiments, virtual differentiated engagement between ecosystems, enclaves, and cohorts may require hyper-scalability. Hyper-scalability technology enables ecosystem, enclave, and cohort engagement for most, if not all, scenarios where precise and unique differentiation ("what's what" and "we're alone") may be required. In embodiments, precise and unique differentiation may refer to a set of congruent or sufficiently congruent processes that are performed by a unique pair of community members to establish a unique engagement that differentiates the pair from any other community members. In some of these embodiments, such precise and unique differentiation ensures that unintended digital entities cannot participate in the uniquely established engagement (e.g., decode intercepted data or the like). In embodiments, hyper-scalable differentiation may refer to the ability for an ecosystem member to uniquely affiliate with an unbounded number of other ecosystem members (e.g., ecosystem, enclave, cohorts, and/or the like). Organic ecosystems evidence powerful, although bounded, differentiation across species, progeny, and siblings, derived from complex bio-chemical processes. Nevertheless, unbounded differentiation may be achieved by specific genomic information theory based digital constructions and processes. As will be discussed, CG-enabled ecosystems may achieve unbounded differentiation for the members of the ecosystem (e.g., enclaves, cohorts, dependent cohorts) which in turn provides for an unbounded amount of unique relationships to be formed. In some embodiments, of the present disclosure, cohorts from different ecosystems may also be configured to form unique engagements in an unbounded manner. As will be described, unbounded differentiation may be achieved by genomic information theory governed constructions and processes (also referred to as "Cyphergenics-based" or "CG-based" constructions and/or processes).

Virtual Agility: In embodiments, virtual agility within ecosystem, enclave, and/or cohort platform stack(s) may be enhanced by hyper-scalability. Hyper-scalability technology enables ecosystems, enclaves, and cohorts to agilely execute hyper-scalable-differentiation and hyper-scalable-correlation for software and hardware managed processes. In some embodiments, agile execution of software and/or hardware managed processes may refer to processes that can be applied at various levels of a respective protocol stack (e.g., OSI-networking stack, software stack, processing stack, and/or the like). Organic Ecosystems evidence powerful, although bounded, agility at the cellular level controlled by complex bio-chemical processes. Nevertheless, unbounded agility may be achieved by specific genomic information theory-facilitated digital constructions and processes.

Virtual Binary Languages Script (VBLS): Virtual Binary Language Scripts-enabled Ecosystem, Enclave, and/or Cohort engagement requires hyper-scalability. Hyper-scalability technology can enable ecosystems, enclaves, and cohorts to engage via unique, non-recurring, computationally quantum proof binary languages (or non-quantum-proof binary languages if the community owner so desires). Organic ecosystems evidence powerful, although bounded, unique cellular engagement, based on complex bio-chemical processes. Nevertheless, unbounded unique digital object engagement, may be achieved by specific genomic information theory governed digital constructions.

Virtual Trusted Execution Domain: In some embodiments, employing computationally complex genomic constructions and processes, a suitably configured CG-ESP enables processes for uniquely transforming engagement for components of executable ecosystems. In embodiments, executable ecosystems may refer to different software and hardware components of a device (or a system of interdependent devices acting as a single unit). In embodiments, executable ecosystem components may include, but are not limited to, e.g.: application components (APIs, libraries, threads), operating system components (e.g., kernel, services, drivers, libraries, and the like), and system-on-chip (Soc) components (Processing Units, e.g., Core), hardware components (e.g., disks, sensors, periphery devices, and/or the like), and/or other suitable types components. In some embodiments, these ecosystem components (e.g., specific designations and organizations such as ecosystems, enclaves, and cohorts) may prosecute (e.g., encode and/or decode) executable binaries collaboratively or independently.

Genomic Facilitated Virtual Network Architectures: In embodiments, the genomic processes and competences of CG-EPSs enable inversion of the application security and network architecture relationship protocol, regardless of the unique demands of a particular use case. In some embodiments, the disclosed "genomic network topology" technology enables creation of wholly new use case-specific security architectures. In some embodiments, a single physical network topology may simultaneously support multiple genomic topologies. As used herein, a genomic topology or genomic network topology may refer to a topology of a digital ecosystem that is defined using the genomic constructions of the respective members of a digital ecosystem.

In embodiments, ecosystems, and enclaves as well as membership thereto may be defined by the owner of a digital community. For example, a network administrator affiliated with a corporate entity may configure a security platform instance, which establishes respective enclaves for different units or projects of the corporate entity. In this example, the network administrator may configure the security platform instance to add cohorts to one or more enclaves based on the cohort's function. It is noted that in some embodiments, a cohort can be included in multiple enclaves and enclaves may have overlapping cohorts. Furthermore, in some embodiments, multiple cohorts may be associated with a single device, such as a computing device and various hardware (e.g., CPU, GPU, memory devices) and/or software components (operating system, file systems, applications, files). As will be discussed, CG-ESPs may be configured to form many different types of ecosystems, and membership eligibility may be configurable and defined by the community owner and/or CG-ESP provider. In embodiments, the security platform is configured to "genomically" construct disparate functions, systems, and/or theaters of operation that are "genomically" based on mutual identity of interests. Put another way, in these embodiments, a CG-ESP may be configured and operated to (e.g., by a community owner or similar party) control the genomic network topology of a digital ecosystem using the genomic constructions of the community members (e.g., enclaves, ecosystems, and/or cohorts) within a digital community. In this way, community members can be established, added to certain enclaves or ecosystems, revoked from certain enclaves or ecosystems, and the like by modifying the genomic constructions of one or more members within the digital community.

In some embodiments, a Cyphergenics-based ecosystem security platform (CG-ESP) may refer to a set of CG-enabled modules that perform various CG-based functions on a specific configuration of genomic data, and a CG-ESP instance may refer to an instance of the CG-ESP platform having a configuration of the CG-enabled modules that is dependent on the role that the CG-ESP instance is performing with respect to a community (e.g., ecosystem-level, enclave-level, cohort level, dependent cohort level). In some embodiments, a CG-ESP platform instance may be embodied as a VDAX. In these embodiments, a VDAX may execute a specific configuration of CG-enabled modules that are defined for the role of the VDAX. Examples of VDAX roles may include ecosystem VDAX, enclave VDAX, cohort VDAX, and/or dependent VDAX, whereby each of these VDAXs may be configured in accordance with the CG-ESP modules and the CG-enabled operations necessitated by the role. In embodiments, a CG-ESP instance may provide one or more core competences, which may include control and management of genomic constructions, functions, and processes (platform competence) and/or secure data exchange functions and processes (link exchange competence). In embodiments, an ecosystem VDAX may perform security related functions on behalf of the ecosystem and may be considered the "progenitor" of the ecosystem. In some of these embodiments, one or more corresponding enclave VDAXs may be configured to perform security related functions on behalf of a respective enclave. In embodiments, a cohort VDAX may perform genomic security related functions on behalf of respective independent cohorts within an ecosystem. In embodiments, a dependent VDAX may perform genomic security related functions on behalf of a respective dependent cohort within an ecosystem. It is noted that in some embodiments, an independent cohort may host one or more dependent VDAXs on behalf of one or more dependent cohorts that depended on the independent cohort. Furthermore, in some embodiments, a single cohort VDAX associated with an independent cohort may be configured to perform security related functions for the cohort across disparate enclaves and ecosystems. In these embodiments, a cohort VDAX may manage and leverage different genomic data sets on behalf of the cohort according to a respective configuration of the different ecosystems and/or enclaves. For example, a mobile device that a user uses for work and personal matters may be configured with a cohort VDAX that manages and leverages one or more genomic data sets pertaining to the user's work ecosystem and enclaves in accordance with the CG-ESP configurations of the organization that the user works for as well as one or more genomic data sets pertaining to ecosystems and enclaves in which the user participates in accordance with the platform configurations of those ecosystems and enclaves. In some embodiments, one or more enclave VDAXs and/or an ecosystem VDAX can be hosted by the same computing system. For example, the ecosystem and enclave VDAXs of a large digital ecosystem (e.g., a federal or state government, large corporations, military, autonomous vehicle grid, IoT grid, or the like) may be hosted on a distributed cloud computing system (e.g., AWS®, Azure®, Google Cloud Services®, privately owned server banks, and the like), whereas the ecosystem and enclave security controllers of a small digital ecosystem (e.g., a home network, a small office network, a grass roots non-profit, or the like) may be hosted on a single computing device (e.g., a central server, a router, a mobile device, or the like). It is also noted that in some example embodiments, a VDAX may be configured to perform different roles with respect to different ecosystems.

For purposes of explanation, the terms "progenitor" and "progeny" (e.g., "progenitor security controller" or "progenitor VDAX" and "progeny security controller" or "progeny VDAX") may be used to denote a relationship where a "progenitor" VDAX may generate, assign, and/or otherwise provide a genomic data set to a "progeny" VDAX. For example, in some embodiments, an ecosystem VDAX may modify its own digital genomic data set for one or more enclaves, such that for each enclave, the "progeny" enclave VDAX thereof is assigned a unique, but correlated genomic data set that was derived from the "progenitor" ecosystem VDAX. Similarly, in another example, an enclave VDAX may modify its own genomic data set to generate, assign, and/or otherwise provide unique and correlated genomic data sets for the cohorts in the enclave, such that for each cohort, the progeny cohort VDAX thereof is assigned its own genomic data set. In this way, the progeny (e.g., progeny VDAXs) of a progenitor VDAX may be able to exchange data in a cryptographically secure manner in part due to the high degree of correlation between their respective genomic data sets. It is noted that in some embodiments of a CG-ESP platform, an ecosystem VDAX may generate and assign the genomic data sets for the cohorts of the ecosystem, even if there exists enclave VDAXs. In embodiments, a progenitor VDAX (e.g., an ecosystem or enclave VDAX) may provide a role-based configuration of a CG-ESP platform to a progeny VDAX, such that the progeny VDAX is configured with the proper CG-ESP modules given a role of the progeny VDAX with respect to the VDAX. As will be discussed, the configurations may include respective modules configured with specific cypher-based, cipherless, and/or hybrid computationally complex functions that are used in the discussed CG-based processes. In embodiments, a cipher-based function may refer to executed functions where all stages (one or more stages) of the function are performed using key-based reversable transformations (e.g., symmetric ciphers). Examples of key-based reversible functions may include but are not limited to Advanced Encryption Standard (AES), SAFER+, Serpent, Twofish, RC6, MARS, Camelia, MISTY1, SHACAL-2, Triple-DES, SAFER++, HC-138, Rabbit, Sasa20/12, SOSEMANUK, Grain, MICKEY, Trivium, and/or any other suitable key-based reversible functions now known or later developed. In embodiments, cipherless functions may refer to executed functions where none of the stages of the function are performed using key-based reversable functions. In embodiments, hybrid functions may refer to executed functions that include at least one stage that is performed using a cipher-based function and at least one stage is performed using a cipherless function. For example, a hybrid function may include a first stage where a cipher-based function is used to determine an intermediate value and a second stage where a cipherless transforms the intermediate value to an output value, which may or may not be reversable.

In some embodiments, CG-ESPs are configurable by the ecosystem owner or on behalf of the ecosystem owner. As mentioned, a CG-ESP may include a set of interdependent modules that collectively perform one or more genomic security functions, such that any level VDAX includes instances of some or all of the interdependent modules. It is noted that these interdependent modules may be implemented as executable instructions that are executed by a traditional processing device (e.g., CPU or GPU and/or FPGA, microprocessors, or special purpose chipsets) that are specifically configured to perform certain genomic functions. Put another way, the interdependent modules of a particular security controller instance (e.g., an ecosystem VDAX, an enclave VDAX, a cohort VDAX, a dependent VDAX, and/or the like) may be individually embodied as software, middleware, firmware, and/or hardware. Reference to processors, execution, or the like is meant to apply to any of these configurations, unless context specifically provides otherwise. In embodiments, the individual modules of a particular CG-ESP instance may be configured to operate on specific set of different types of genomic data objects (e.g., CNA, LNA, XNA, PNA, ZNA, or the like) and/or to execute different types of functions and strategies. For examples, some modules may be configured to apply cipher-based computationally complex functions to the genomic data objects and/or digital data generated or leveraged in connection to a genomic security operation. Examples of cipher-based computationally complex functions may include, but are not limited to, Advanced Encryption Standard (AES) encryption/decryption, SAFER+ encryption/decryption operations, proprietary privately developed encryption/decryption operations, and/or the like. Additionally or alternatively, in some embodiments, some of the interdependent modules may be configured to apply cipher-less computationally complex functions to the genomic data objects and/or digital data generated or leveraged in connection to a genomic security operation. Examples of cipher-less computationally complex functions may include, but are not limited to, cryptographic hash functions, transformations based on parametrized linear equations, transformations based on multivariable equations, lattice-based transformations, and the like. Additionally or alternatively, in some embodiments some modules may be configured to apply hybrid (e.g., cipher-based and cipherless) computationally complex functions to the genomic data objects and/or digital data generated or leveraged in connection to a genomic security operation. As discussed, a hybrid function may include some combination of cipher-based and cipherless functions. As will be discussed, a CG-ESP may be configured (e.g., by or on behalf of a community owner) in accordance with the needs and limitations of the digital community to which it serves.

In embodiments, a CG-ESP is configured to provide secure end-to-end data exchanges between ecosystem members using specific genomic data sets containing one or more digitally generated genomic constructions which may be embodied in objects (e.g., binary matrices, binary vectors, primitive binary polynomials, and the like) that exhibit configurable entropy. In embodiments, these digitally generated mathematical objects are used to securely exchange digital objects between any pair of sufficiently correlated ecosystem members by leveraging the high degrees of correlation and differentiability between the respective genomic data sets of the ecosystem members using a series of CG-based processes. In embodiments, hyper scalable genomic correlation may provide the ability to have an unbounded community of genomic progeny that can be directly authenticated as fellow enclave or ecosystem members without the support of out of bound trusted services (e.g., Certificate Authority, Secret Key Exchange, and the like). In some embodiments, hyper scalable differentiation may refer to the ability for two sufficiently affiliated cohorts to generate and exchange virtual binary language script (VBLS) (individual instances of which may be referred to VBLS objects) based on links that are hosted with respect to the other community member. In embodiments, a link includes digitally encoded instructions (which may be referred to as "genomic regulation instructions" or "GRI") from one VDAX to another VDAX that define a manner by which the genomic data set (e.g., XNA or ZNA) of the second VDAX is to be modified in order to the second VDAX to generate VBLS that can be decoded by the VBLS (assuming that the link is securely kept by the second VDAX). In embodiments, the second VDAX may "host" a link that indicates GRI corresponding to the first VDAX, whereby the second VDAX may modify its genomic data set based on the GRI, and may generate VBLS that is readable by the first cohort based on the modified genomic data. In embodiments, the second VDAX maps a sequence into the modified genomic data to obtain a genomic engagement factor, which is in turn used to encode a digital object (e.g., using disambiguation and/or encryption techniques) that is included in the VBLS object. In embodiments, VBLS objects may be data containers that include one or more encoded digital objects and metadata that is used to decode the encoded digital object(s). In embodiments, a first VDAX receives a VBLS object and decodes a digital object from the VBLS by modifying its own genomic data set using the GRI provided to the second VDAX, determining a genomic engagement factor based on its modified genomic data set, and decoding the encoded digital objects based on the genomic engagement factor. As will be discussed, only the first VDAX is able to decode digital objects from VBLS, while any other cohort (digital community member or otherwise) that does not have access to the GRI contained in the link information cannot decode the encoded digital objects in the VBLS.

As will be discussed, in embodiments, CG domain components (e.g., ecosystem, enclave, independent cohorts, and/or dependent cohorts) may be configured with digital genomic data sets, such that digital ecosystem CG-enabled components may achieve precision control of differences and correlation using information theory-facilitated computationally complex functions, which may be cypher-based, cipherless, and/or hybrid functions. In embodiments, CG-enabled methods may support CG-based genomic processes that enable dynamic specification of entropy. In embodiments, the CG domain components engage in accordance with information theory genomics (Cyphergenics) and may utilize information theory genomics that are capable of virtual authentication, virtual scalability, and/or virtual agility. In embodiments, the CG components are configured to generate VBLS, such that the CG-enabled processes enable two domain components to construct and engage via unique non-recurring digital languages (e.g., VBLS). In embodiments, the CG components provide the ability to establish and control differences and correlation between CG domain components, which may enable broad scalability (e.g., hyper-scalability). In embodiments, CG domain components engage via specific digital protocols comprised of digital objects, whereby the digital objects retain the information genomic attributes of their progenitor components (e.g., ecosystem or enclave). In embodiments, hyper-scalability, when exercised at the digital object level enables agile application of CG-based attributes beyond the component level (e.g., at the format and/or protocol level).

As mentioned, a genomic data set (also referred to as a "digital DNA set", "DNA set" or "DNA") may include one or more digitally generated mathematical constructions that exhibit specific levels of entropy, such that the levels of entropy is a configurable. As mentioned, for purposes of explanation, references to and derivations from biological genetic concepts are made. For example, terms such as DNA, "mutations", "genomic data", "genomic constructions", "progeny", "cloning", "sequence mapping" and the like are used throughout the disclosure. It should be understood that such references do not intend to ascribe any particular properties of biological genetic materials or processes to any of the terms used herein. Rather, the terminology is used to teach others how to practice various aspects of the disclosure. In embodiments, a genomic data set may include genomic eligibility object, a genomic correlation object, and/or a genomic differentiation object.

In embodiments, genomic eligibility objects may refer to digital generated mathematical objects that allow a pair of cohorts to genomically confirm engagement eligibility, which may be performed in part of a "trustless" authentication process between two VDAXs. In embodiments, a progenitor VDAX (e.g., an ecosystem VDAX) may derive progeny genomic eligibility objects for its progeny from its genomic eligibility object (a "progenitor genomic eligibility object"), such that each progeny receives a unique but correlated genomic eligibility object. Upon being assigned a genomic eligibility object, a progeny VDAX may receive a genomic eligibility object. In some embodiments, a progeny VDAX may receive a genomic eligibility via a one-time trusted event (e.g., upon ecosystem admission to a particular ecosystem, when a device is manufactured, configured, or sold, or the like). After this single trusted event, sufficiently VDAXs can independently confirm engagement eligibility with one another using their respective genomic eligibility objects. In embodiments, genomic eligibility objects may include CNA objects, PNA objects, or other suitable types of mathematical objects exhibiting configurable entropy level, correlation, and differentiation, which are discussed in greater detail below.

In embodiments, genomic correlation objects may refer to digitally generated mathematical objects that allow VDAXs to exchange links, whereby a link provides instructions that allow a pair of sufficiently correlated VDAXs to sufficiently differentiate themselves from other sufficiently correlated VDAXs in a digital community. In embodiments, the genomic correlation object is used by VDAXs to confirm link exchange correlation, which allows two ecosystem components (e.g., enclave and/or cohorts) to establish a specific relationship and engage one another. In example implementations, the genomic correlation objects of the community members of a digital ecosystem are LNA objects or any other suitable types of mathematical objects exhibiting configurable entropy and correlation, which are discussed in greater detail below.

In embodiments, genomic differentiation objects may refer to digitally generated mathematical objects that allow a pair of VDAXs (e.g., enclaves or cohorts) to generate and decode VBLS objects generated by the other respective VDAXs, provided the VDAXs are successfully hosting links spawned by the other respective VDAXs. In some embodiments, a first VDAX generates VBLS for a second VDAX in part by modifying its genomic differentiation object in the manner defined in the instructions contained in a hosted link corresponding to the second VDAX, and decodes VBLS from the second VDAX in part by modifying its genomic differentiation object in the manner defined in the instructions contained in a link hosted by the second VDAX with respect to the first VDAX. Examples of genomic differentiation objects may include, but are not limited to, XNA object, ZNA objects, or any other suitable types of mathematical objects exhibiting configurable entropy and correlation, which are discussed in greater detail below.

As will be discussed, different combinations and configurations of CG-ESP modules and genomic data sets can be used in different CG-ESPs. Contemporary network capabilities substantially reflect their underlying deployment architecture. VBLS-enabled genomic constructed architectures, operating at the bit level, may remain interoperable with the underlying deployment architecture. According to embodiments of the present disclosure, VBLS provides unprecedented facility and flexibility to uniquely tailored use cases—whether they be network, software, or hardware centric-architectures. Examples of different architectures include, but are not limited to: directed architectures that can be deployed in static ecosystems (e.g., large enterprises), free-form architectures that may be deployed in transient ecosystems (e.g., social networks, websites), spontaneous ecosystems that may be implemented for dynamic ecosystems (e.g., city-wide autonomous vehicles control system), ephemeral architectures that may be implemented for executable ecosystems (e.g., OS, browser), and/or Interledger architectures that may be implemented for affirmation ecosystems (e.g., Blockchains or other distributed ledgers). In embodiments, these architectures which overlay existing physical network topologies evidence genomic constructed topologies; multiple genomic constructed topologies may exist simultaneously and interoperably. Examples of different architectures and CG-enabled ecosystems are discussed throughout the disclosure.

Figure 4:
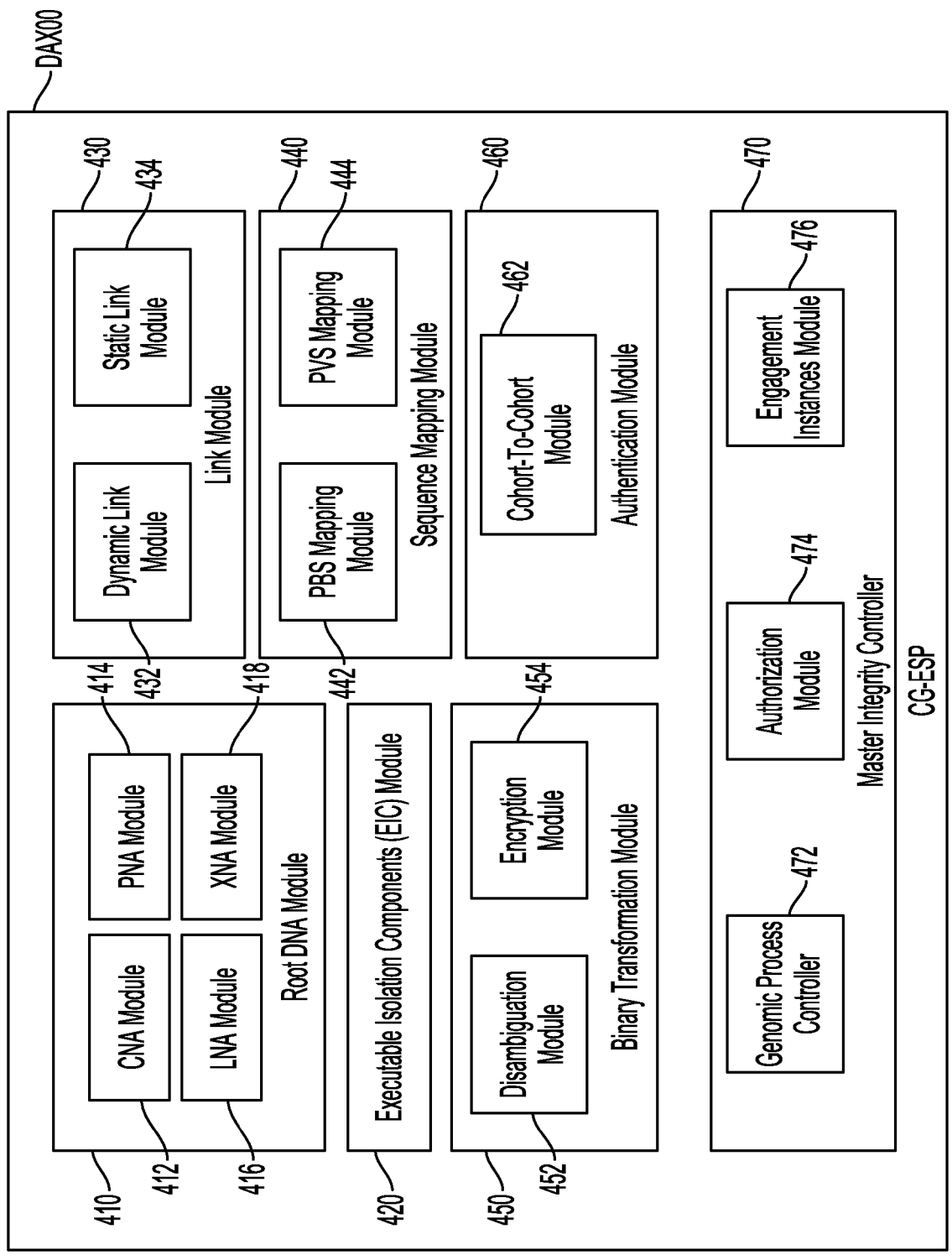
FIG. 4 illustrates an example configuration of a Cyphergenics-based ecosystem security platform, according to some embodiments of the present disclosure.

FIG. 4 illustrates an example of a CG-ESP 400 according to some embodiments of the present disclosure. In these embodiments, a CG-ESP 400 includes a set of CG-modules that are configured to perform a set of CG-processes and related computational methods with respect to a specific configuration of a genomic data set, such that different CG-ESPs 400 may include different CG-modules that perform different genomic functions and related computational methods that operate on a corresponding configuration of a genomic data set. In embodiments, a CG-ESP 400 is configured to be executed by ecosystem members having different roles (e.g., ecosystem VDAX, enclave VDAX, cohort VDAX, and/or dependent VDAX), such that different roles may execute some, all, or none of the CG-processes and computational methods defined in a respective CG-modules of the CG-ESP. In this way, all community members may participate in a CG-enabled digital ecosystem using a corresponding CG-ESP instance that is executed by the community member and/or on behalf of the community member (e.g., for dependent cohorts), such that the CG-ESP instance is configured for the role of the community member (e.g., ecosystem, enclave, cohort, or dependent cohort). For example, a community member serving as the ecosystem progenitor (e.g., ecosystem VDAX) may be configured with a CG-ESP instance that includes a CG module that defines CG-functions and related computational methods to generate genomic data sets (digital DNA sets) having one or more specific types of genomic data (e.g., CNA, PNA, LNA, XNA, and/or ZNA), whereas a community member that is an independent cohort (e.g., principal VDAX) within the ecosystem may be configured with a CG-ESP instance that includes CG modules that define CG-processes and computational methods for mutating its genomic data, exchanging links, sequence mapping, transforming digital objects, and the like. In this way, different community members of a CG-enabled ecosystem may execute different instances of a certain CG-ESP 400. It is noted that in some embodiments, the modules of an instance of a CG-ESP 400 executed by the VDAXs of the digital ecosystem which the CG-ESP instance supports. Furthermore, as the different types of VDAXs within a particular digital ecosystem may perform different roles within the digital ecosystem, the different classes of VDAXs of a CG-enabled ecosystem may execute some or all of the modules of the CG-ESP, and with respect to the individual modules, different classes of VDAXs of the CG-ESP instance may be configured to perform some or all of the genomic functions of the CG module. It is also noted that while different classes of VDAXs within a digital ecosystem may be configured to perform different respective roles within the digital ecosystem, all VDAXs that are configured to perform a certain CG-process with respect to the digital ecosystem (e.g., XNA and LNA modification, link exchange processes, VBLS generation/decoding, and/or the like) are configured with CG-ESP modules that include functionally identical functions that perform the certain CG-process (e.g., the same cipher-based, cipherless, or hybrid functions, functions that extract the same sequences, and the like). In this way, the sufficiently related VDAXs are able to perform certain CG-operations in a functionally congruent manner, which enables the sufficiently related VDAXs to, for example, confirm engagement eligibility and/or integrity, spawn and host links, and/or generate and decode VBLS objects.

In embodiments, the CG-modules of a CG-ESP 400 may include a root DNA module 410, an executable isolation components (EIC) module 420, a link module 430, a sequence mapping module 440, a binary transformation module 450, an authentication module 460, and/or a master integrity controller 470. As mentioned, in some embodiments, a CG-enabled digital ecosystem includes a set of VDAXs, whereby the set of VDAXs include two or more classes of VDAXs (e.g., ecosystem VDAX(s), enclave VDAX(s), cohorts VDAX(s), and/or dependent VDAX(s)). In some of these embodiments, the VDAXs of each class may execute respective instances of some or all of the CG-ESP modules (e.g., a root DNA module 410, EIC module 420, link module 430, sequence mapping module 440, binary transformation module 450, authentication module 460, and/or a master integrity controller 470). In embodiments, individual modules may be cypher-based, cipherless, and/or hybrid (e.g., include functions that are cypher-based and cipherless).

In embodiments, respective CG-ESP instances may be executed by respective processing systems that may include one or more CPUs, GPUs, microcontrollers, FPGAs, microprocessors, special-purpose hardware, and/or the like. Furthermore, in some embodiments, the modules of a CG-ESP instance may be executed in by a virtual machine or a container (e.g., a Docker container).

In embodiments, the CG-ESP 400 includes a root DNA module 410. In embodiments, the root DNA module 410 manages ecosystem specific data and genomic processes from which the root DNA module 410 formulates specific and highly rigorous difference and correlation enabling genomic constructions (e.g., DNA sets). In some embodiments, the root DNA module 410 may include a CNA module 412, a PNA module 414, an LNA module 416, and/or an XNA module 418.

In embodiments, a root DNA module 410 manages ecosystem specific data and CG genomic processes from which the root DNA module 410 formulates specific and highly rigorous difference and correlation-enabling CNA. In embodiments, CG-enabled ecosystem component eligibility-correlation is enabled by CG-genomic processes that formulate and construct CNA objects. In embodiments, the CNA module 412 may define CG-genomic processes and related methods that are configured to establish specific relationships between individual ecosystem components (ecosystems, enclaves, cohorts, and/or dependent cohorts). In embodiments, CNA may enable VDAXs of the same ecosystem to confirm eligibility for engagement. In embodiments, CNA enables ecosystem VDAXs and sub-ecosystem VDAXs to retain unique confirmation of eligibility for engagement. In embodiments, the CNA module 412 may be configured to prosecute genomic-based eligibility correlation using a wide range of information theory-facilitated computationally complex functions. In embodiments, these information theory-facilitated functions may be cypher-based, cipherless, or hybrid computationally complex functions.

In embodiments, a root DNA module 410 manages ecosystem specific data and CG genomic processes from which the root DNA module 410 formulates specific and highly rigorous difference and correlation-enabling PNA. In embodiments, CG-enabled ecosystem component eligibility-synchronization is enabled by CG-genomic processes that formulate and construct PNA objects. In some embodiments, the PNA module 414 defines CG-processes that employ CG-genomic processes and related computational methods to establish specific relationships between individual ecosystem components. In this way, PNA may enable ecosystem components (e.g., enclaves, cohorts, and/or dependent cohorts) of the same ecosystem to confirm eligibility for engagement. In embodiments, PNA enables ecosystem VDAX and descendant VDAXs sub-ecosystems to nevertheless retain unique confirmation of eligibility for engagement. In embodiments, a PNA root module 414 may be configured to prosecute genomic based eligibility-synchronization, which may be computed in accordance with a wide range of information theory-facilitated computationally complex functions. In embodiments, these information theory-facilitated functions may be cypher-based, cipherless, or hybrid computationally complex functions.

In embodiments, a root DNA module 410 manages ecosystem specific data and CG genomic processes from which the root DNA module 410 formulates specific and highly rigorous difference and correlation-enabling LNA. In some embodiments, CG ecosystem component link-exchange-correlation is enabled by CG-genomic processes which formulate and construct LNA objects. In embodiments, the LNA module 416 defines CG-processes and related computational methods to establish specific relationships between individual ecosystem components. In this way, LNA may enable certain VDAXs within an ecosystem (e.g., members of the same enclave) to confirm link-exchange-correlation. In embodiments, LNA enables VDAXs in a digital ecosystem to exchange information ("link exchange") which allows each to engage the other, whereby link-exchange bears corresponding computational complexity. In some embodiments, CG-based LNA-enabled link exchange is predicated on two sets of information, each unique to one of the parties such that the link-exchange between the parties (e.g., a first VDAX and a second VDAX) is unique (e.g., di-symmetric). In embodiments, LNA root modules 416 prosecute genomic based link-exchange-correlation, which may be computed in accordance with a wide range of information theory-facilitated computationally complex functions. In embodiments, these information theory-facilitated functions may be cypher-based, cipherless, or hybrid computationally complex functions.

In embodiments, a root DNA module 410 manages ecosystem specific data and CG genomic processes from which the root DNA module 410 formulates specific and highly rigorous difference enabling XNA. In these embodiments, ecosystem member engagement-differentiation may be enabled by CG-genomic processes that formulate and construct XNA objects. In embodiments, the root XNA module 418 employs XNA-specific CG-processes and related computational methods to establish specific relationships between individual ecosystem components. In embodiments, XNA enables VDAXs of the same ecosystem to confirm engagement-differentiation. In some embodiments, XNA enables VDAX (e.g., ecosystem VDAX, enclave VDAX, cohort VDAX, and/or dependent VDAX) of different ecosystems to confirm engagement-differentiation. Engagement-differentiation allows a pair of VDAXs to sufficiently differentiate themselves from other sufficiently correlated VDAXs for purposes of securely exchanging data, whereby the engagement bears corresponding computational complexity. In some embodiments, XNA-enabled engagement may be predicated on two sets of information, each unique to one of the parties, such that the engagement between the two VDAXs (e.g., a first VDAX and a second VDAX) is unique (e.g., di-symmetric). In embodiments, an XNA module 418 prosecutes genomic-based engagement differentiation, which may be computed in accordance with a wide range of information theory-facilitated computationally complex functions. In embodiments, the information theory-facilitated functions may be cypher-based, cipherless, or hybrid computationally complex functions.

In embodiments, an CG-ESP may include an EIC module 420 that manages ecosystem specific data and CG-genomic processes from which the EIC modules 420 formulate specific and highly rigorous difference enabling constructions called ZNA. In embodiments, ecosystem EIC engagement-differentiation is enabled by CG-genomic processes which formulate and construct ZNA objects. In embodiments, ZNA enables VDAXs of the same ecosystem to directly control genomic-enabled differentiation processes absent participation by other VDAX components. For example, in embodiments an EIC VDAX (e.g., core and memory) may employ ZNA-specific genomic processes and other related computational methods to establish differentiation with other specific EIC VDAXs. In embodiments, an EIC module 420 may define CG-processes for prosecuting genomic-based engagement differentiation, which may be computed in accordance with a wide range of information theory-facilitated computationally complex functions. In embodiments, the information theory-facilitated functions may be cypher-based, cipherless, or hybrid computationally complex functions.

In embodiments, a link module 430 defines a set of CG-processes and related computational methods that allow two VDAXs (e.g., a first VDAX and a second VDAX) to securely exchange information that is necessary to enable di-symmetric engagement. In some embodiments, link exchange exhibits the same level of entropy as the di-symmetric engagement. In some embodiments, a link module 430 instance may be configured to confirm engagement eligibility and link-exchange correlation with another VDAX. In embodiments, engagement eligibility and link-exchange correlation allow a pair of VDAXs to successfully exchange links (e.g., spawn links, and host links). In embodiments, a link module 430 may be configured to confirm engagement eligibility with another VDAX based on its genomic engagement object (e.g., CNA or PNA). For example, a link module 430 may confirm engagement-correlation using its corresponding CNA object and/or eligibly-synchronization using its corresponding PNA object.

In embodiments, a link module of a VDAX (e.g., a first VDAX) may be configured to confirm link-exchange-correlation with another VDAX based on a genomic correlation object of the first VDAX. In some embodiments, a link module 430 instance spawns a link for another VDAX (e.g., a second VDAX) based on a genomic correlation object (e.g., LNA object) of the first VDAX and information for the other VDAX to engage with the VDAX. In embodiments, a link module 430 instance of a VDAX (e.g., a first VDAX) may host a link by, in part, decoding information to engage with another VDAX from a link provided by or on behalf of the other VDAX using the genomic correlation object of the first VDAX. It is noted that different configurations of link modules 430 may utilize various CG genomic processes and related computational methods to execute secure link exchange across a wide range of interoperable digital communication media, digital networks, and/or digital devices. It is noted that link exchange between VDAXs may be executed asynchronously, in that the order of exchange does not affect the security of the protocol. Furthermore, in embodiments, link exchange may include one VDAX providing a link to another VDAX (e.g., symmetric) or both VDAXs providing links to the other respective VDAX (e.g., di-symmetric). In embodiments, a link module 430 may define CG-processes that prosecute genomic-based exchange of information, which may be computed in accordance with a wide range of information theory-facilitated computationally complex functions. In embodiments, the information theory-facilitated functions may be cypher-based, cipherless, or hybrid computationally complex functions.

As mentioned, a link may contain information that enables di-symmetric engagement. In embodiments, the information contained in a link may include genomic regulation instructions (GRI). In some embodiments, GRI may define instructions and/or data that are used to modify a genomic differentiation object (e.g., XNA or ZNA) in a deterministic manner, such that when a first VDAX provides a link to a second VDAX and the second VDAX successfully decodes the GRI contained in the link, both the first VDAX and the second VDAX are able to modify their respective genomic differentiation object using the GRI, which results in highly correlated copies of a modified genomic differentiation object (e.g., modified XNA or modified ZNA). As used herein, "highly correlated" when used in connection to genomic objects may refer to identical and/or otherwise sufficiently correlated genomic objects, whereby two genomic objects are said to be "sufficiently correlated" if the degree of correlation between two or more genomic objects enables an intended CG-operation or process to be performed successfully. In embodiments, GRI may include additional information such as instructions and/or data that are used by a VDAX during sequence mapping. As will be discussed in greater detail, such deterministic modification allows the two cohorts to differentiate themselves from all other cohorts to effectuate generation of secure VBLS. In embodiments, a link module 430 may generate GRI for a respective link, such that unique GRI are generated for any respective engagement. In some embodiments, a link module 430 may encode the GRI using a link-specific engagement factor to obtain encoded GRI. The link module 430 may generate genomic engagement cargo (GEC) that includes the encoded GRI and additional information that is used by the link hosting VDAX to decode the GRI from the GEC based on the information and the link hosting VDAX's genomic data. In embodiments, a link module 430 is further configured to decode a link (which is a part of "link hosting"), whereby a link module 430 obtains a genomic engagement factor based on the information contained in the GEC and its genomic data set and decodes the encoded GRI using the genomic engagement factor to obtain the GRI. The decoded GRI may then be used by the link hosting VDAX when generating VBLS for the link spawning VDAX that provided the link.

In embodiments, a link module 430 may be further configured to update links. Link updating may refer to a process by which the genomic regulation instructions (GRI) that were provided by a first VDAX to a second VDAX for a specific engagement between the pair of VDAXs are modified. A link may be updated for any number of reasons, including concerns that a link has been compromised and/or in accordance with routine security protocols (e.g., links are updated daily, weekly, or monthly, or in response to a cohort request to update a link). In some embodiments, a link module 430 may update a link by generating link update information, whereby the link update information is provided from the VDAX that spawned the link to a VDAX that is hosting the link. In embodiments, link update information may include new GRI that replace the current GRI. In other embodiments, link update information may include data that is used to modify the current GRI. For example, the link update information may be a value that is used to transform the GRI, such that the hosting VDAX applies the value to the current GRI using one or more computationally complex functions (e.g., cypher-based, cipherless, or hybrid functions) to obtain the updated GRI. In some embodiments, link updating differs from link exchange in that link update information can be encoded in VBLS, as opposed to link exchange which may include more computationally expensive operations. Thus, link exchange may be performed as a one-time process, and link updating may be performed any number of times and/or for any suitable reason.

In embodiments, links may be static links or dynamic links. In embodiments, dynamic links may refer to links that contain additional information that further differentiates a pair of cohorts. In some embodiments, dynamic links may contain executable code (or references to executable code) that is used to alter one or more of the functions performed by the pair of VDAXs, but only with respect to their engagement. For example, a dynamic link may include executable code that alters an XNA/ZNA modification function, sequence mapping function and/or a binary transformation function for a respective engagement. In this way, when a pair of VDAXs exchange a dynamic link, the pair of cohorts may execute the executable code in lieu of or in addition to the default code when performing a particular function (e.g., XNA/ZNA differentiation, sequence mapping, and/or binary transformation). In embodiments, static links may refer to links that are used in engagements where the configuration of a CG-ESP is unaltered for a particular engagement.

In embodiments, a static link modules 432 define CG processes that enable two VDAX (e.g., a first VDAX and a second VDAX) to securely exchange (e.g., spawn link and host link) information necessary to enable unique di-symmetric engagement, which exchange exhibits the same level of entropy. In embodiments, the rules and processes governing static links are prescribed by the highest class VDAX in the ecosystem (e.g., an ecosystem VDAX), whereby the rules may apply to all linking VDAXs in the ecosystem. In embodiments, static link module 432 instances may execute CG-processes related to CNA that are used for eligibility-correlation and/or PNA that are used for eligibility-synchronization. In some embodiments, static link module 432 instances execute CG-processes related to LNA that are used for link-exchange-correlation. In embodiments, a CG platform instance may be configured to execute processes to facilitate secure link exchange across a wide range of interoperable digital communications media, digital networks, and/or digital devices. In embodiments, VDAXs may perform link exchange asynchronously, in that the order of the exchange does not affect the security of the protocol. Furthermore, in embodiments, link exchange may include one VDAX providing a link to another VDAX (e.g., symmetric) or both VDAXs providing links to the other respective VDAX (e.g., di-symmetric). In some embodiments, link module 432 instances prosecute genomic-based engagement differentiation, which may be computed in accordance with a wide range of information theory-facilitated computationally complex functions. In embodiments, the information theory-facilitated functions may be cypher-based, cipherless, or hybrid computationally complex functions.

In embodiments, a dynamic link modules 434 define CG-processes that enable two VDAXs (e.g., a first VDAX and a second VDAX) to securely exchange (e.g., spawn link and host link) information necessary to enable unique di-symmetric engagement, whereby exchange exhibits the same level of entropy. In embodiments, the rules and processes governing dynamics links are prescribed by the highest class VDAX in the ecosystem (e.g., an ecosystem VDAX), including the authority to establish additional genomically compatible link-exchange instructions and processes.

In embodiments, a dynamic link module 434 may generate dynamic links that include executable instruction sets (e.g., binary code, script, and a like) that modify various CG-processes as allowed by the highest level VDAX in the CG-enabled ecosystem. In these embodiments, an executable instruction set in a dynamic link may override the functions of certain modules (e.g., XNA module, sequence mapping module and/or binary transformation module) for a specific engagement. In this way, a pair of VDAXs that have exchanged a dynamic link can change their CG-processes that are performed with respect to that specific engagement, which may provide an additional layer of security. In some embodiments, a dynamic link module 434 may include an interpreter or just-in-time compiler that processes the instruction set included in a dynamic link, such that the processed instruction set is executed with respect to a specific engagement to override one or more CG-processes that are performed during said engagement. In some embodiments, a first dynamic link module 434 instance may spawn a dynamic link that includes the executable instruction set. In these embodiments, a second dynamic link module 434 instance of a second VDAX may decode the dynamic link, such that when the second VDAX is generating VBLS to the first VDAXs, the respective dynamic link modules 434 may both use the overriding CG-process(s) for that specific engagement. The second VDAX may use the overriding CG-process(s) to generate the VBLS, while the first VDAX may use the overriding CG-process(s) to decode the VBLS. It is appreciated that data exchange in the opposite direction using a second dynamic link from the second dynamic link module 434 instance to the first dynamic link module 434 instance may operate in the same manner, in that the first VDAX uses the overriding CG-process(s), as defined in the second dynamic link, to generate second VBLS, while the second VDAX uses the overriding CG-process(s) to decode the second VBLS.

In embodiments, a dynamic link module 434 instances may establish instructions and related CG-processes processes not shared by other VDAXs, which may be governed by a wide range of options, circumstances, conditions, and objectives. In embodiments, dynamic links provide additional levels of security, as the CG-processes themselves are modified in a unique manner for a unique pair of VDAXs.

In embodiments, a dynamic link module 434 may perform dynamic link exchange asynchronously, in that the order of the exchange does not affect the security of the protocol. Furthermore, in embodiments, link exchange performed by a dynamic link module 434 may include one VDAX providing a link to another VDAX (e.g., symmetric) or both VDAXs providing links to the other respective VDAX (e.g., di-symmetric). In embodiments, dynamic link module 434 instances prosecute genomic-based engagement differentiation, which may be computed in accordance with a wide range of information theory-facilitated computationally complex functions. In embodiments, the information theory-facilitated functions may be cypher-based, cipherless, or hybrid computationally complex functions.

In embodiments, a sequence mapping module 440 may define a set of CG-processes and computational methods that perform sequence mapping. In some embodiments, sequence mapping may be an important computation for transforming unique non-recurring digital objects. In embodiments, sequence mapping module 440 instances may be configured to map public sequences (e.g., public protocol and/or format dependent metadata) and/or private sequences (e.g., private and proprietary protocols and/or format dependent metadata) into a (modified) genomic data object. Regardless if the sequences are public or private, the sequences may be broadly disparate (e.g., TCP, UDP, TLS, HTTP, H.265, or other public or private sequences) and may be mapped into modified genomic data to obtain results (e.g., genomic engagement factors) that exhibit specific levels of entropy. In embodiments, a sequence mapping module 440 may include a public sequence mapping module 442 and/or a private sequence mapping module 444.

In embodiments, a public sequence mapping module 442 may define CG-enabled processes and related methods that are configured to select specific sequences from public sources (e.g., specific protocol or format dependent metadata). In some embodiments, a public sequence mapping module 442 instance may process a given public sequence ("PBS1") to derive a specific value ("V1") (e.g., using a hash function or another computationally complex function). In embodiments, the resultant value, V1, is in turn processed in accordance with (e.g., mapped into) a genomic differentiation object (e.g., XNA1) associated with the public sequence to produce a unique vector exhibiting specific entropy (e.g., a genomic engagement factor). In embodiments, the value, V1, may be processed in accordance with (e.g., mapped into) an alternative genomic differentiation object (e.g., XNA2) to produce a different unique vector exhibiting specific entropy. In embodiments, a resultant vector may exhibit a level of entropy that vastly exceeds the size of the public sequence used to derive the vector. In embodiments, public sequence mapping modules 442 produce unique vectors capable of leveraging specific facilities present in unrelated protocols and formats. In embodiments, public sequence mapping modules 442 execute genomic processes computed in accordance with information theory-facilitated complex functions to produce unique vectors based on public sequences and a genomic differentiation object (e.g., a modified XNA object). In embodiments, these information theory-facilitated functions may be cypher-based, cipherless, or hybrid computationally complex functions.

In embodiments, a private sequence mapping module may define CG-enabled processes and related methods that are configured to select specific sequences from private sources (e.g., private and/or proprietary protocol or format dependent metadata) and to derive a unique vector that exhibits specific entropy. In some embodiments, a private sequence mapping module 444 instance may process a given private sequence ("PVS1") to derive a specific value ("V1"). In embodiments, the resultant value, V1, is in turn processed in accordance with (e.g., "mapped" into) a genomic differentiation object (e.g., XNA1) associated with the private sequence module 444 to produce a unique vector exhibiting specific entropy. In embodiments, the value, V1, may be processed in accordance with (e.g., mapped into) an alternative genomic differentiation object (e.g., XNA2) to produce a different unique vector exhibiting specific entropy. In embodiments, a resultant vector may exhibit a level of entropy that vastly exceeds that of the private sequence used to derive the vectors. In embodiments, private sequence mapping module 444 instances produce unique vectors capable of leveraging specific facilities present in unrelated private protocols and formats. In embodiments, private sequence mapping module 444 instances execute genomic processes computed in accordance with a set of information theory-facilitated computationally complex functions to produce unique vectors based on private sequences and a genomic differentiation object (e.g., a modified XNA object). As used herein, the term "set of information-theory facilitated computationally complex functions" may denote some combination of one or more information-theory facilitated computationally complex functions. In embodiments, these information theory-facilitated functions may be cypher-based, cipherless, or hybrid computationally complex functions that include at least one stage that leverages cipher-based functions and at least one stage that leverages cipherless functions.

In embodiments, a binary transformation module 450 may define a set of CG-processes and related computational methods that are configured to generate virtual binary (e.g., object-to-object) language script (VBLS). In embodiments, binary transformation module 450 instances transform digital objects (e.g., packets, sectors, sequences, and/or frames) having specific formats and protocols by various computational methods (e.g., disambiguation methods and/or encryption methods). In embodiments, binary transformation module 450 instances are configured to encode digital objects based on values (e.g., genomic engagement factors) determined by a corresponding sequence mapping module 440 to produce encoded digital objects that may be unique, non-recurring, and/or computationally quantum proof. In embodiments, binary transformation module 450 instances may be further configured to decode the encoded digital objects using values (e.g., genomic engagement factors) that are determined by a corresponding sequence mapping module 440. In embodiments, binary transformation modules 450 may include disambiguation modules 452 and/or encryption modules 454.

In embodiments, a disambiguation module 452 may define CG-processes and computational methods that perform binary transformation of digital objects in accordance with genomically derived genomic engagement factors produced by a corresponding sequence mapping module 440 instance, whereby the resultant encoded digital objects are only subject to brute-force attack. In embodiments, a disambiguation module 452 instance may transform a digital object based on a genomic engagement factor by performing an XOR operation on the genomic engagement factor and the digital object to obtain the encoded digital object. In embodiments, a disambiguation module 452 instance may be configured to receive a different genomic engagement factor for each digital object, as disambiguation techniques may be attackable with more efficient attacks if a same genomic engagement factor is used to encode two or more digital objects. In embodiments, a disambiguation module 452 instance may be configured to decode an encoded digital object using an inverse disambiguation function and a genomic engagement factor. Assuming the genomic engagement factor matches the genomic engagement factor that was used to encode the digital object, the inverse disambiguation function outputs the decoded digital object given the genomic engagement factor and the encoded digital object. In embodiments, a disambiguation module 452 instance executes genomic processes in accordance with information theory-facilitated complex functions. In embodiments, these information theory-facilitated functions may be cypher-based, cipherless, or hybrid computationally complex functions.

In embodiments, an encryption module 454 may define CG-processes and computational methods that perform binary transformation of digital objects in accordance with genomically derived genomic engagement factors produced by a corresponding sequence mapping module 440 instance, whereby the resultant encoded digital objects are only subject to brute-force attack. In embodiments, an encryption module 454 instance may transform a digital object based on a genomic engagement factor using any suitable encryption function that receives the genomic engagement factor and the digital object as input and outputs the encoded digital object. In embodiments, the encryption function that is used must have a corresponding inverse encryption function (or decryption function) that may be used to decode an encoded digital object. In embodiments, an encryption module 454 instance may be configured to receive a different genomic engagement factor for each digital object or may use the same transformation for two or more different digital objects.

In embodiments, an encryption module 454 instance may be configured to decode an encoded digital object using an inverse encryption function and a genomic engagement factor. Assuming the genomic engagement factor matches the genomic engagement factor that was used to encrypt the digital object, the inverse encryption function outputs the decoded digital object given the genomic engagement factor and the encoded digital object. In embodiments, encryption module 454 instances execute genomic processes in accordance with information theory-facilitated computationally complex functions. In embodiments, these information theory-facilitated functions may be cypher-based, cipherless, or hybrid computationally complex functions.

In embodiments, an authentication module 460 may define CG-processes and computational methods that are configured to authenticate VDAXs that have a common genomic construction. As discussed, digital ecosystems that are constructed by a highest level VDAX (e.g., ecosystem VDAX) have specific distributions of genomic data (e.g., CNA, PNA, LNA, XNA, and/or ZNA) also have specific genomic eligibility-correlation, eligibility-synchronization link exchange-correlation, and/or engagement-correlation attributes. In embodiments, authentication module 460 instances may be configured to enables a corresponding VDAX to confirm engagement correlation of any other VDAX having common construction (e.g., related genomic data), regardless of their primary genomic construction (e.g., members of a different enclave in a digital ecosystem). In embodiments, an authentication module 460 may include a cohort-to-cohort module 462 that defines CG-processes and related computational methods that enable a corresponding VDAX to confirm engagement correlation with another VDAX from the same CG-enabled digital ecosystem based on their common genomic construction, regardless of which enclave(s) the VDAXs belong to. In embodiments, authentication module 460 instances are configured to prosecute secure genomic-based engagement correlation of genomic data sets in accordance with information theory-facilitated computationally complex functions. In embodiments, these information theory-facilitated functions may be cypher-based, cipherless, or hybrid computationally complex functions.

As discussed, conformance of root DNA constructions and supporting genomic processes (e.g., link generation, engagement correlation, VBLS generation, and the like) are directly managed and controlled by a specific configuration of CG-modules. In embodiments, respective CG-ESPs may include a master integrity controller 470 CG-processes and related computational methods that manage module conformance on behalf of the VDAX. In embodiments, master integrity controllers 470 may include CG-processes and related computational methods that ensure the veracity of the operational performance and configuration management for VDAXs across digital ecosystems. In embodiments, a master integrity controller 470 may include a genomic process controller 472, an authorization module 474, and an engagement instances module 476.

In embodiments, the engagement of VDAXs, their genomic modules, and other such functional modules, may be controlled by respective master integrity controller 470 instances of respective CG-ESP instances (e.g., which may be executed by a corresponding VDAX). In embodiments, a master integrity controller 470 instance leverages computationally complex functions to engage with specific modules (e.g., 1 to N). In some of these embodiments, the master integrity controller 470 instance will have a respective genomic data set (e.g., CNA, PNA, LNA, and/or XNA) as do the modules and may use the computationally complex functions to engage with and manage specific modules. In some embodiments, the genomic process controller 472 may validate an integrity of the modules and authenticate the modules using its genomic data and the computationally complex functions. In these embodiments, genomic process controller 472 instances are not configured to determine the processes nor functions carried out by a respective VDAX. In to protect the computationally complex genomic processes carried out by the respective VDAX, the genomic process controller 472 may control operational processes and functions attendant to the correct application of module processes and functions and may also render certain operational processes and functions to the correct application of module processes and functions under control of the specific modules. Put another way, in embodiments, the genomic process controller 472 may confirm the source of a CG-ESP module instance and/or confirm or deny the integrity of the CG-ESP instance, as well as any processes and operations that are performed in support of the module instances (e.g., the processes that connects the modules for various CG-based functions).

In embodiments, VDAXs that utilize the same computationally complex genomic functions as do the modules and master integrity controller 470 are capable of confirming or disqualifying specific CG-ESP configurations. For example, in embodiments VDAXs (e.g., ecosystem VDAX, enclave VDAX, cohort VDAX, and/or dependent VDAX) utilizing the same computationally complex genomic functions as do the modules and the master integrity controller 470, are capable of confirming or disqualifying specific CG-ESP configurations. In embodiments, a VDAX utilizing the same computationally complex genomic functions as do the modules and master integrity controller 470, is capable of confirming, disqualifying or modifying specific CG-ESP configurations. In embodiments, a master integrity controller 470 may include a genomic process controller 472, an authorization module 474, and an engagement instances module 476. In embodiments, genomic processes controller modules 472 instances prosecute secure genomic based confirmation, disqualification, and modification of VDAX modules and specific VDAX configurations which may be computed in accordance with a wide range of information theory-facilitated computationally complex functions. In embodiments, these information theory-facilitated functions may be cypher-based, cipherless, or hybrid computationally complex functions.

In embodiments, VDAXs (e.g., ecosystem VDAX, enclave VDAX, cohort VDAX, and/or dependent VDAX) provide tremendous adoption, deployment, and operational flexibility in that configuration control can be affected horizontally and or hierarchically. In embodiments, this flexibility derives from the same inherent computationally complex genomic functions (e.g., correlation and differentiation) facilitated by CG-ESP modules. In embodiments, a VDAX (e.g., ecosystem VDAX, enclave VDAX, cohort VDAX, and/or dependent VDAX) may be uniquely configured and enabled, such that a single ecosystem or enclave VDAXs (e.g., a progenitor) can determine the operational configuration of other VDAXs (e.g., master integrity controller 470 inter-communication). In embodiments, a progenitor (e.g., an Ecosystem VDAX or Enclave VDAX) can directly confirm or disqualify the operational standing of other VDAXs based on their configurations. In embodiments, a progenitor (e.g., an Ecosystem VDAX or Enclave VDAX) may possess unique genomic properties configured and enabled, such that authorized module updates of VDAXs may be executed in conjunctions with the other authorized CG-ESP modules. In embodiments, master authorization module 474 instances prosecute secure genomic based confirmation, disqualification, and modification of VDAX modules and specific VDAX configurations which may be computed in accordance with a wide range of information theory-facilitated computationally complex functions. In embodiments, these information theory-facilitated functions may be cypher-based, cipherless, or hybrid computationally complex functions.

In embodiments, engagement between two or more VDAXs (e.g., ecosystem VDAX, enclave VDAX, cohort VDAX, and/or dependent VDAX) using EG-CSP enabled computationally complex genomic functions constitutes a single security-instance. In some embodiments, these security-instances may be aggregated as per the hierarchical genomic relationship exhibited by a particular digital ecosystem community. In embodiments, security-instances aggregated at lower levels may be passed to the next or any other higher point of aggregation (e.g., cohort VDAXs to enclave VDAXs), and so on (e.g., cohort VDAXs and enclave VDAXs to ecosystem VDAXs). In embodiments, the communication between VDAX modules (e.g., security-instance reporting) may be based on the same or different computationally complex genomic functions by which their primary security-instances are managed. In embodiments, master engagement instance module 476 instances enable VDAXs (e.g., ecosystem VDAX, enclave VDAX, cohort VDAX, and/or dependent VDAX) to track security-instances as per a set of engagement tracking policies. In some embodiments, these policies may stipulate how security-instances are defined. In embodiments, these definitions may bear specific computationally complex security functions. In embodiments, master engagement instance module 476 instances enable VDAXs (e.g., ecosystem VDAX, enclave VDAX, cohort VDAX, and/or dependent VDAX) to calculate the number of security-instances are created, as per an Engagement Accounting Policies. In embodiments, these policies stipulate how security-instances are accumulated. In embodiments, such accumulation may bear specific computationally complex security functions. In embodiments, master engagement instance module 476 instances enable VDAXs (e.g., ecosystem VDAX, enclave VDAX, cohort VDAX, and/or dependent VDAX) having common construction to be capable to report security-instances to other VDAXs (e.g., ecosystem VDAX, enclave VDAX, cohort VDAX, and/or dependent VDAX) as per a set of engagement reporting policies. In embodiments, these policies stipulate how security-instances are reported, how frequently, and to whom. In embodiments, such reporting bears specific computationally complex security functions. In some embodiments, VDAXs (e.g., ecosystem VDAX, enclave VDAX, cohort VDAX, and/or dependent VDAX) may be uniquely configured and enabled, such that a single VDAX (e.g., ecosystem VDAX) may define the digital ecosystem (e.g., community) engagement tracking policies, engagement accounting policies, and/or engagement reporting policies. In some embodiments, a single engagement instances module 476 instance may execute multiple tracking policies, accounting policies, and/or reporting policies using specific computationally complex genomic functions.

In embodiments, the master engagement instances module enable a VDAX (e.g., ecosystem VDAX, enclave VDAX, cohort VDAX, and/or dependent VDAX) having common construction (e.g., an ecosystem VDAX) to be capable to aggregate security-instances from other VDAX (e.g., ecosystem VDAX, enclave VDAX, cohort VDAX, and/or dependent VDAX) enabled by specific computationally complex genomic functions, as per the engagement reporting policies. In embodiments, master engagement instances module 474 instances prosecute secure genomic based tracking, accounting, reporting, and aggregation of VDAX genomic specific security-instances which may be computed in accordance with a wide range of information theory-facilitated cryptographic computationally complex functions. In embodiments, these information theory-facilitated functions may be cypher-based, cipherless, or hybrid computationally complex functions.

It is appreciated that FIG. 4 is provided for explanatory purposes. Additional or alternative modules may be used to configure a CG-ESP without departing from the scope of the disclosure. As discussed, different CG-ESPs may be configured to perform different CG-operations on different configurations of genomic data sets. Examples of genomic data sets and different CG-operations that are performed with respect to genomic data are discussed in greater detail below.

Figure 5:
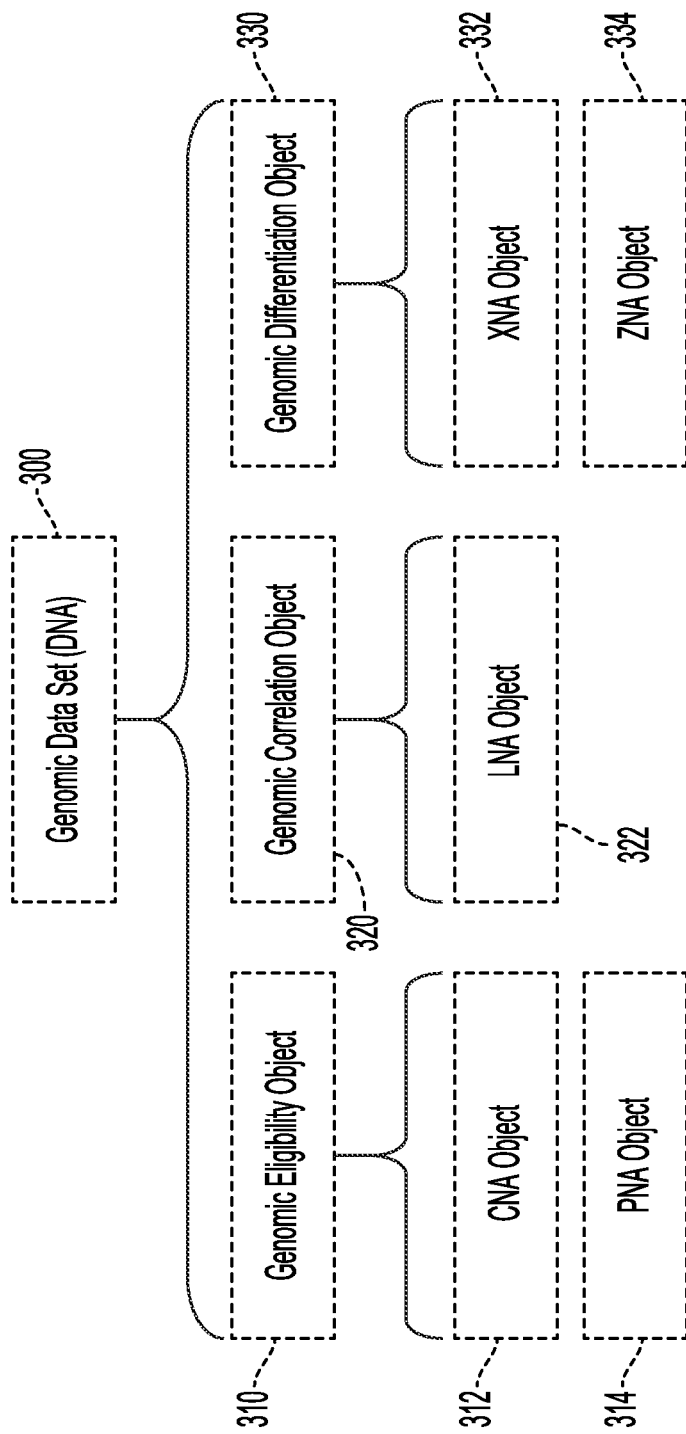
FIG. 5 illustrates example implementations of genomic data sets, in accordance with some embodiments of the present disclosure.

FIG. 5 illustrates example implementations of genomic data sets 300 (which are also referred to as a "digital DNA sets", "DNA sets" or "DNA"). As discussed, in embodiments a CG-ESP (e.g., CG-ESP 400) is configured with a set of CG-processes and related computational methods that operate on specific genomic data sets. FIG. 3 illustrates examples of different types of genomic data that may be implemented with respect to different CG-ESPs. It is appreciated that other types of genomic data may be later developed.

In embodiments, a DNA set 300 that is used in connection with a CG-ESP may include one or more different types of digitally generated mathematical objects that exhibit configurable entropy (instances of which may be generically referred to as "genomic data" or "DNA objects"). In some embodiments, the digitally generated mathematical objects of a DNA set may include any suitable combination of a genomic eligibility object 310, a genomic correlation object 320, and/or a genomic differentiation object 330. As will be discussed, different implementations of a respective CG-ESPs may utilize and support different combinations, types, and sizes of genomic data objects depending on the goals of respective community owners and/or the types of ecosystem that the respective platform instances support. Examples of different goals may include performance and efficiency goals, security goals, resource allocation goals (e.g., memory, storage, processing power, network bandwidth, etc.), economic goals, and the like. Furthermore, certain types of ecosystems have different constraints or advantages. For example, certain controlled ecosystems (e.g., some executable ecosystems) may only require certain cohorts (e.g., dependent cohorts such as applications, sensors, device drivers, processors, memory devices, or the like) to establish a very limited number of relationships (e.g., via links). In these scenarios, links for each respective relationship in the ecosystem may be generated at the time the ecosystem is created, such that each VDAX may have access to any and all links that will be needed. In such scenarios, a DNA set may not derive any additional benefit from having certain types of DNA objects, such that the DNA sets for such an ecosystem may be configured without a genomic eligibility object 310 or a genomic correlation object 320 but may include a genomic differentiation object 330. In another example scenario, the implementations two or more of engagement eligibility determination, link exchange, and/or differentiation/VBLS generation may be performed using a single DNA object (e.g., via a unique intersection of the respective DNA object of a respective pair of VDAXs that is used for engagement eligibility validation, link exchange, and VBLS determination). In this example, the community owner may wish to sacrifice additional security measures to reduce storage requirements associated with storing disparate types of genomic data objects. In other scenarios, a community owner can control the amount of entropy exhibited in each type of DNA object in a DNA set based on the type of data structure that is selected and/or the size of the data structure. For instance, genomic differentiation objects 330 that are implemented as 512×512-bit binary vectors or bit matrices may provide quantum proof levels of security.

In embodiments of the present disclosure, genomic eligibility objects 310 may refer to digitally generated mathematical objects that allow a pair of cohorts to confirm engagement eligibility, which may be performed in part of a "trustless" authentication process between two cohorts. In embodiments, a progenitor VDAX (e.g., an ecosystem VDAX or an enclave VDAX) may derive progeny genomic eligibility objects 310 for progeny VDAXs that are to join a respective digital ecosystem based on its genomic eligibility object (a "progenitor genomic eligibility object"). In these embodiments, each progeny VDAX may receive a unique but correlated derivation of the progenitor genomic eligibility object. Furthermore, in some implementations, all the genomic eligibility objects of an ecosystem may be derived from a progenitor genomic eligibility object, such that any member of an ecosystem can confirm some relationship to other ecosystem members based on their correlated genomic eligibility objects (e.g., intersecting or shared portions of the progenitor genomic eligibility object). Upon being assigned a genomic eligibility object for a particular community, a progeny VDAX may receive its genomic eligibility object. In some embodiments, a progeny VDAX may receive its genomic eligibility object in its genomic data set via a one-time trusted event (e.g., upon admission to a particular enclave, when a device is manufactured, configured, or sold, or the like). After receiving their respective genomic correlation objects 310, VDAXs can independently confirm engagement eligibility with one other VDAXs in their enclave and/or ecosystem using their respective genomic eligibility objects 310. In embodiments, the genomic correlation objects 310 for a particular CG-enabled digital ecosystem may be selected from CNA objects 312, PNA objects 314, and/or other suitable mathematical constructions that allow two community members to confirm engagement eligibility and/or engagement integrity.

In embodiments, CNA may refer to genomic mathematical constructions that allow a VDAX to uniquely determine that another VDAX is part of the same ecosystem community. In embodiments, this ecosystem correlation may be rendered computationally quantum proof. In embodiments, VDAX-performed ecosystem correlation is based on common computationally complex genomic functions, which may be performed without any form of consultation with a central authority (e.g., trusted third-party). These correlation attributes enable two VDAXs in the same ecosystem activated years apart to confirm their ecosystem status without any prior knowledge of the other and without any consultation with a trusted third-party.

In embodiments, CNA objects 312 may be implemented as binary vectors, binary matrices, or the like. In embodiments, CNA objects 312 are configured to exhibit specific entropy. In some embodiments, the entropy of an ecosystem's CNA is controllable entropy, whereby the entropy may be configured by, for example, a community owner. In some implementations, a configurable level of entropy of a CNA object 312 may be a substantially quantum-proof level of entropy. For instance, substantially quantum-proof CNA objects may be configured to exhibit a level of entropy that is greater than or equal to 256-bit of entropy. For example, in some embodiments, such levels of entropy may be achieved by CNA objects implemented as 512×512-bit binary vector or binary matrix. It is appreciated that quantum-proof CNA objects 312 may exhibit less entropy in some example implementations. It is appreciated that CNA objects 312 exhibiting less entropy may be used, (e.g., determined by the community owner or any other party configurating a security platform). For example, a community owner may wish to comply with jurisdictional regulations and thusly may use CNA objects (or other genomic data sets) that exhibit lower levels of entropy, which comes at the cost of overall security but requiring less storage and processing demands. In embodiments, CNA 312 may be configured to establish specific relationships between individual ecosystem members and confirm eligibility for engagement using a set of genomic processes and related computational methods.

In embodiments, CNA generation for genomic eligibility-correlation applications results in large sets of random data which can be organized as specific binary vectors. In some embodiments, CNA generation for genomic eligibly-correlation applications may be enabled by high quality random processes, having controllable entropy. In embodiments, CNA generation for genomic eligibility-correlation applications may be enabled on a specific mathematical basis, having controllable entropy. In embodiments, CNA may be generated in accordance with a wide range of information theory-facilitated complex functions. In embodiments, these information theory-facilitated functions may be cypher-based, cipherless, or hybrid computationally complex functions. Example techniques for generating CNA objects, modifying CNA objects, and confirming eligibility for engagement are discussed in greater detail throughout the disclosure.

In embodiments, PNA may refer to a digital that allow a VDAX to uniquely determine that another VDAX is part of the same ecosystem community. In embodiments, this ecosystem correlation may be rendered computationally quantum proof. In embodiments, VDAX-performed ecosystem correlation is based on common computationally complex genomic functions, which may be performed without any form of consultation with a central authority (e.g., trusted third-party). These correlation attributes enable two VDAXs in the same ecosystem activated years apart to confirm their ecosystem status without any prior knowledge of the other and without any consultation with a trusted third-party.

In embodiments, PNA objects 314 may be implemented as a set of binary primitive polynomials or the like. In embodiments, PNA objects 314 are configured to exhibit specific entropy. In some embodiments, the entropy of an ecosystem's PNA objects 314 is controllable entropy, whereby the entropy may be configured by, for example, a community owner. In some implementations, a configurable level of entropy of a PNA object 314 may be a substantially quantum-proof level of entropy. For instance, substantially quantum-proof PNA objects 314 may be configured to exhibit a level of entropy that is greater than or equal to 256 bits of entropy. For example, in some embodiments, such levels of entropy may be achieved by PNA objects implemented as two different sets (e.g., a first vector representing a 2048×2048 bit binary matrix and a second vector representing a set of $2^{16}$ randomly chosen binary primitive polynomials of degree 256). It is appreciated that quantum-proof PNA objects 314 may exhibit less entropy in some example implementations. It is appreciated that PNA objects 314 having less entropy may be used (e.g., as determined by the community owner or any other party configurating a security platform). For example, a community owner may wish to comply with jurisdictional regulations and thusly may use PNA objects (or other genomic data sets) that exhibit lower levels of entropy, which comes at the cost of overall security but requiring less storage and processing demands. In embodiments, PNA may be configured to establish specific relationships between individual ecosystem members and confirm eligibility for engagement using a set of genomic processes and related computational methods.

In embodiments, PNA generation for genomic eligibility-synchronization applications results in large sets of random data which can be organized as specific binary vectors. In some embodiments, PNA generation for genomic eligibly-correlation applications may be enabled by high quality random processes, having controllable entropy. In embodiments, PNA generation for genomic eligibility—eligibility-synchronization applications may be enabled on a specific mathematical basis, having controllable entropy. Example techniques for generating PNA objects, modifying PNA objects, and confirming eligibility for engagement are discussed in greater detail throughout the disclosure. Example techniques for generating PNA objects, modifying PNA objects, and confirming eligibility for engagement are discussed in greater detail throughout the disclosure.

In embodiments, genomic correlation objects 320 may refer to digitally generated mathematical objects that enable VDAXs to establish correlation with one another. In embodiments, genomic correlation objects enable link exchange between VDAXs, whereby a first VDAX may spawn a link (also referred to as a "link") that is provided to and hosted by a second VDAX, whereby the link provides instructions that the second VDAX uses to generate VBLS that only the first cohort can decode (assuming that the link is safely held by the second VDAX). In embodiments, the genomic correlation objects 310 used in a CG-ESP to confirm link exchange correlation, which allows two ecosystem components (e.g., enclave VDAX, cohort VDAXs, and the like) to establish a specific relationship and engage one another.

In example implementations of a CG-ESP, the genomic correlation objects 320 of the community members of a digital ecosystem are implemented as LNA objects 322. In some embodiments, LNA is a core competence on which genomic correlation functions rely. In embodiments, LNA forms the basis by which VDAXs establish correlation with one another. The entropy that LNA objects 312 exhibits is critical in terms of the quality of correlation. The non-recurring correlation attributes that may be derived from specific computationally complex genomic functions. In some implementations of a CG-ESP, LNA may be generated (e.g., by an ecosystem VDAX) for genomic correlation applications in large sets of random data. In some embodiments, LNA objects 322 are implemented as binary vectors, bit matrices, or other suitable structures. In embodiments, LNA objects 322 are configured to exhibit configurable entropy, such that the level of entropy which an LNA object exhibits may be a factor in the overall degree of the correlation. In embodiments, LNA generation may be performed by high-quality random processes, having controllable entropy. In some embodiments, LNA generation for genomic correlation applications may be enabled on a specific mathematical basis, having controllable entropy. In embodiments, LNA may be generated in accordance with a wide range of information theory-facilitated complex functions. In embodiments, these information theory-facilitated functions may be cypher-based, cipherless, or hybrid computationally complex functions.

In embodiments, a pair of VDAXs can engage in di-symmetric link exchange and/or one-way link exchange based on their common LNA (e.g., both VDAXs were assigned their respective LNA from the same progenitor). In embodiments, a first VDAX may modify its LNA object and may encode genomic regulation instructions ("GRI") based on the modified LNA, such that the second cohort is the only other VDAX that able to decode the mapped GRI. In embodiments, GRI may include data (e.g., one or more values) and instructions indicating a manner by which the data is used to differentiate the pair of VDAXs for data exchange. In embodiments, the GRI may be used to modify a differentiation object, such that the data included in the GRI may include a differentiation value (e.g., embodied as a binary vector) that is used as an input parameter to an information theory-facilitated computationally complex function that modifies the genomic differentiation object based on the differentiation value. In some embodiments, the GRI may include a sequence modification value that is used during the sequence mapping process. In these embodiments, the sequence mapping process may be used as an input parameter to an information theory-facilitated computationally complex function that modifies a sequence into an intermediate value based on the differentiation value, such that the intermediate value and a modified differentiation object are used as input values into an information theory-facilitated computationally complex function that outputs a genomic engagement value corresponding to the original sequence.

It is appreciated that encoding the genomic regulation instructions based on the modified LNA may include intermediate operations. For example, in some implementations of CG-ESP, a VDAX may be configured to determine a mapping sequence, map the mapping sequence into the modified LNA using a computationally complex function, and encode the GRI based on the genomic engagement factor. In these example implementations, the VDAX may provide the link to the other VDAX, such that the other VDAX can successfully decode the encoded GRI if the other VDAX possesses highly correlated LNA. In some implementations of a CG-ESP, the LNA objects of the VDAXs may be highly correlated if they are identical or otherwise sufficiently correlated. In some embodiments, link exchange is a one-time process, such that link exchange is only performed once between a pair of cohorts, unless one of the cohorts explicitly updates its respective link to modify the GRI. Outside of such action, a pair of cohorts can continue to exchange data based on the respective links generated by each of the cohorts, even in some scenarios where the LNA objects of the respective VDAXs are mutated (e.g., persistently modified) by or at the instruction of, for example, a progenitor VDAX after successful link exchange. Examples of genomic operations involving LNA objects 322 are discussed in greater detail throughout the disclosure, including techniques for generating LNA objects 322, modifying LNA objects 322, and performing link exchange using LNA objects 322 are discussed in greater detail throughout the disclosure.

In embodiments of the present disclosure, genomic differentiation objects 330 may refer to digitally generated mathematical objects that allow a pair of community members (e.g., cohorts) to exchange and decode VBLS generated by the pair of community members, provided the pair of community members have successfully exchanged links and have sufficiently correlated genomic differentiation objects. In some embodiments, a first VDAX generates VBLS for a second VDAX in part by modifying its genomic differentiation object 330 in the manner defined in the genomic regulation instructions (GRI) provided to the first VDAX in a link from the second VDAX, and decodes VBLS from the second cohort in part by modifying its genomic differentiation object 330 in accordance with the GRI that were provided to the second cohort. In embodiments of the CG-ESP, the first VDAX may map a sequence (e.g., a private or public sequence) into the modified XNA object using a computationally complex function (e.g., cipher-based, cipherless, or hybrid computationally complex functions) to obtain a genomic engagement factor, which may then be used to encode a digital object. Examples of genomic differentiation objects 330 may include, but are not limited to, XNA 332 objects and ZNA 334 objects.

In example implementations, the genomic differentiation objects 330 of the community members of a digital ecosystem are XNA. In some embodiments, XNA is a core competence on which all genomic differences rely. In these embodiments, XNA forms the basis by which di-symmetric languages (e.g., VBLS) that VDAXs employ to control unique non-recurring engagement. In some embodiments, the unique non-recurring engagements may be quantum-proof. In embodiments, the entropy that XNA exhibits may be critical in terms of the security of VBLS, where higher entropy provides greater levels of security. In embodiments, the recurring difference attributes are derived from specific computationally complex genomic functions. In embodiments, XNA generation for genomic differentiation applications result in large sets of random data which can be organized as specific binary vectors. In embodiments, XNA generation for genomic differentiation applications may be performed by high-quality random processes, having controllable entropy. In some embodiments, XNA generation for genomic differentiation applications may be enabled on a specific mathematical basis, having controllable entropy. In embodiments, XNA may be generated in accordance with a wide range of information theory-facilitated complex functions. In embodiments, these information theory-facilitated functions may be cypher-based, cipherless, or hybrid computationally complex functions.

In some embodiments, an XNA object 332 may be implemented as a binary vector, matrix, or the like that exhibits configurable entropy. In some embodiments, the entropy which an XNA object 332 exhibits determines the security of the VBLS that is generated by a community member. In embodiments, the XNA that is assigned to respective community members (e.g., enclave members) from a progenitor VDAX is either identical and/or otherwise sufficiently correlated. In some embodiments, a first VDAX generating VBLS for a second VDAX modifies its XNA object 332 in accordance with the GRI provided by the second VDAX in a link. The first VDAX may then map a sequence (e.g., a public or private sequence) that is determinable by the second VDAX into the modified XNA object 332 to obtain a genomic engagement factor. A digital object (e.g., a processor instruction, a packet payload, a disk sector, or the like) may then be encoded using a cipher-based encryption or disambiguation and the genomic engagement factor to obtain the encoded digital object that is included in a VBLS object. In embodiments, the VBLS object may further include metadata, such as a sequence that was used to generate the genomic engagement factor. The VBLS resultant encoded digital object may then be provided to the second cohort. In these example implementations, the second cohort receives a VBLS object and modifies its XNA 332 in accordance with the GRI contained in the link that was provided by (or on behalf of) the second VDAX to the first VDAX and then maps the sequence into the modified XNA to recreate the genomic engagement factor. The genomic engagement factor may then be used to decode the encoded digital object to obtain a decoded digital object using the cipher-based decryption or disambiguation that was used to encode the digital object. In these example implementations, the ability for the VDAXs to both modify their respective XNA objects 332 using the same GRI and determine the genomic engagement factor in a deterministic manner allows the first cohort to securely provide the data object to the second VDAX and to potentially vary the genomic engagement factor for each instance of data exchange (e.g., every packet, every sector, every shard, every frame, or the like). In this way, VBLS may provide quantum proof levels of security. It is noted that the foregoing discussion is an example of how XNA or other genomic differentiation objects may be leveraged in a secure data exchange process.

In some embodiments, revocation of a community member (e.g., a cohort) from a community (e.g., an enclave) may be achieved by selectively mutating the XNA objects of some of the community members in the community by a progenitor VDAX. It is noted that "mutating" an XNA object may refer to providing instructions to a progeny VDAX to persistently modify its XNA object or providing a new XNA object to the progeny VDAX. In this way, the mutated XNA is used for subsequent VBLS coding and encoding with respect to the particular community. For example, in some example implementations, an ecosystem VDAX may mutate the XNA of only the cohorts that are to remain in an enclave. In this way, cohorts that have been revoked from the enclave can still attempt to engage with cohorts but will be unable to generate VBLS for or decode VBLS from cohorts that have a mutated XNA object. Should the community owner (e.g., a network administrator associated with the ecosystem and/or an enclave of the ecosystem) opt to reinstate the cohort, the enclave VDAX may mutate the XNA of the cohort to have sufficiently correlated XNA with the other community members whose XNA was previously mutated, such that the cohort can then commence exchanging data with other cohorts in the enclave using their previously established links and/or links established in the future.

In example implementations, the genomic differentiation objects 330 of the community members of a digital ecosystem are ZNA. In some embodiments, ZNA is a core competence on which all executable isolation components genomic differences rely. In these embodiments, ZNA forms the basis by which unique, non-recurring (potentially quantum proof) executable binaries are controlled. EIC recurring transformations may be derived from specific computationally complex genomic functions. In embodiments, ZNA generation for genomic differentiation applications result in large sets of random data which can be organized as specific binary vectors. In embodiments, ZNA generation for genomic differentiation applications may be performed by high-quality random processes, having controllable entropy. In some embodiments, ZNA generation for genomic differentiation applications may be enabled on a specific mathematical basis, having controllable entropy. In embodiments, ZNA may be generated in accordance with a wide range of information theory-facilitated complex functions. In embodiments, these information theory-facilitated functions may be cypher-based, cipherless, or hybrid computationally complex functions.

In some embodiments, a ZNA object 334 may be implemented as a binary vector, matrix, or the like, whereby ZNA objects 334 exhibit configurable entropy. In some embodiments, ZNA may be structurally similar to XNA but is used in executable ecosystems. In embodiments, ZNA may be used to generate VBLS that is exchanged between components of an executable ecosystem. In some embodiments, the entropy which an ZNA object 334 exhibits determines the security of the VBLS that is generated by a community member. In embodiments, the ZNA that is assigned to respective community members (e.g., device components) from a progenitor VDAX is either identical and/or otherwise sufficiently correlated. In some embodiments, a first VDAX (e.g., a first EIC) generating VBLS for a second VDAX (e.g., a second EIC) modifies its ZNA object 334 in accordance with the GRI provided by the second VDAX in a link. The first VDAX may then map a sequence (e.g., a public or private sequence) that is determinable by the second VDAX into the modified ZNA object 334 to obtain a genomic engagement factor. A digital object (e.g., a processor instruction, a disk sector, or the like) may then be encoded using a complex function and the genomic engagement factor to obtain the encoded digital object that is included in a VBLS object. In embodiments, a VBLS object may further include metadata, such as a sequence that was used to generate the genomic engagement factor. The VBLS resultant encoded digital object may then be provided to the second VDAX. In these example implementations, the second VDAX receives a VBLS object and modifies its ZNA object 334 in accordance with the GRI contained in the link that was provided on behalf of the second VDAX to the first VDAX and maps the sequence into the modified ZNA object 334 to recreate the genomic engagement factor. The genomic engagement factor may then be used to decode the encoded digital object to obtain a decoded digital object using the inverse of the two-way function that was used to encode the digital object. In these example implementations, the ability for the VDAXs to both modify their respective ZNA objects 334 using the same GRI and determine the genomic engagement factor in a deterministic manner allows the first cohort to securely provide the data object to the second VDAX and to potentially vary the genomic engagement factor for each instance of data exchange (e.g., every packet, every sector, every shard, every frame, or the like). In this way, VBLS may provide quantum proof levels of security. It is noted that the foregoing discussion is an example of how ZNA or other genomic differentiation objects may be leveraged in a secure data exchange process.

As can be appreciated from the disclosure, the core genomic competences (e.g., differentiation and correlation that support CG-ESP processes) rely upon generation (e.g., DNA generation that may include LNA generation, XNA generation, ZNA generation, CNA generation, and/or PNA generation), modification (e.g., DNA modification that may include LNA modification, XNA modification, ZNA modification, CNA modification, and/or PNA modification), and allocation (e.g., DNA allocation that may include LNA allocation, XNA allocation, ZNA allocation, CNA allocation, and/or PNA allocation) of specific genomic (e.g., digital DNA that may include some combination of LNA, XNA, ZNA, CNA, and/or PNA). In embodiments, these application specific DNA constructions (e.g., some combination of LNA, XNA, CNA, PNA, and/or ZNA) have specific transformations and are critical to the controllable virtualization of differentiation.

In embodiments, an ecosystem progenitor (e.g., ecosystem VDAX) may mutate (e.g., persistently modify) the genomic data 300 of some or all of the ecosystem members. In embodiments, mutation of genomic data 300 may refer to persistent modification or updating of a genomic data object. For example, in embodiments, an ecosystem may mutate the LNA objects 322, XNA objects 332, CNA objects 312, and/or PNA objects 314 of some or all of the ecosystem members, such that VDAXs will use the mutated genomic data in place of the previous genomic data. It is noted that the term "mutation" may be used to refer to modifications to DNA objects 300 that are persistent, as opposed to modification during link exchange or VBLS generation, which may be transient modification. It is noted, however, that modification and mutation may have similar effects to a DNA construction, and that the term "modification" may be used in connection with persistent modifications when context so suggests.

In embodiments, the LNA objects of community members may be modified (e.g., for link exchange) and mutated (e.g., persistently modified/updated). As discussed, non-recurring correlation objects (e.g., LNA) may be derived from specific computationally complex genomic functions, which correlation may involve digital ecosystems having dimension N×M, comprised of VDAXs having various enclave relationships N×Ma. Such digital ecosystem relationships may require modification of their correlation attributes, to prevent establishment of future or additional ecosystem relationships. Mutation of LNA enables specific (broad and narrow) redetermination of correlation attributes. In embodiments, LNA genomic constructions may be tailored to specific digital ecosystem organizations, which constructions are modifiable. In some embodiments, LNA random vectors can be uniformly or discreetly (broadly and narrowly) modified on the basis of specific instructions. LNA modifications preserve the genomic integrity of the LNA construction, and its correlation attributes. In embodiments, VDAXs in possession of modified LNA are unable to affect future correlation with VDAXs in possession of non-modified LNA. In embodiments, LNA may be genomically modified in accordance with a wide range of Information theory-facilitated cryptographic computationally complex functions. In embodiments, these information theory-facilitated functions may be cypher-based, cipherless, or hybrid computationally complex functions.

In embodiments, the XNA of community members may be mutated (e.g., persistently modified/updated). As discussed, non-recurring differentiation objects (e.g., XNA) may be derived from specific computationally complex genomic functions, which differentiation may involve digital ecosystems having dimension N×M, comprised of VDAXs having various enclave relationships N×Ma. Such digital ecosystem relationships may require modification of their differentiation attributes, one of the most challenging problems in security management (e.g., relationship revocation). Mutation of XNA enables specific (broad and narrow) redetermination of differentiation attributes, efficiently resolving the relationship revocation challenge. In embodiments, XNA genomic constructions may be tailored to specific digital ecosystem organizations, which constructions are modifiable. In some embodiments, XNA random vectors can be uniformly or discreetly (broadly and narrowly) modified on the basis of specific instructions. XNA modifications preserve the genomic integrity of the XNA construction, and its correlation attributes. In embodiments, VDAXs in possession of mutated XNA are unable to affect future differentiation with VDAX in possession of non-mutated XNA. In embodiments, XNA may be genomically mutated in accordance with a wide range of Information theory-facilitated cryptographic computationally complex functions. In embodiments, these information theory-facilitated functions may be cypher-based, cipherless, or hybrid computationally complex functions.

In embodiments, the CNA objects 312 of community members may be mutated (e.g., persistently modified/updated). As discussed, non-recurring eligibility objects (e.g., CNA or PNA) may be derived from specific computationally complex genomic functions, which modification may involve digital ecosystems having dimension N×M, comprised of VDAXs having various enclave relationships N×Ma. Such digital ecosystem relationships may require modification of their differentiation attributes, one of the most challenging problems in security management (e.g., relationship revocation). Modification of VDAX ecosystem eligibility objects preserves common computationally complex genomic functions. Such digital ecosystem relationships may require modification of their eligibility objects, preventing VDAXs from establishing future or additional ecosystem relationships. Mutation of CNA or PNA enables specific (broad and narrow) redetermination of eligibility objects.

In embodiments, CNA genomic constructions may be tailored to specific digital ecosystem organizations, which constructions are modifiable. In some embodiments, CNA random vectors can be uniformly or discreetly (broadly and narrowly) modified on the basis of specific instructions. CNA modifications preserve the genomic integrity of the CNA construction, and its eligibility-correlation attributes. In embodiments, VDAXs in possession of mutated CNA are unable to establish future eligibility-correlation with VDAXs in non-mutated CNA. In embodiments, CNA may be genomically mutated in accordance with a wide range of information theory-facilitated computationally complex functions. In embodiments, these information theory-facilitated functions may be cypher-based, cipherless, or hybrid computationally complex functions.

In embodiments, PNA genomic constructions may be tailored to specific digital ecosystem organizations, which constructions are modifiable. In some embodiments, PNA random primitive polynomials can be uniformly or discreetly (broadly and narrowly) modified on the basis of specific instructions. PNA modifications preserve the genomic integrity of the PNA construction, and its eligibility-synchronization attributes. In embodiments, VDAXs in possession of mutated PNA are unable to establish future eligibility-synchronization with VDAXs in non-mutated PNA. In embodiments, PNA may be genomically mutated in accordance with a wide range of information theory-facilitated computationally complex functions.

In embodiments, an ecosystem progenitor (e.g., an ecosystem VDAX) may allocate DNA to community members (e.g., enclaves, cohorts, and the like). In embodiments, each of the specific DNA constructions has unique genomic relationships. LNA provides for correlation, XNA for differentiation, CNA for engagement-integrity, and PNA for engagement-eligibility. The overall capabilities facilitated by these constructions derive substantially from the relationship of their genomic mathematical constructions, and finally their specific VDAX allocation. These VDAX relationships may be modified in accordance with the specific modification of the DNA (e.g., LNA, XNA, CNA, and PNA).

In embodiments, an ecosystem progenitor (or a suitable progenitor VDAX) may allocate LNA to community members. In embodiments, LNA correlation capabilities are germane to all digital ecosystems having dimension N×M, comprised of VDAXs, which may also have various enclave and cohort relationships N×Ma. In embodiments, LNA genomic based constructions are allocated to specific digital ecosystem VDAXs (e.g., ecosystem VDAX, enclave VDAX, cohort VDAX, and/or dependent VDAX), and determine their related correlation capabilities. In embodiments, LNA allocation preserves the genomic integrity of the LNA construction, and its correlation attributes. In embodiments, VDAXs (e.g., ecosystem VDAX, enclave VDAX, cohort VDAX, and the like) whose initial LNA allocation is modified are no longer able to affect correlation with VDAXs in possession of non-modified LNA may now be able to affect future correlation with other VDAXs having the same modified LNA allocation. In embodiments, LNA may be genomically allocated in accordance with a wide range of Information theory-facilitated computationally complex functions. In embodiments, these information theory-facilitated functions may be cypher-based, cipherless, or hybrid computationally complex functions.

In embodiments, an ecosystem progenitor (or a suitable progenitor VDAX) may allocate XNA to community members. In embodiments, XNA differentiation capabilities are germane to all digital ecosystems having dimension N×M, comprised of VDAXs (e.g., ecosystem VDAX, enclave VDAX, cohort VDAX, and/or dependent VDAX), which may also have various enclave and cohort relationships N×Ma. In embodiments, XNA genomic based constructions are allocated to specific digital ecosystem VDAXs (e.g., ecosystem VDAX, enclave VDAX, cohort VDAX, and/or dependent VDAX), and determine their related differentiation capabilities. In embodiments, XNA allocation preserves the genomic integrity of the XNA construction, and its differentiation attributes. In some embodiments, VDAX (e.g., ecosystem VDAX, enclave VDAX, cohort VDAX, and the like) whose initial XNA allocation is modified are no longer able to affect differentiation with VDAXs in possession of non-modified XNA may now be able to affect differentiation with other VDAX having the same modified XNA allocation. In embodiments, XNA may be genomically allocated in accordance with a wide range of Information theory-facilitated computationally complex functions. In embodiments, these information theory-facilitated functions may be cypher-based, cipherless, or hybrid computationally complex functions.

In embodiments, an ecosystem progenitor (or a suitable progenitor VDAX) may allocate CNA to community members. In embodiments, CNA engagement-integrity capabilities are germane to all digital ecosystems having dimension N×M, comprised of VDAXs (e.g., ecosystem VDAX, enclave VDAX, cohort VDAX, and/or dependent VDAX), which may also have various enclave and cohort relationships N×Ma. In embodiments, CNA genomic based constructions are allocated to specific digital ecosystem VDAXs (e.g., ecosystem VDAX, enclave VDAX, cohort VDAX, and/or dependent VDAX). In embodiments, these CNA genomic-based constructions determine their related engagement-integrity capabilities within an ecosystem. In some embodiments, CNA genomic based constructions allocated to specific digital ecosystem VDAXs may also be unique.

In embodiments, CNA allocation preserves the genomic integrity of the CNA construction, and its engagement-integrity attributes. In some embodiments, VDAXs (e.g., ecosystem VDAX, enclave VDAX, cohort VDAX, and the like) whose initial CNA allocation is modified are no longer able to affect engagement-integrity with VDAXs in possession of non-modified CNA and may now be able to affect engagement-integrity with other VDAX having the same modified CNA allocation. In embodiments, CNA may be genomically allocated in accordance with a wide range of Information theory-facilitated computationally complex functions. In embodiments, these information theory-facilitated functions may be cypher-based, cipherless, or hybrid computationally complex functions.

In embodiments, an ecosystem progenitor (or a suitable progenitor VDAX) may allocate PNA to community members. In embodiments, PNA engagement-eligibility capabilities are germane to all digital ecosystems having dimension N×M, comprised of VDAXs (e.g., ecosystem VDAX, enclave VDAX, cohort VDAX, and/or dependent VDAX), which may also have various enclave and cohort relationships N×Ma. In embodiments, PNA genomic based constructions are allocated to specific digital ecosystem VDAX (e.g., ecosystem VDAX, enclave VDAX, cohort VDAX, and/or dependent VDAX), and determine their related engagement-eligibility capabilities. In embodiments, PNA genomic based constructions allocated to specific digital ecosystem VDAXs may also be unique.

In embodiments, PNA allocation preserves the genomic integrity of the PNA construction, and its engagement-eligibility attributes. VDAX (e.g., ecosystem VDAX, enclave VDAX, cohort VDAX, and the like) whose initial PNA allocation is modified are no longer able to affect engagement-eligibility with VDAX in possession of non-modified PNA and may now be able to affect engagement-eligibility with other VDAX having the same modified PNA allocation. In embodiments, PNA may be genomically allocated to VDAXs in accordance with a wide range of Information theory-facilitated computationally complex functions. In embodiments, these information theory-facilitated functions may be cypher-based, cipherless, or hybrid computationally complex functions.

As discussed, a pair of sufficiently correlated VDAXs may engage using links. In embodiments, a main purpose of links is to enable exchange of information necessary for a pair of VDAXs to perform higher level computationally complex genomic functions. In embodiments, the information exchanged in a link is referred to as genomic-engagement-cargo (GEC). In embodiments, link processes may include link spawning, link hosting, and link updating. Link spawning may refer to the generation and transport of a link by a spawning VDAX. Link hosting may refer to the acquisition and integration of the information contained in a link by a recipient VDAX. Link updating may refer to a CG-process where a VDAX may modify the genomic basis used to engage with another VDAX. The process of link updating may also be referred to as "link modification". In embodiments, the link processes (spawning, hosting, updating) rely upon specific information theory constructions. For example, in embodiments, LNA may be used as a basis for genomic correlation, CNA may be used as a basis for genomic engagement-integrity, and PNA may be used as a basis for genomic engagement-eligibility). These DNA constructions (e.g., LNA, CNA, and PNA) are application specific genomic constructions, which enable specific genomic transformation functions that facilitate the link processes. In embodiments, the link processes may be defined in a link module 430 of a CG-ESP, whereby some or all of the CG-ESP instances may be configured with link process module 430 instances that perform these functions. For example, any VDAX whose role requires to spawn, host, and/or update links may be configured with such link process modules 430 instances, which may define processes for static links and/or dynamic links.

In embodiments, a pair of VDAXs (e.g., a first VDAX and a second VDAX) that belong to the same CG-enabled digital ecosystem may spawn and host links without any prior arrangement. In these embodiments, a VDAX (e.g., a first VDAX) intending to spawn a genomic link for reception and use of genomic engagement cargo (GEC) by another VDAX (e.g., second VDAX) utilizes its CNA to establish engagement-integrity with the other VDAX (e.g., second VDAX) for which the link was generated. In some embodiments, a VDAX (e.g., first VDAX) spawns a genomic link for reception and use of the contained GEC by another VDAX (e.g., second VDAX), whereby the pair of VDAXs (e.g., the first and second VDAXs) may have multiple genomic links that utilize the same CNA to establish engagement-integrity.

In embodiments, the VDAX (e.g., first VDAX) intending to spawn a genomic link for reception and use of GEC by another VDAX (e.g., second VDAX) may utilize its PNA to establish engagement-eligibility with the other VDAX for which the link was generated. In some embodiments, a VDAX (e.g., first VDAX) spawns a genomic link for reception and use of the contained GEC by another VDAX (e.g., second VDAX), whereby the pair of VDAXs (e.g., the first and second VDAXs) may have multiple genomic links that utilize the same PNA to establish engagement-eligibility. It is noted that in some embodiments, the GEC contained in a link may include additional link activation requirements.

In some embodiments, a spawning VDAX that is spawning a link for transmission and use (e.g., "link hosting") by another VDAX (e.g., second VDAX) may utilize its LNA to establish genomic correlation with the other VDAX for which the link was generated. As discussed, LNA-based genomic processes may enable an entire digital ecosystem (community) to achieve VDAX to VDAX correlation based on a single genomic construction (e.g., LNA). In embodiments, LNA-based genomic processes enable a VDAX to modify its respective LNA construction by using specific computationally complex functions, whereby these LNA-based genomic processes exploit sub-constructions of genomic information (e.g., LNA-based genomic sub-constructions). In embodiments, LNA-based genomic sub-constructions may be utilized to compute unique transformation information by the link spawning VDAX that may be only reproduced by the link hosting VDAX, at the same level of entropy as underlying computationally complex genomic functions. In embodiments, the unique genomic engagement factor is utilized to prepare GEC for digital transport from the spawning VDAX to the hosting VDAX. In some of these embodiments, the link hosting VDAX may use the unique genomic engagement factor to decode encoded GRI contained in the GEC. In some embodiments, the unique genomic engagement factor may be rendered as multiple sub-constructions for application in multiple digital transport channels.

In some scenarios, ecosystem correlation is not available. In some embodiments, VDAX authentication may be necessary for link spawning and hosting when ecosystem correlation is not available. In these embodiments, VDAX authentication may be accomplished by use of alternate genomic sub-constructions to facilitate free-form-correlation (FFC). For example, a scenario may arise where a pair of VDAXs are in unique genomic digital ecosystems (which may be referred to as "republics"). In some embodiments, these unrelated VDAXs may form a unique genomic digital ecosystem (which may be referred to as a "federation") for specific operations and uses. In these embodiments, the VDAXs may spawn links as members of the federation as well as within their respective republics.

In embodiments, link spawning genomic processes may be carried out in accordance with a wide range of information theory-facilitated computationally complex functions which facilitate execution of genomic functions and processes. In embodiments, these information theory-facilitated functions may be cypher-based, cipherless, or hybrid computationally complex functions.

As mentioned, genomic link hosting (or "link hosting") may include acquisition and integration of link information by a VDAX (e.g., a second VDAX), such that a link contains specific genomic-engagement-cargo (GEC) from another VDAX (e.g., a first VDAX). In embodiments, link hosting may be performed in accordance with specific computationally complex genomic functions. In embodiments, a hosting VDAX (e.g., second VDAX) receives the unique transformation information sub-constructions via one or multiple digital transport channels. In embodiments, a hosting VDAX (e.g., a second VDAX) intending to use (host) genomic-engagement-cargo (GEC) transported by a link spawned by a spawning VDAX (e.g., first VDAX) may utilize its CNA to establish engagement-integrity with the spawning VDAX. In embodiments, a hosting VDAX (e.g., a second VDAX) intending to use (host) genomic-engagement-cargo (GEC) transported by a link spawned by a spawning VDAX (e.g., first VDAX) may utilize its PNA to establish engagement-eligibility with the spawning VDAX.

In embodiments, a hosting VDAX may leverage its digital ecosystem correlation-enabling LNA by modifying its LNA using specific computationally complex functions which exploit unique transformation information sub-constructions. In embodiments, LNA based genomic sub-constructions are utilized to compute unique genomic engagement factor by the link hosting VDAX, at the same level of entropy as underlying computationally complex genomic functions. In embodiments, the hosting VDAX (e.g., second VDAX) utilizes the unique genomic engagement factor to extract the GEC from a link provided by the spawning VDAX (e.g., first VDAX). In embodiments, the hosting VDAX (e.g., second VDAX) may be required to complete additional link activation requirements that are imposed by the spawning VDAX, whereby the additional link activation requirements are provided in the GEC.

As discussed, a scenario may arise where a pair of VDAXs are in unique genomic digital ecosystems (which may be referred to as "republics"). In some embodiments, these unrelated VDAXs may form a unique genomic digital ecosystem (which may be referred to as a "federation") for specific operations and may use, as discussed above.

In embodiments, link hosting genomic processes may be carried out in accordance with a wide range of information theory-facilitated computationally complex functions. In embodiments, these information theory-facilitated functions may be cypher-based, cipherless, or hybrid computationally complex functions. In embodiments, these functions may be necessary to perform the genomic operations.

In embodiments, VDAXs may update links hosted by other VDAXs. For example, to increase security levels, a VDAX may update a link hosted by another VDAX to decrease the possibility that a malicious party may determine or otherwise obtain the link information (e.g., GRI). In these embodiments, a pair of VDAXs (e.g., a first VDAX and a second VDAX) having previously completed "link spawning" and "link hosting" protocols, may update one or both links. In this way, a VDAX (e.g., the first VDAX) may modify the genomic basis used to engage with another VDAX (e.g., the second VDAX), and/or vice-versa. In some embodiments, a new genomic link spawned by a VDAX (e.g., first VDAX) and transmitted for hosting to another VDAX (e.g., second VDAX) may be used to replace one or more existing hosted links by the other VDAX with the newly spawned link, thereby updating the link. In embodiments, a genomic link spawned link by a VDAX and transmitted for hosting to another VDAX may be used to modify portions or all of the GRI data of an existing hosted link.

As discussed above, a scenario may arise where a pair of VDAXs are in unique genomic digital ecosystems (which may be referred to as "republics"). In some embodiments, these unrelated VDAXs may form a unique genomic digital ecosystem (or "federation") for specific operations and uses. In some of these embodiments, the federation of VDAXs may also update their links for the specific operations and uses.

In embodiments, link updating genomic processes may be carried out in accordance with a wide range of information theory-facilitated cryptographic computationally complex functions. In embodiments, these information theory-facilitated functions may be cypher-based, cipherless, or hybrid computationally complex functions, necessary to execute genomic functions and processes.

As discussed throughout the disclosure, sequence mapping and binary transformation are CG operations that may be performed to form VBLS. In embodiments, sequence mapping may be performed with public sequences and/or private sequences. In embodiments, a sequence may refer to a sequence of data (e.g., a sequence of bits). In embodiments, public sequences may refer to public protocol and format dependent information (e.g., TCP, UDP, TLS, HTTP, H.265, and the like), while private sequences may refer to private and/or proprietary protocol and format dependent information. In embodiments, sequences (e.g., public or private sequences) are computationally transformed into non-recurring values. While sequences may be broadly disparate (e.g., protocol independent and having preexisting entropy), sequences are processed in such a manner that results in values having specific levels of entropy. In embodiments, this process is compatible with a broad range of protocols and formats and may be initiated with different sequences exhibiting respective preexisting entropies. In embodiments, this process may be performed using complex genomic processes and functions that result in genomic engagement factor exhibiting specific levels of entropy.

In embodiments, CG-based security management systems and architectures may require the use of genomic engagement factors in conjunction with genomic data constructions. In embodiments, these genomic engagement factors may be derived in part by the use of recurring data (e.g., sequences). Prior to the use of sequences in conjunction with genomic data constructions, sequences are processed so the entropy of the resulting genomic engagement factors is consistent with that of the genomic construction (e.g., XNA). This process may be referred to as "sequence mapping" and its products are called genomic engagement factor. No matter that sequences may be broadly disparate, resultant genomic engagement factors exhibit a specific level of entropy. In embodiments, a genomic engagement factor may be produced from the integration of XNA Vectors. In some embodiments, multiple genomic engagement factors may be produced from a set of XNA vectors. In some embodiments, this process may be critical to the open architecture application which rely upon specific digital objects transformation, which objects potentially involve disparate protocols and formats (e.g., TCP, UDP, TLS, HTTP, H.265).

In some embodiments, broadly disparate external format and protocol resident data, without modification, is used to construct sequences. In some embodiments, broadly disparate external format and protocol resident data, with modification, is used to construct sequences. In some embodiments, sequences are used in conjunction with specific genomic based data constructions to determine unique vectors exhibiting specific entropy. In some embodiments, sequences are mapped in accordance with computationally complex genomic processes and functions in conjunction with specific genomic data constructions to derive a specific genomic engagement factor. In embodiments, sequence mapping results in a genomic engagement factors that exhibit entropy consistent with that of the genomic data construction, regardless of the inherent entropy of the sequence. In some embodiments, genomic engagement factors may be produced from sequence mapping that leverages internal CG-ESP formats and protocols in conjunction with these external formats and protocols. It is noted that genomic engagement factors should be determined in a manner that cannot be exploited to reveal format and protocol resident data and the genomic based construction (e.g., using computationally complex functions).

In embodiments, sequence mapping carries out the genomic engagement factor-generation genomic processes computed in accordance with information theory-facilitated computationally complex functions. In embodiments, these information theory-facilitated functions may be cypher-based, cipherless, or hybrid computationally complex functions, by which a sequence (public or private) and XNA produce a unique genomic engagement factor.

In some embodiments, a CG-ESP may implement genomic information theory-facilitated processes to facilitate hyper-scalable correlation. In embodiments, virtual authentication (e.g., unique correlation) of ecosystem, enclave, and cohort engagement relationships may be achieved with hyper-scalable correlation. As discussed, hyper-scalability technologies can be used to powerfully enhance ecosystem, enclave, and cohort engagements that depend on precise and unique correlation. As discussed, organic ecosystems (e.g., biological ecosystems) evidence powerful, although bounded, correlation across species, progeny, and siblings, which is derived from complex biochemical processes. The principles governing these biochemical processes may be reflected by specific digital genomic constructions facilitated by information theory, which exhibit unique correlation across ecosystems, enclaves, and cohorts. In embodiments, digital genomic correlation is practically unbounded and exhibits specific and user controllable entropy. In embodiments, genomic eligibility objects (e.g., CNA and/or PNA) and genomic correlation objects (e.g., LNA) may be used for digital genomic correlation.

In embodiments, ecosystem VDAXs may leverage computationally complex genomic processes to achieve virtual affiliation with enclaves and cohorts. Similarly, enclave VDAXs may use these computationally complex genomic processes to achieve hyper-scalable correlation with cohorts and cohort VDAXs may use the computationally complex genomic processes to achieve hyper-scalable correlation with other cohorts. In embodiments, unique hyper-scalable correlation between ecosystems, enclaves, and cohorts may be modified by computationally complex genomic processes. For example, an ecosystem VDAX may modify the LNA for a given enclave, so as to prevent future link exchange in that particular enclave for one or more of the enclave members. In some embodiments, enclave VDAXs and cohort VDAXs that are constituents of a given ecosystem may employ computationally complex genomic processes to correlate engagement with enclave VDAXs and cohort VDAXs that are constituents of other ecosystems. For example, in some embodiments, two ecosystem VDAXs may form a derived genomic data set from their respective genomic data sets, whereby members of the ecosystem may use the derived genomic data (or derivations thereof) to engage across ecosystems. In this way, enclave VDAXs and cohort VDAXs are capable of achieving unique hyper-scalable correlation across multiple ecosystems based on computationally complex genomic processes and their respective genomic data sets. In embodiments, hyper-scalable correlation carries out the genomic processes computed in accordance with a wide range of information theory-facilitated computationally complex functions, by which PNA, CNA, and LNA produce unique genomic engagement factors. These functions may be cipher-based, cipherless, or hybrid computationally complex functions.

In some embodiments, a CG-ESP may implement genomic information theory-facilitated processes to facilitate hyper-scalable differentiation. In some examples, hyper-scalable differentiation may be needed or may be required to provide unique affiliation between ecosystems, enclaves, and cohorts based on digital network-facilitated relationships. In embodiments, hyper-scalability technology can be used to powerfully enhance affiliation of ecosystems, enclaves, and cohorts that depends on precise and unique differentiation. Some example organic ecosystems may show evidence of powerful, although bounded, differentiation across species, progeny, and siblings that may be derived from complex bio-chemical processes. The principles governing these example bio-chemical processes may be reflected by specific digital genomic constructions governed by information theory, which may exhibit unique differentiation across ecosystems, enclaves, and cohorts. In some examples, this digital genomic differentiation may be practically unbounded and may exhibit specific and user controllable entropy.

There may be various example implementations for applying hyper-scalable differentiation in ecosystems, enclaves, and/or cohorts. For example, members of CG-enabled ecosystems may leverage computationally complex genomic processes to achieve hyper-scalable differentiation that facilitates unique non-recurring virtual affiliation between ecosystems, enclaves, and cohorts. In some examples, CG-enabled enclaves leverage computationally complex genomic processes to achieve hyper-scalable differentiation to facilitate unique non-recurring virtual affiliation between enclaves and cohorts. In some examples, cohorts may use computationally complex genomic processes to achieve hyper-scalable differentiation that facilitate unique non-recurring virtual affiliation between cohorts. In embodiments, unique hyper-scalable differentiation between ecosystems, enclaves, and cohorts may be modified by computationally complex genomic processes. In some embodiments, the enclaves and cohorts that are members of a given ecosystem may employ computationally complex genomic processes to affiliate with enclaves and cohorts that are members of other ecosystems. In this way, enclaves and cohorts may be capable of achieving unique virtual affiliation across multiple ecosystems based on computationally complex genomic processes, according to some embodiments of the present disclosure. In some examples, hyper-scalable differentiation may carry out genomic processes computed in accordance with a wide range of information theory-facilitated cypher-based, cipherless, or hybrid (e.g., cypher-based and/or cipherless) computationally complex functions, by which sequences and XNA may produce unique genomic engagement factors that may be used to generate VBLS.

In some embodiments, a CG-ESP may implement genomic information theory-facilitated processes to facilitate virtual agility. In some examples, virtual agility may provide unique engagement between ecosystems, enclaves, and cohorts that may require the abilities to execute hyper-scalable differentiation and hyper-scalable correlation at a network (e.g., open systems interconnection (OSI)), at software stack levels, and/or in hardware components. Both network and software engagement traditionally require creation, negotiation, and maintenance of session-based protocols. In some examples, these protocols may be computationally expensive and may limit network and software stack adoption options. Virtual agility may enhance engagement of ecosystems, enclaves, and cohorts by powerfully eliminating at least some of the requirements for session-based protocols. Virtual agility may reflect specific digital genomic constructions that may be generated by information theory-facilitated processes, and which may be practically unbounded and exhibit specific and user-controllable entropy.

There may be various example implementations for applying virtual agility in ecosystems, enclaves, and/or cohorts. For example, virtual agility may be adoptable at a network stack level, software stack level, and/or hardware level, thereby supporting a large number of ecosystems, enclaves, and/or cohorts. In embodiments, virtual agility may eliminate a requirement to create, negotiate, and maintain session-based protocols for network communication engagement, for software application engagement, and/or for hardware component engagement.

In some embodiments, a CG-ESP may implement genomic information theory-facilitated processes to generate and/or decode VBLS. As discussed, a CG-ESP may be configured to perform link exchange (e.g., link spawning and/or link hosting) and sequence mapping that may allow for digital objects bearing specific formats and protocols (e.g., packets, sectors, sequences, and frames) to be computationally transformed into VBLS objects. In embodiments, the VBLS objects produced by this process may be unique, non-recurring, and/or computationally quantum proof. In some embodiments, VBLS may be a consummation of genomic information theory-controlled and facilitated link, sequence, correlation, differentiation, and agility functions and processes. Computationally quantum proof VBLS may form the foundation by which specific network, software, and hardware architectures may be constructed, whether in current or newly developed deployments.

There may be various example implementations for applying virtual binary language script (VBLS) in ecosystems, enclaves, and/or cohorts. For example, VBLS may allow for control of wide range and highly flexible complements of relationships of an ecosystem, an enclave, and/or a cohort. In embodiments, VBLS may facilitate consummation and control of dynamic genomic-based architectures. In some examples, VBLS rendered digital objects may be unique, non-recurring, and computationally quantum proof, while eliminating the need for secret key generation, exchange, and retention. VBLS rendered objects may require de minimis overhead and bandwidth for engagement of VDAX(s). In some examples, VBLS rendered objects may exhibit ecosystem, enclave, and/or cohort-directed genomic modifications. In embodiments, VBLS applications may be protocol-agnostic (e.g., interoperable with network, software, and/or hardware solutions). In examples, VBLS may facilitate unique, non-recurring, and computationally quantum proof engagements between community members (e.g., ecosystem-to-ecosystem, ecosystem-to-enclave, ecosystem-to-cohort, enclave-to-cohort, and/or cohort-to-cohort engagements) based on their unique computationally complex genomic constructions and processes. In some example embodiments, any VBLS-enabled VDAX may participate in multiple VBLS relationships with other VDAX(s). In these embodiments, a VDAX may form a unique relationship with each VDAX. In some embodiments, genomic engagement factors used to be generated may be used simultaneously for primary and secondary applications that also require unique non-recurring values at a specific entropy.

In embodiments, VDAXs may be configured to engage in symmetric and/or di-symmetric VBLS-based engagements. For example, in some embodiments, VBLS-enabled VDAX(s) may engage on the bases of link exchange (e.g., spawned and hosted) which may use genomic link instructions and genomic constructions that may be the same, resulting in symmetric-based engagement. In embodiments, VBLS-enabled VDAXs may engage in di-symmetric engagement based on highly correlated genomic constructions (e.g., identical or otherwise sufficiently correlated XNA). In these embodiments, the VBLS-enabled VDAXs exchange links containing unique genomic regulation instructions (GRI). In some scenarios, however, VBLS-enabled VDAXs may engage in symmetric engagements when link exchange involves identical GRI. For example, a CG-ESP may be configured to perform one-way link exchange, whereby one VDAX may provide GRI that is used by both VDAXs in a VBLS-generation process. In this way, VBLS-enabled VDAXs may engage with other VDAXs based on symmetric and/or di-symmetric binary languages without recurring coordination between VDAXs. In some of these embodiments, VBLS-enabled VDAX engagement may proceed without negotiation of a formal session, as their symmetric or di-symmetric binary languages simultaneously encapsulate authentication, integrity, and privacy.

The rapid expansion of remote network centric highly distributed solutions and services (e.g., remote-cloud and edge-cloud) has created a situation where sensitive binaries are possibly executed in open or semi-open environments leaving them exposed to untrusted third parties (e.g., adversary). Homomorphic cryptography (cogent processing of data in encrypted state), functional obfuscation (cogent processing of data and application code in encrypted state), and various trusted execution environments (e.g., physical and software isolation of executable code) are current approaches to resolving such critical exposure. While these methods may improve markedly, none of these solutions addresses the critical scalability required for broad commercial application, as each imposes critical performance impact.

According to some embodiments of the present disclosure, CG-ESP genomic information theory technology enables computationally quantum proof, highly efficient, and hyper-scalable virtual trusted executable domains for processing of data and application code, which may be organized as genomic ecosystems. In some of these embodiments, virtual trusted execution domain allow unique transformation of component resident executable binaries and data, such as Applications (e.g., API, Libraries, and Threads), Operating System (e.g., Kernel, Services, Drivers, and Libraries), and System on a Chip (e.g., Processing Units, e.g., Core). In embodiments, CG-ESP Executable Isolation Components (EIC) facilitate component-binary-isolation (CBI) necessary for required transformations. In some embodiments, isolation is enabled by 1) unique genomic correlation between distributed components belonging to the same ecosystem, and 2) unique genomic differentiation with other executable ecosystem components. This correlation and differentiation process forms the basis by which virtual trusted execution domain (VTED) enable highly flexible and scalable component-binary-isolation (CBI).

In embodiments, hyper-scalable differentiation enables highly flexible component binary isolation (CBI) of ecosystems, enclaves, and cohorts. In some of these embodiments, virtual trusted execution domain (VTED) isolation may be achieved through the sharing of genomic components within a VTED and CBI with their VTED ecosystem VDAX, thereby establishing a hierarchical link between these members. In embodiments, a VTED provides functional replacement of homomorphic cryptography where CBIs are held at rest and runtime operations are undertaken on the encoded binaries and associated data.

In embodiments, VTED virtual-agility enables highly flexible component-binary-isolation (CBI) and control of dynamic genomic based architectures. In further embodiments, genomic correlation and differentiation enable the dynamic genomic based systems to configure dynamic genomic network topologies without the requirement to modify physical operating environments.

In embodiments, VTED-transformed executable binaries are unique, non-recurring, and computationally quantum proof. In embodiments, this transformation eliminates the requirement for secret key generation, exchange, and retention often required by trusted execution environment (TEE) technologies. In embodiments, VTED executable binaries are transformed through the application of genomic constructions (for example LNA or ZNA) to build transformed executable binaries.

In embodiments, VTED hyper-scalable-correlation, hyper-scalable-differentiation, and hyper-scalable-agility uniquely enable CBI to operate at de minimis overhead and bandwidth. In further embodiments, large numbers of genomic constructions are applied to vast numbers of CBI providing for hyper scalability of the VTED ecosystem.

In embodiments, VTED-enabled CBI for ecosystems, enclaves and cohorts may be directly genomically modified without compromise of the binary executable relationships. In embodiments, VTED enabled CBI modify binary information while the VTED maintains the ability to execute the CBI within its ecosystem.

In embodiments, VTED-enabled CBI may be compatible with known cipher-based and cipherless computational methods. In further embodiments, the compatibility of the VTED and CBI with cipher-based and cipherless computational methods is maintained by transparent genomic construction-based transformations.

In embodiments, a VTED may enable CBI executables that are unique, non-recurring, and computationally quantum proof between specific ecosystems based on their unique computationally complex genomic constructions and processes. In further embodiments, the CBI construction process applies genomic constructions that do not rely on traditional computationally expensive operations.

In embodiments, a VTED may enable CBI executables to have a number of characteristics including, unique, non-recurring, and computationally quantum proof engagements between specific ecosystems and enclaves. In embodiments, CBI executables exhibit these characteristics based on their unique computationally complex genomic constructions and processes. In further embodiments, the VTED applies genomic constructions to deploy CBI executables that enable quantum proof operations between CBI executables and genomic VTED.

In embodiments, a VTED may enable CBI executables based on their unique computationally complex genomic constructions and processes. In further embodiments, in scenarios where a VTED includes multiple cohorts across multiple enclaves, the VTED may apply genomic components to enable CBI executables that may have certain desirable characteristics such as being unique, non-recurring and quantum proof between entities. In further embodiments, an ecosystem VDAX can provide for genomic construction-based CBI licensing models where individual cohorts can have specific features or CBIs enabled for operation within their ecosystem, enclave, or cohort.

Figure 6:
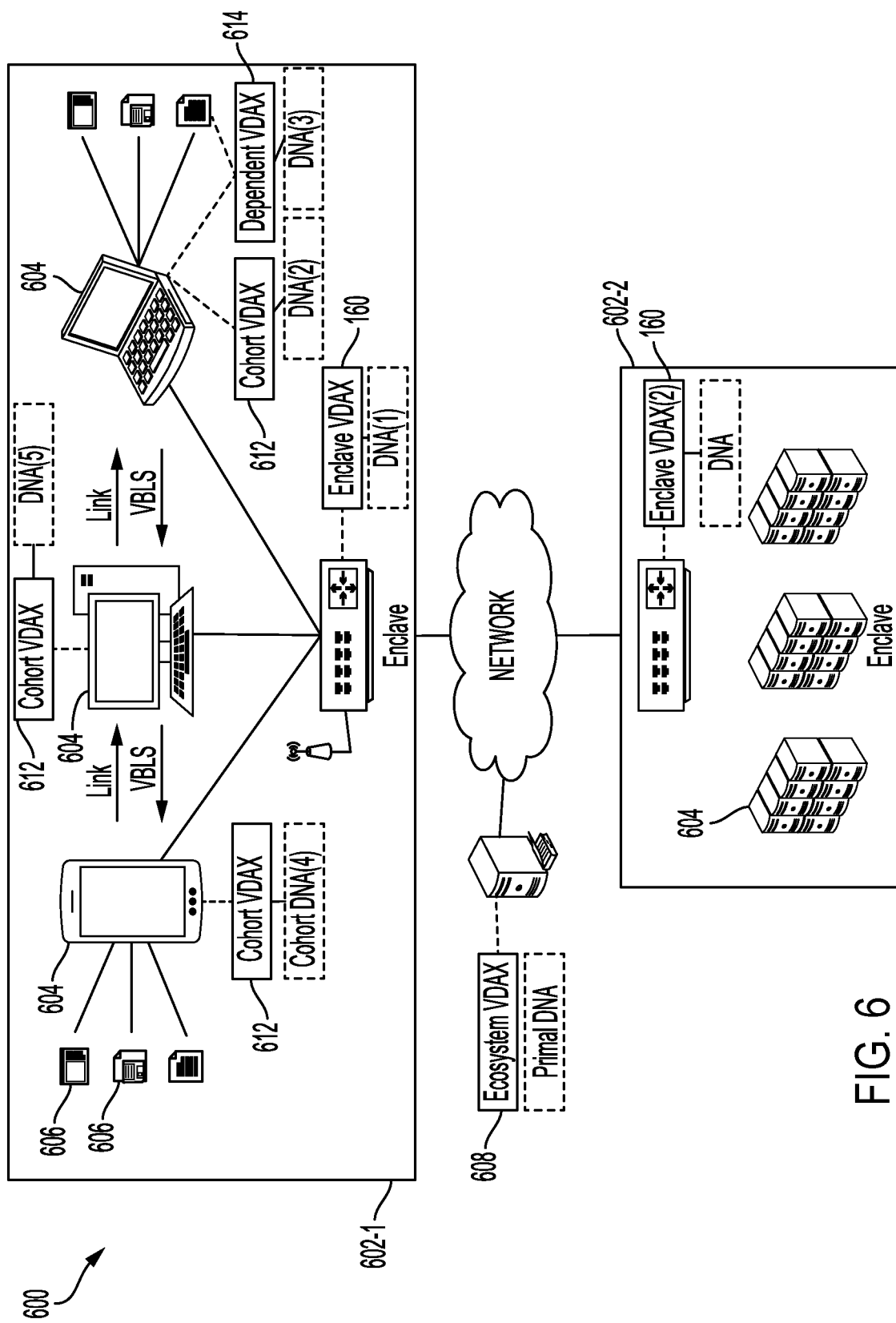
FIG. 6 illustrates an example Cyphergenics-enabled digital ecosystem that is managed by a set of CG-enabled VDAXs, in accordance with some embodiments of the present disclosure.

Referring now to FIG. 6, an example CG-enabled digital ecosystem 600 is depicted according to some example embodiments of the present disclosure. It is noted that the example configuration of the CG-enabled digital ecosystem 600 depicted in FIG. 6, including the topography and architecture of the depicted security platform depicted in the figure, are provided as a non-limiting example and are not intended to limit the scope of the disclosure. As is discussed throughout the disclosure, a configuration of CG-ESP may be defined by the community owner of a digital ecosystem. When referencing a "community owner", the term may refer to the entity that administers, maintains, or owns the community, representatives thereof (e.g., network administrator, CIO, IT administrator, homeowner, consultant, security expert, artificial intelligence software acting on behalf of the community owner, or any other suitable representative), and/or any other suitable party that may define the configuration of a CG-ESP that is used in connection with the CG-enabled ecosystem 600.

In embodiments, a set of VDAXs (e.g., VDAXs 608, 610, 612, 614) perform a set of genomic security functions on behalf of the digital ecosystem 600. It is noted that VDAXs may also be referred to as "CG-security controllers" or "security controllers". In embodiments, the CG-enabled digital ecosystem 600 includes a set of enclaves 602, and, for each enclave, a respective set of cohorts. It is noted that general references to a CG-ESP may be a reference to the configurations of the VDAXs (e.g., ecosystem VDAXs 608, enclave VDAXs 610, cohort VDAXs 612, and/or dependent VDAXs 614) that participate in the digital ecosystem. In embodiments, the set of cohorts can include independent cohorts 604. As discussed, independent cohorts 604 may include a collection of one or more devices that operate as an independent entity. Examples of independent cohorts 604 include, but are not limited to, grids, networks, cloud services, systems, computers, appliances, devices, IoT devices, and the like. In some embodiments, the set of cohorts may further include dependent cohorts 606. A dependent cohort 606 may refer to an individual digital entity which is enabled by a digital container-based VDAX or for which an independent cohort acts as a surrogate. Examples of dependent cohorts include, but are not limited to, sensors, applications, data, files, databases, media contents, cryptocurrency, smart contracts, and the like. An enclave 604 may be a collection of two or more cohorts (e.g., independent cohorts 604 and/or dependent cohorts 606) having a mutual identity of interest. As discussed, mutual identity of interest may be any logical commonality between the cohorts within an enclave. For example, a mutual identity of interest may be a set of devices, servers, documents, applications, and the like that are used by a business unit within an enterprise organization. In another example, a mutual identity of interest may be the devices, documents, applications, and the like belonging to a single family or user. In another example, a mutual identity of interest may be a set of autonomous vehicles driving on a particular grid. In embodiments, the topography of a digital community (and the architecture of the corresponding CG-ESP) may be defined by the community owner with consideration of these mutual identities of interest. In embodiments, eligibility for membership into an ecosystem 600 and/or one or more enclaves 602 thereof may be defined by a community owner and membership and revocation thereto may be administered by the community owner and/or in accordance with a set of one or more rules. It is noted that in some embodiments, certain CG-enabled digital ecosystems and the respective architectures of the corresponding CG-ESP may be defined in accordance with a default configuration, such that the community owner purchases or otherwise obtains the digital ecosystem pre-configured with the default configuration.

In some embodiments, an ecosystem progenitor (e.g., ecosystem VDAX 608) is configured to construct one or more enclaves 602 and may add a respective set of cohorts to each enclave 602 in accordance with an architecture and configurations defined by the community owner. In some embodiments, the architecture and configurations relating to a CG-enabled digital ecosystem 600 may be defined by a CG-ESP (e.g., as discussed in FIG. 4). In these embodiments, the VDAXs that participate in the digital ecosystem 100 may each execute a respective instance of the CG-ESP, such that each VDAX executes a CG-ESP instance such that the CG-ESP instance enables a respective VDAX to perform a respective role with respect to the ecosystem 600 and to form relationships with intended ecosystem members. For example, the set of VDAXs may include any suitable combination of an ecosystem VDAX 608 that serves an ecosystem-level role, one or more enclave VDAXs 610 that serve enclave level roles, one or more cohort VDAXs 612 that serve cohort-level roles, and/or one or more dependent VDAXs 614 that serve dependent cohort roles. For example, in some example implementations, an ecosystem VDAX 608 may be configured (e.g., via a CG-ESP instance) to generate, allocate, and persistently modify the genomic data of other ecosystem members, confirm engagement eligibility, exchange links, and generate VBLS; while a cohort VDAX 612 (e.g., via a cohort CG-ESP instance) may not have the capability to create or allocate genomic data with respect to the ecosystem to other cohorts, but is configured to confirm engagement eligibility, exchange links, and generate VBLS.

In embodiments, a VDAX may be implemented as any combination of software, hardware, firmware, and/or middleware that performs a specific set of genomic functions with respect to an ecosystem. It is noted that the existence of a dependent cohort 606 depends on at least one independent cohort (e.g., a file depends on the device on which it is stored or an application instance depends on the device on which the application is executed). Thus, in some embodiments, a dependent VDAX 614 of a dependent cohort 606 (e.g., a file, a media content, an application, or the like) may be executed by an independent cohort 604 (e.g., user device, smart device, gaming device, personal computing device, server, cloud system, or the like) on which the dependent cohort 606 depends.

In embodiments, an ecosystem VDAX 608 performs security related functions for a digital ecosystem and may be considered the "progenitor" of the ecosystem, as an ecosystem VDAX 608 does not require any subsequent interaction with an enclaves or the cohorts of the enclave after the ecosystem VDAX initializes assigns an enclave its genomic data set. It is noted that in embodiments, an ecosystem may be configured to enable independent sub-ecosystems and may include multiple lower level VDAXs which have functional ecosystem-level VDAX capabilities but are derived from the primary ecosystem VDAX 608.

In embodiments, an ecosystem VDAX 608 digitally generates respective genomic data sets for one-time distribution to ecosystem enclaves 602 and/or the cohorts 604, 606 within respective enclaves 602. While the genomic data objects in a genomic data set may have similar or identical constructions, mathematical competences, and/or entropy levels, each serves a different purpose. In embodiments, genomic eligibility objects (e.g., CNA or PNA objects)

provide the core genomic competence by which community members (e.g., enclaves or cohorts) computationally correlate their individual ecosystem identities. In embodiments, genomic correlation objects (e.g., LNA objects) provide the competence for member-to-member link exchange (e.g., ecosystem-to-enclave, enclave-to-enclave, enclave-to-cohort, cohort-to-cohort, and/or the like), which controls a member's ability to establish engagement with another member. In embodiments, genomic differentiation objects (e.g., XNA or ZNA objects) provide the competency for VBLS based member-to-member di-symmetric communications. In embodiments, the digital-genomic constructions of CNA, PNA, LNA, and XNA are complex and unique. In embodiments, CNA, LNA, XNA, and PNA may be derived using complex mathematical functions.

According to some embodiments of the present disclosure, an ecosystem VDAX 608 may generate a genomic data set that it assigns to itself. The genomic data set may include one or more different types of genomic data objects. For example, in some embodiments the ecosystem VDAX may generate a genomic eligibility object (e.g., a CNA object and/or a PNA object), a genomic correlation object (e.g., an LNA object), and a genomic differentiation object (e.g., an XNA object or a ZNA object) in accordance with the platform instance requirements (e.g., types of genomic object, levels of entropy of each genomic object, and specific algorithms that are used to generate such genomic data objects). In embodiments, the genomic data set that is initially generated by the ecosystem VDAX 608 and assigned to the entire ecosystem 600 may be the genomic data set from which all the progeny genomic data sets of the digital ecosystem 600 are derived. For purposes of explanation, the genomic data set of the ecosystem progenitor may be referred to as a "progenitor genomic data set" (or a "progenitor DNA set"). In some embodiments, the ecosystem VDAX 608 may initially generate the progenitor genomic data sets. For instance, the ecosystem VDAX 608 may, for each progenitor genomic data object, generate a respective binary vector having specific dimensionality.

In some embodiments, the ecosystem VDAX 608 may generate a respective progeny genomic data set for each enclave from the progenitor genomic data set. In some embodiments, the ecosystem VDAX 608 may modify the progenitor genomic data set using a set of predefined genomic operations to obtain a progeny genomic data set (or "enclave data set") that is then propagated to a respective enclave. For example, the ecosystem VDAX 608 may modify a progenitor genomic eligibility object of the progenitor genomic data set using computationally complex functions to obtain a different enclave genomic eligibility object for each respective enclave in the ecosystem; modify a progenitor correlation object of the progenitor genomic data set using computationally complex functions to obtain a different enclave correlation object for each respective enclave in the ecosystem; and modify a progenitor differentiation object of the progenitor genomic data set using computationally complex functions to obtain a different enclave differentiation object for each respective enclave in the ecosystem. In embodiments, the techniques by which different types of genomic objects are modified may differ as the different genomic objects may be implemented in different types of data structures and/or may be required to exhibit different properties. Different modification techniques are described throughout the disclosure. It is noted that in some implementations of a security platform, there may be only a single enclave. Depending on the various techniques implemented in a specific CG-ESP, certain types of genomic objects (e.g., LNA and XNA) may be highly correlated (e.g., identical or otherwise sufficiently correlated) some or all enclaves, while other types of genomic objects (e.g., CNA or PNA) are unique to each respective community members but still sufficiently correlated. It is noted that even if some types of genomic objects in a progeny genomic data set are not modified from the corresponding genomic objects of a progenitor genomic data set, the modification of one or more other portions of the genomic data set and subsequent assignment of the progeny genomic data set to a progeny community member (e.g., enclave or cohort) may also be referred to as a "derivation", such that the progeny genomic data set (e.g., enclave genomic data set or cohort genomic data set) may be said to be derived from the progenitor genomic data set (e.g., the progenitor genomic data set or an enclave genomic data set) even if one or more genomic objects of the progeny genomic data set were unmodified from the progenitor genomic data set.

In embodiments, an enclave VDAX 610 may be configured to add cohorts to a corresponding enclave by modifying the enclave genomic data set of the corresponding enclave and assigning the resultant progeny genomic data sets to respective cohorts in the enclave. In some embodiments, an enclave VDAX 610 may generate a cohort genomic data set for each new independent cohort 604 that is being added to an enclave 602. In some embodiments, CG-ESP may be configured so that an enclave VDAX 610 generates a unique, but highly correlated, genomic eligibility object (e.g., CNA) for each independent cohort 604 that is added or to be added to the corresponding enclave 602. In some of these embodiments, the ecosystem VDAX 608 or an enclave VDAX 610 may generate the genomic eligibility object such that any pair of cohorts in the enclave have a unique correlation of genomic eligibility objects. For example, in some embodiments, each cohort in an enclave 602 is assigned a genomic eligibility object that is generated based on a genomic eligibility of object of a progenitor (e.g., ecosystem or enclave), such that the cohorts are unique while maintaining a high level of correlation. In this way, any pair of cohorts may confirm eligibility to engage with one another based on the correlation of their respective genomic eligibility objects. In some embodiments, members of an enclave (e.g., cohort VDAXs) are assigned highly correlated (e.g., identical or otherwise sufficiently correlated) genomic correlation objects and genomic differentiation objects. In some embodiments, a pair of cohorts may authenticate one another based on each cohort's respective genomic correlation object and may differentiate themselves from the other cohorts based on each cohort's respective genomic differentiation object. In embodiments, the genomic correlation object and the genomic differentiation object of a cohort may be separate objects (though they may be similar or identical in structure). Alternatively, in some embodiments, the genomic correlation object and the genomic differentiation object of a cohort may be the same object.

While in some embodiments a cohort genomic data set is assigned to only one entity (e.g., device, document, sensor, or the like), it is noted that in other embodiments a community owner may allow a cohort's genomic data set to be cloned to one or more additional community members. For example, a user may have two devices that they use in connection with their employment (e.g., a desktop and a laptop computer). The community owner may opt to have devices in this scenario be assigned identical copies of a genomic data set. In this way, each device associated with a user may be granted the same access rights with respect to a respective enclave 602. It is noted that in some of these embodiments, each respective device with a cloned genomic data set would still be required to independently confirm eligibility, authenticate, and/or exchange links with other cohorts in the enclave 602.

It is noted that in some embodiments, when a VDAX is assigned a genomic data set and added to the digital ecosystem 600, the VDAX may also receive configuration data (e.g., as defined in a CG-ESP instance) as well as other suitable data that may be required to participate in the ecosystem. Such configuration data may allow the VDAX to use the correct genomic functions when performing genomic operations such as eligibility correlation, link spawning, link hosting, sequence mapping, LNA modification, XNA modification, binary object transformation, and the like. In these embodiments, such configuration data allows community members to successfully engage and exchange data with other community members. In some embodiments, a VDAX may also receive genomic community progeny (GCP) data that uniquely identifies a community member. In these embodiments, the GCP may be used in confirming engagement eligibility of cohorts.

In some embodiments, a cohort VDAX 612 may be configured to perform genomic security operations and processes on behalf of an independent cohort 604. In some embodiments, a cohort VDAX 612 facilitates data exchange with sufficiently correlated community members (e.g., other cohorts in an enclave 602). In some of these embodiments, the facilitation of data exchange with another community members may include confirming engagement eligibility (e.g., engagement integrity and engagement synchronization) and exchanging links with the other respective community member (e.g., with another independent cohort 602). In some embodiments, confirming engagement eligibility and link exchange is a one-time process, such that once a pair of cohorts have successfully completed this "handshake", the pair of VDAXs can exchange data securely for as long as they continue to share highly correlated (e.g., identical or otherwise sufficiently correlated) differentiation objects. For example, a pair of VDAXs may initially confirm engagement eligibility and exchange links and, unless they no longer share the common differentiation object, the VDAXs can continue to communicate securely for days, weeks, months, or years. Once the cohorts no longer share common differentiation objects, they can attempt to exchange data, but will be no longer able to decode any encoded digital objects provided by the other respective cohort.

In embodiments, a pair of VDAXs engage with one another via virtual binary language script (VBLS) that is generated and decoded by the respective VDAXs. As discussed, VBLS may refer to unique, non-recurring (or recurring with infinitesimal probabilities) binary languages. In embodiments, individual instances of VBLS may be referred to VBLS objects. In embodiments, a first VDAX (e.g., cohort VDAX 612 or an enclave VDAX 610) may generate VBLS objects for a second VDAX (e.g., cohort VDAX 612 or an enclave VDAX 610) based on genomic regulation instructions (GRI) encoded in a link provided to the first VDAX by the second VDAX and the genomic data (e.g., XNA) of the first VDAX. In these embodiments, the second VDAX may receive VBLS objects from the first VDAX and may decode the VBLS based on the GRI provided in the link to the first VDAX and the genomic data set of the VDAX. In some embodiments, a VBLS object includes metadata that the second VDAX processes to decode an encoded digital object that is included in the VBLS object. For example, in some embodiments, a VBLS object is a data packet that includes packet header and an encoded digital object (e.g., a payload). In some of these embodiments, the metadata that is used to decode the encoded digital object includes a public sequence or private sequence that appears in one or more protocol layers of the digital object (e.g., TCP, UDP, TLS, HTTP, H.256, or any other suitable protocol layer types).

In embodiments, the first VDAX may generate a VBLS object corresponding to a digital object that is to be provided to the second digital object by determining a genomic engagement factor based on a sequence (e.g., public or private sequence) and the genomic differentiation object of the first VDAX. In embodiments, the first VDAX modifies its genomic differentiation object according to the GRI provided by the second VDAX in the link provided by the second VDAX and maps a sequence (or a value derived therefrom) contained in the digital object (e.g., protocol or format data in the digital object) into the modified genomic differentiation object to obtain the genomic engagement factor. In embodiments, the first VDAX may use a computationally complex function (e.g., cipher-based function, non-cipher-based function, or hybrid function) to map the sequence into the modified genomic differentiation object. The first VDAX may then encode a digital object (e.g., a packet payload, a shard of a file, a video or audio frame, or any other suitable type of digital object) using the genomic engagement factor to obtain the encoded digital object. In embodiments, the first VDAX leverages a computationally complex function (e.g., encryption function or a disambiguation/XOR function) to encode the digital object based on the genomic engagement factor. The first VDAX may then provide a VBLS object that includes the metadata (e.g., the sequence) and the encoded digital object to the second VDAX (e.g., via a network and/or a data bus).

In embodiments, the second VDAX receives the VBLS object and may decode the encoded digital object in the VBLS object based on the metadata included in the VBLS object and the genomic differentiation object of the second VDAX. In embodiments, the second VDAX is configured to extract a sequence from the VBLS object (e.g., a public or private sequence unencrypted portion of a data packet or data frame). The second VDAX may also modify its genomic differentiation object using the GRI contained in the link that was provided to the first VDAX (e.g., during a link exchange process), such that the second VDAX maps the sequence (or a value derived therefrom) into the modified genomic differentiation object using the same computationally complex function to obtain a genomic engagement factor. Assuming that the first VDAX and the second VDAX have matching (or sufficiently correlated in some embodiments) genomic differentiation objects and both use the same instructions to modify the respective genomic differentiation objects, then the same genomic engagement factor will be produced given the same sequence and the modified genomic differentiation object. In embodiments, the second VDAX leverages a function (e.g., decryption function or a disambiguation/XOR function) to decode the digital object based on the same genomic engagement factor. In this way, the first VDAX and the second VDAX are able to differentiate themselves in a unique manner from other community members that share the same genomic differentiation object, as the other community members not in possession of the link provided by the second VDAX to the first VDAX cannot modify their genomic differentiation object in the same manner. Thus, the other community members will be unable to generate the genomic engagement factor even if those community members are configured to execute the same computationally complex mapping function and are able to determine the public sequence. Interloping or otherwise malicious devices that do not have access to the genomic data would be further limited, as such interlopers may be unknowing of one or more of: the computationally complex functions used to generate the genomic engagement factor, how to extract the sequences, or the common genomic differentiation object. As such, they would be unable to determine the genomic engagement factor without brute-force methods. Furthermore, as a CG-ESP may be configured such that a first VDAX calculates a new genomic engagement factor for every digital object (e.g., every data packet, shard of a file, video frame, audio frame, or the like), each encoded VBLS object would require a separate brute force determination of the digital object, making the VBLS generated by the first VDAX for a second VDAX quantum-proof.

In some embodiments, the metadata in a VBLS object may further include data integrity information. For example, the data integrity information may be a value that is calculated by the first VDAX over the plain data and then used as sequence. In this way, the second VDAX may verify, that the VBLS object was not tampered with.

In embodiments, digital objects may refer to OSI components (e.g., level 2-7 components) and/or computer-executable code/instructions. Examples of digital objects include packets, sectors, frames, and sequences. VBLS may refer to languages spoken by an enclave or a cohort to another enclave or cohort that is uniquely understood by the recipient enclave or cohort—that is, languages that are only understandable by the recipient enclave or cohort. In this way, interlopers aiming to include unauthorized cohorts, viruses, and/or malware, cannot generate or decipher VBLS between authorized cohorts.

It is appreciated that the foregoing discussion is provided for as an example of a CG-enabled digital ecosystem 600. It is appreciated that different configurations of a CG-ESP may perform different functions and operations and may have different CG-ESP modules. For example, different configurations of CG-ESP may use different encryption functions, different hash functions, different sequence mapping functions, different types of genomic constructions, or the like. It is further noted that CG-ESPs may be configured for different ecosystems which may enable different architectures.

FIGS. 7-11 illustrate different types of digital ecosystems and corresponding architectures. Contemporary network capabilities substantially reflect their underlying deployment architecture. In embodiments, CG-enabled architectures that enable VBLS using genomic constructions may operate at the bit level and, therefore, may remain interoperable with the underlying deployment architecture. VBLS provides unprecedented facility and flexibility to uniquely tailor applications for network, software, and/or hardware-centric architectures. Examples of CG-ESP ecosystem architectures may include, but are not limited to: directed architectures that support static ecosystems, free-form architectures that are configured for transient ecosystems, spontaneous architectures that support dynamic ecosystems, ephemeral architectures that support executable ecosystems, and Interledger architectures that support affirmation ecosystems. In embodiments, these architectures, which may overlay existing physical network topologies, evidence genomic constructed topologies. In some embodiments, multiple genomic constructed topologies may exist simultaneously and interoperably. For example, a computing device may be an executable ecosystem, such that internal components of the computing device exchange VBLS; at the same time, the computing device may be a member of a static ecosystem, such that the computing device may engage with other devices in the static ecosystem using a different set of genomic data.

Figure 7:
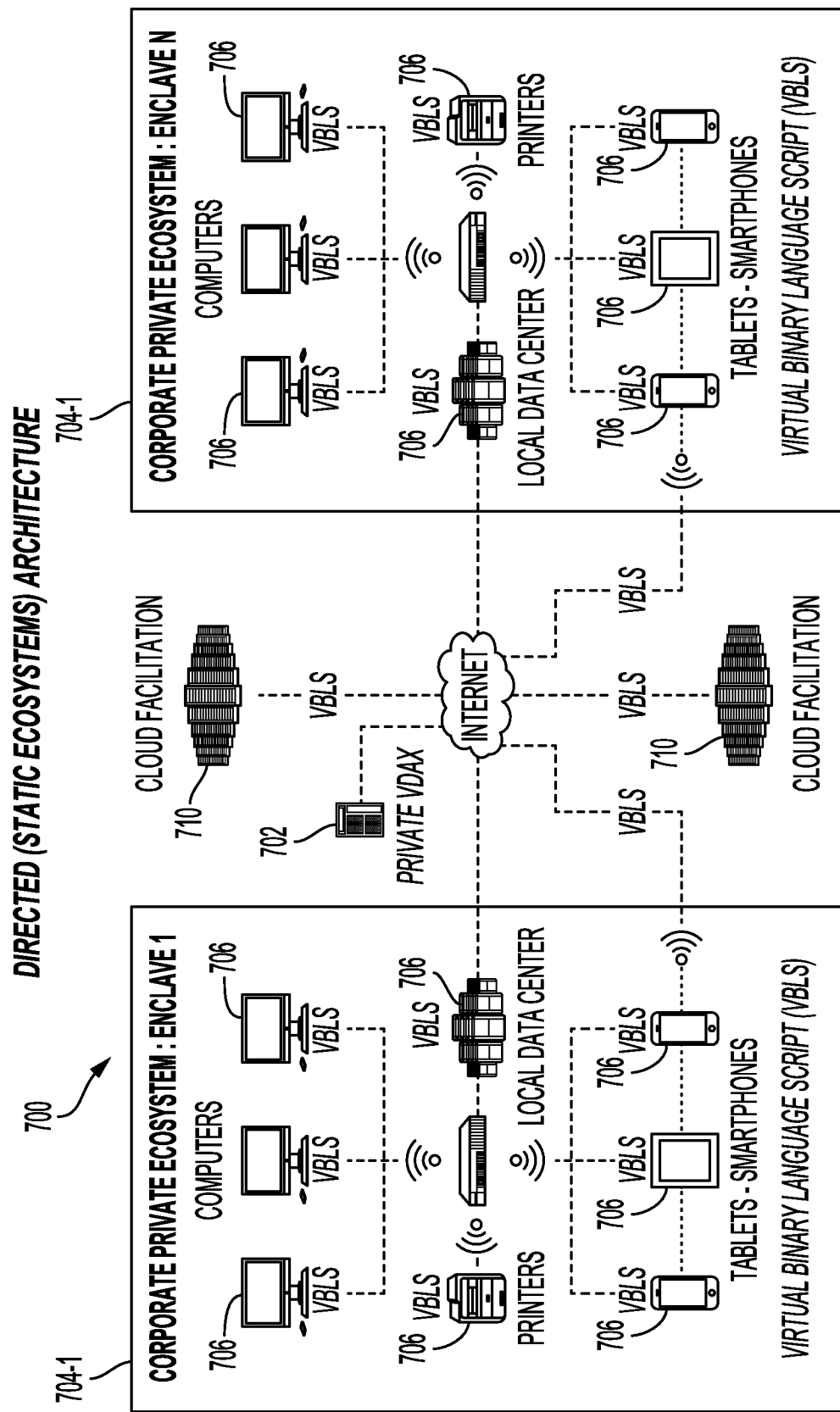
FIG. 7 illustrates example implementations of security platform instances that are configured in accordance with directed architectures in support of static ecosystems, in accordance with some embodiments of the present disclosure.

Referring to FIG. 7, a directed architecture may be implemented in a static ecosystem, as the features of such ecosystems and the enclaves and cohorts that participate in these ecosystems exhibit a fairly stable configuration. For example, in an enterprise deployment, the majority of users will use similar devices (e.g., desktops, laptops and mobile devices), email clients, software solutions (both cloud-based and locally executed), devices (e.g., printers, IoT devices) and the like, all of which are unlikely to change much over time. These ecosystems provide relationship stability without loss or stifling of flexibility. These architectures' attributes are uniquely extended and enhanced—such that they may be capable of standing alone. In some example embodiments, a provision that may be enabled by static architectures, as opposed to free-form architectures, may be the manner by which correlation is executed and managed. In the case of static architectures, correlation is accomplished on the basis of common genomic constructions, which is provisioned by a single ecosystem VDAX.

In embodiments, directed architectures reflect configurations where an ecosystem VDAX establishes one or more enclaves that exhibit specific genomic correlation and differentiation. In some of these embodiments, each enclave VDAX may correspondingly establish one or more cohorts, which also exhibit specific genomic correlation and differentiation. In embodiments, such ecosystem, enclave, and cohort configuration may be exhibit hierarchical genomic correlation and differentiation, which may be beneficial in directed architectures. In embodiments, directed architectures, ecosystem, enclave, and cohort VDAXs may have multiple genomic correlations and differentiation attributes. For example, enclaves in directed architectures may propagate both subordinate enclaves and cohorts. In embodiments, different architectures may be configured to exhibit different correlation properties. For example, directed architectures may exhibit inherently common correlation, while free-form architectures may exhibit arranged common correlation.

In embodiments, genomic correlation and differentiation enable directed architectures to configure genomic network topologies without the requirement to modify physical topology. For example, in these embodiments, a community owner may be able to control engagement of cohorts in different enclaves using different LNA and XNA, such that engagement (e.g., via link exchange) between cohorts in different enclaves may be prevented by a community by controlling the LNA and/or XNA that is provided to different enclave members. Similarly, in these examples, the community owner can create new enclaves also by controlling the LNA and XNA that are provided to different cohorts.

In embodiments, the genomic topologies enabled by directed architectures may be incrementally genomically modified. In some of these embodiments, a community owner may periodically modify certain genomic constructions (e.g., XNA and/or LNA) of some or all ecosystem and/or enclave members for any number of considerations (e.g., security, removing cohorts that are no longer, dissolving an enclave, and the like).

FIG. 7 illustrates an example of a CG-enabled ecosystem 700 having a directed architecture, whereby the ecosystem 700 is a static ecosystem. In embodiments, static ecosystems include enclaves and the cohorts that support more traditional deployments to include local, internally managed but distributed, and remote on-demand IT resources and capabilities. Static ecosystems require seamless performance and security. These deployments are often found in enterprise class organizations and institutions, but owing to their complexity, security has been a challenge for small and medium size businesses (SMB). These implementations tend to be relatively static and centrally managed. For example, in a static ecosystem a business unit may include a number of employees that are allowed to access (e.g., read, write, and/or edit) a common set of files. Furthermore, employees may work on special projects (e.g., a product release), and those employees typically are allowed to access another common set of files. In some scenarios, a community owner (e.g., represented by an IT administrator or any other party affiliated with an enterprise) may define a set of policies that define the type of access individual cohorts may be granted with respect to certain files or folders, one or more enclaves that each cohort belongs to, the cohorts and/or enclaves that each cohort may digitally engage with (e.g., printers, local file servers, and the like), and/or other suitable policies. As discussed, such policies may be enforced using genomic constructions, such as XNA, CNA, PNA, and LNA, which can be used to define permissible relationships and genomic topologies across the ecosystem.

In embodiments, a security platform may be implemented as a directed architecture when the digital ecosystem is a static ecosystem 700. Using a directed architecture, an ecosystem VDAX (e.g., private VDAX 702) defines one or more enclaves 704 corresponding to the static ecosystem. In the example of FIG. 7, the ecosystem VDAX has defined N enclaves 704, including a first enclave 704-1 and an Nth enclave 704-N, in a hierarchical manner (e.g., a directed architecture). For each enclave 704-1 . . . 704-N, the ecosystem VDAX 702 can create an enclave VDAX (which executes an enclave VDAX) for the enclave 704-1 and can assign one or more cohorts 706 to the enclave 704-1. In this example, the cohorts 706 of the first enclave 704-1 and the Nth enclave 704-N include workstations, tablets, local data centers, printers, IoT devices, mobile devices, and the like. It is noted that in this example, the router in each enclave is not considered a cohort and does not communicate using VBLS. Rather, each router is a pass-through device that routes data packets containing VBLS to cohorts 706 within the enclave 704, within the ecosystem 700, and/or to any broader network (e.g., the Internet). In embodiments where the routers are cohorts, each router may have its own genomic data set (XNA, LNA, and CNA), and other cohorts 706 within the enclave 704 would communicate with the router using VBLS that only the router could understand. It is appreciated that such decisions are design choices that can be made by the community owner or a provider of the CG-ESP. It is further noted that the cloud facilities 710 in this example are not enclaves of the ecosystem 700. In this example, the cloud facilities 710 host third party applications and/or data. In some example embodiments, the ecosystem VDAX 702 of the ecosystem 700 may be configured to negotiate an arrangement with a VDAX (not shown) of the third party application system and/or the cloud facility to obtain genomic materials that correlate to the cohorts of the directed ecosystem, thereby enabling authentication, linking, and engagement between the ecosystem and the third party application system/cloud facility. Additionally or alternatively, the community owner may decide that certain third party service providers (e.g., cloud services) may be added to the ecosystem as cohorts, such that the community owner may restrict the third party service provider's access to the ecosystem to specific uses via LNA and XNA construction. In this way, the third party service would only be able to exchange links with other cohorts that have similar LNA (e.g., intended users of the third party service). Similarly, when the relationship ends with the third party service provider, the community owner may revoke the third party service provider via XNA modification.

In some embodiments, an enclave VDAX of an enclave 704 (or the ecosystem VDAX), can generate and allocate genomic materials to the VDAXs of each cohort 706 in an enclave 704. In embodiments, the ecosystem VDAX 702 creates genomic information (e.g., XNA, LNA, and CNA) for each respective enclave. In response to receiving its genomic information, an enclave VDAX may generate respective genomic information for each cohort 706 included in the enclave 704. For example, the enclave VDAX (or the ecosystem VDAX) may generate CNA that is allocated to new cohorts and/or may provide its LNA and/or XNA to the members of the enclave 704. Depending on the configuration of a CG-ESP and the genomic constructions thereof, two cohort VDAXs that have been admitted to an enclave, may be required to participate in link exchange. Once two cohort VDAXs have participated in link exchange, they may begin to exchange VBLS based on the hosted link(s).

In a directed architecture, the ecosystem owner (e.g., via an ecosystem VDAX 702) can manage the security features of enclaves 704 and/or cohorts 706 within the enclaves 704 by initiating modification of the XNA and/or LNA of a cohort 706 and/or enclave 704. For example, if a certain employee is no longer part of a business unit, the employee's access to certain resources (e.g., documents, printers, file systems, or the like) may be revoked. In embodiments, a VDAX can "revoke" access to the cohorts (e.g., workstation, mobile device, or the like) of the employee by initiating a modification of the XNA (and in some scenarios LNA) of the cohorts 706 that will remain in the enclave 704 and/or ecosystem 700 without initiating the same XNA modification to the cohorts 706 corresponding to the removed employee. In another example, if the employee had access to a first folder of documents and a second folder of documents, and the employee's access to the first folder is being revoked but not his or her access to the second folder, the VDAX can initiate the modification of the XNA of the second folder and the DNA and LNA of the other cohorts of the enclave without providing the modification to the cohort(s) of the employee whose access to the second folder has been revoked. In these provided examples, a community owner is able to control engagement of cohorts in different enclaves using genomic constructions (e.g., LNA and/or XNA).

It is appreciated that the foregoing discussion provides some example implementations of directed architectures. It is appreciated that CG-ESPs can be configured in accordance with directed architectures in other suitable ecosystems without departing from the scope of the disclosure.

Figure 8:
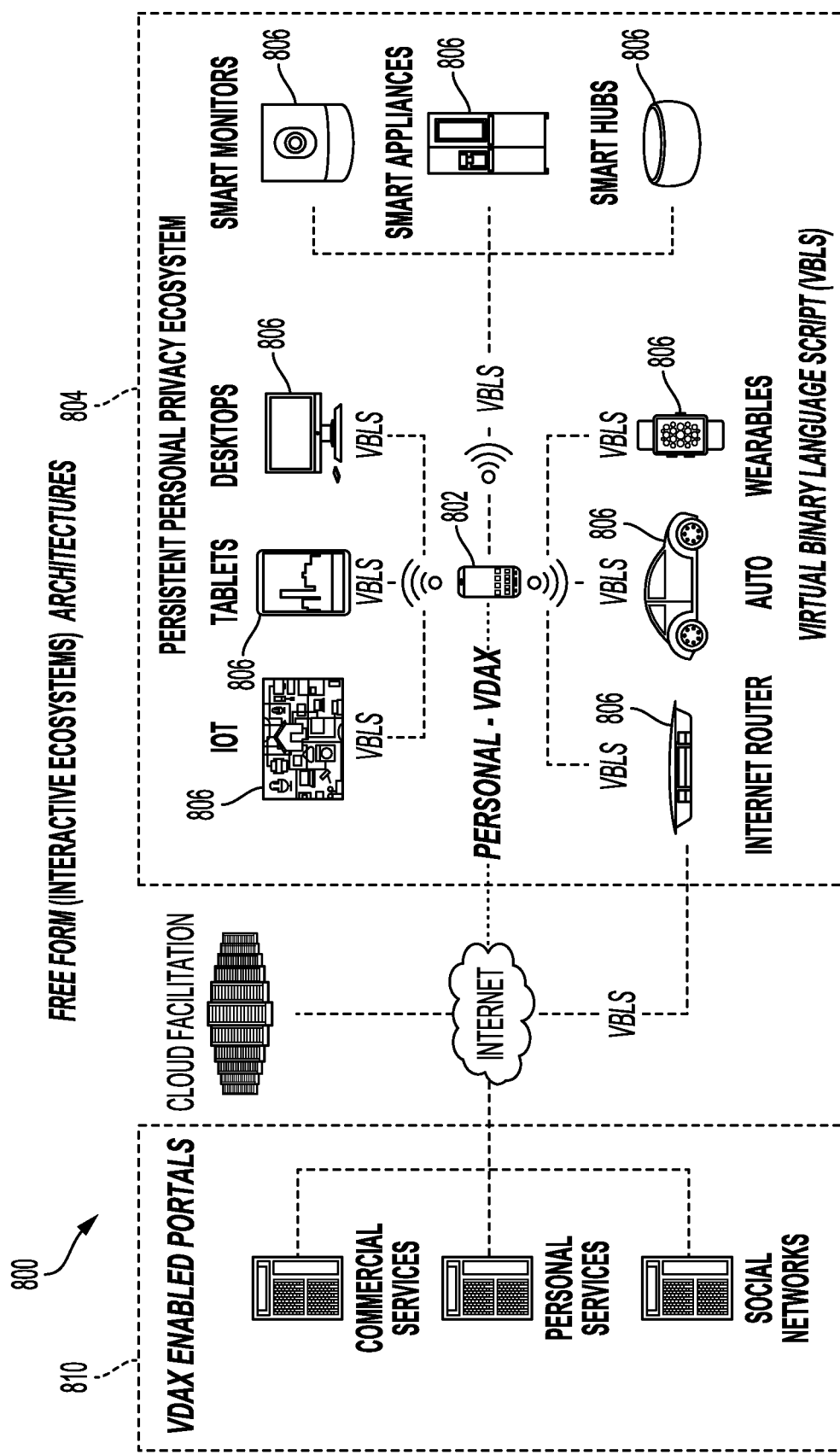
FIG. 8 illustrates an example implementation of a security platform instance that is configured in accordance with a free-form architecture in support of a transient ecosystem, in accordance with some embodiments of the present disclosure.

Referring now to FIG. 8, free-form architectures feature ecosystems, enclaves, and cohorts which are potentially unrelated. In such ecosystems, the configurations of the enclaves (e.g., a limited number of users, devices, and the like) are fairly stable, but may change in accordance as per their mutual identity of interest (e.g., changes to the ecosystem are less predictable than in static ecosystems). Thus, free-form architectures may provide relationship stability without loss or stifling of flexibility. In some embodiments, these architectures' attributes may be uniquely extended and enhanced—such they are capable of standing alone. In embodiments, a provision that may be enabled by free-form architectures, as opposed to Static Architectures, is the manner by which correlation is executed and managed. In the case of free-form architectures, common genomic correlation cannot be accomplished on the same basis as in the case of static architectures, such is accomplished by use of alternate genomic sub-constructions in order to facilitate common genomic correlation, e.g., free-form.

In embodiments, free-form architectures may facilitate genomic construction of application-specific network topologies. For example, in some embodiments, ecosystem VDAXs independently initiate unique genomic correlation and/or differentiation constructions (e.g., LNA and/or XNA). In some embodiments, enclave VDAXs and/or cohort VDAXs in a directed architecture may acquire their unique genomic correlation constructions directly (e.g., LNA). For example, the ecosystem VDAX may control which cohorts should belong to which enclaves via genomic construction generation and modification.

In embodiments, ecosystem VDAXs in free-form architectures may acquire their unique genomic correlation constructions via alternate genomic sub-constructions. In some of these embodiments, each ecosystem VDAX may have a unique genomic construction by which correlation and differentiation attributes are derived. In some of these embodiments, these derived attributes control the genomic topology of an ecosystem's enclaves. In some of these embodiments, each enclave (e.g., via its enclave VDAX) may have a unique genomic construction by which correlation and differentiation attributes are derived, these attributes control the genomic topology of the enclave's cohorts (e.g., cohort VDAXs). In embodiments, multiple genomic constructed topologies, which overlay physical network topologies, may exist simultaneously and in an interoperable manner. In some embodiments, genomic-based digital network topologies are independent from underlying technologies used to enable physical or logical digital networks. In these embodiments, genomic-based digital networks render their topologies, which in some scenarios, may be solely dependent upon genomic construction-facilitated VBLS.

FIG. 8 illustrates an example of a security platform having a free-form architecture that serves an interactive ecosystem 800. In embodiments, an interactive ecosystem 800 may include one or more enclaves 804 (e.g., personal residence, home office, small business, or the like) and each enclave may include one or more cohorts 806 (e.g., computers, appliances, hubs, media devices, IoT devices, wearable devices, smart speakers, and the like) that share mutual identity of interests, and are capable of interacting with a wide range of network enabled web portals (e.g., Facebook, Amazon, banking servers, healthcare servers, and the like) which services and applications are interactive but require user-controlled security. An example of an interactive ecosystem 800 may be a home network, a small office network, or the like.

In a free-form architecture, a cohort 806 within the ecosystem 800 may be designated as the VDAX 802 of the ecosystem 800. For example, a user may designate a mobile device, a desktop, or a router to act as the VDAX 802 of the ecosystem 800. Furthermore, via the VDAX 802, a user may define one or more enclaves (e.g., via a user interface). For example, in some situations a user may define a single enclave 804 (e.g., all devices associated with the user). In another example, a user may define different enclaves 804 for different family members, different device classes, and/ or other logical commonalities (e.g., an enclave for the devices used by the parents, an enclave for devices used by the minors, and an enclave for smart devices, such as thermostats, appliances, televisions, speakers, and the like). In embodiments, the user may define, via the VDAX 802, one or more settings (e.g., rules, policies, blacklists, whitelists, and the like) for enclaves 804 and/or individual devices. These parameters may be used when generating the genomic data (e.g., XNA, LNA, CNA and/or PNA) of an enclave 804 or cohort 806. The VDAX 802 may generate the genomic data for each enclave 804. In some embodiments, the VDAX 802 may also generate the genomic data for each cohort (independent and dependent). In other embodiments, another device may host an enclave VDAX, whereby the enclave VDAX generates the XNA, LNA, PNA and/or CNA of the cohorts 806 in the enclave 804.

In an interactive ecosystem 800, the external systems that a cohort 806 may access are wide ranging. For example, a user may use their workstation or mobile device to access web portals to stream videos, access social media platforms, visit websites, read emails and messages, open attachments, and the like. Similarly, the user may have devices in their home that can detect motion, record audio, capture video, or record sensor measurements or other data relating to the user or his or her home or office. These devices also access web portals to report data or to leverage a service of the web portal (e.g., ordering goods, adjusting thermostat, or the like). In the former example, the user may be concerned with privacy and/or malicious software (e.g., viruses or malware) being installed on their devices. In the latter example, users may be concerned with privacy (e.g., who has access to the data captured by their smart devices or unknown surveillance). In an interactive ecosystem 800, a security platform implemented as a free-form architecture mitigates these concerns. In some embodiments, the VDAX 802 of the ecosystem 800 may negotiate a secure relationship with a VDAX (not shown) of a portal 810. In some of these embodiments, the VDAXs of the user and the web portal generate correlated genomic data. In these embodiments, the VDAX 802 of the interactive ecosystem may then generate genomic data for a cohort (e.g., by way of the cohort's VDAX) that attempts to access the web portal 810. When the cohort 806 attempts to access the web portal, the cohort 806 and the web portal 810 generate and exchange engagement information that allows the pair of corresponding VDAXs to confirm eligibility-integrity and/or synchronization and ultimately exchange links. Once the web portal 810 and the cohort 806 have spawned and exchanged links, the cohort 806 and the web portal 810 may respectively host the other party's link. The cohort 806 may use the link spawned and hosted by the web portal 810 to generate VBLS that is sent to the web portal 810, and the web portal 810 may use the link spawned by the cohort 806 to generate VBLS that is sent to the cohort 806. The foregoing example is but a single example of a free-form architecture, and other implementations are within the scope of the disclosure.

Figure 9:
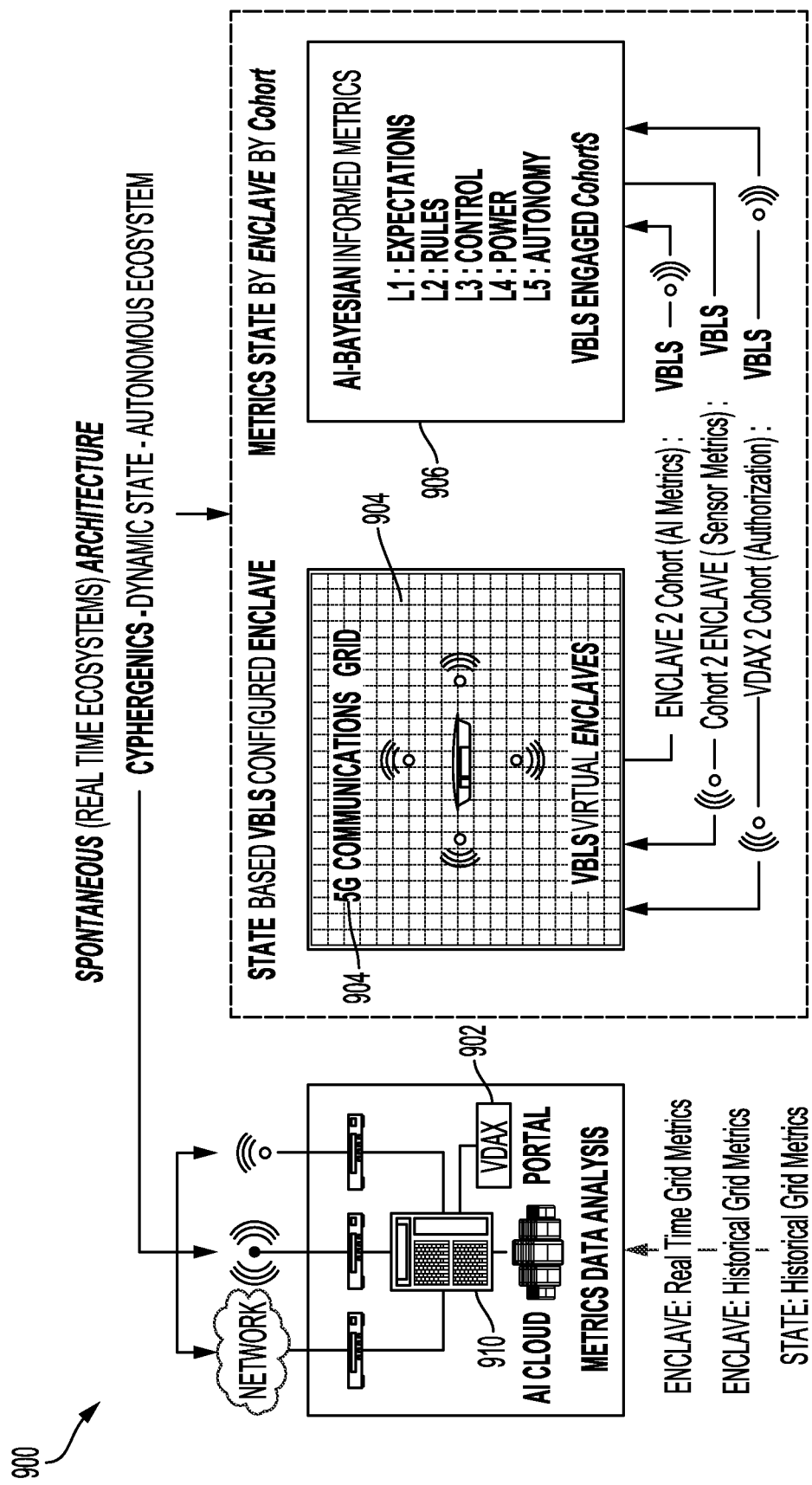
FIG. 9 illustrates an example implementation of a security platform instance that is configured in accordance with a spontaneous architecture in support of a real-time/dynamic ecosystem, in accordance with some embodiments of the present disclosure.

Referring now to FIG. 9, a spontaneous architecture may be implemented to support applications and services subject to highly dynamic changes in metric (e.g., time, data, condition, demand, coordinate, action, relative position, and event) states. For example, an autonomous car management system may manage an ecosystem of autonomous vehicles moving throughout a grid of control where the grid of control is dynamically controlled based on the traffic situation on the road. In embodiments, this grid topology may be dynamically reconfigured to enable the support of highly dynamic changes in environment and state. In a further example, the spontaneous architecture may provide for an air traffic control system or a military theater or swarm of drones where the cohorts are constantly changing and may have highly dynamic security responses to the environment. In embodiments, the spontaneous topology can change by altering the DNA in response to situational events. To respond to these situational events modified DNA may be dynamically distributed to different cohorts or groups.

In embodiments, such architectures—spontaneous architectures—may benefit from complete and/or real time reconstruction of their network topologies to address specific control parameter such as metric states or operator preference(s). In certain situations, network architectures are required to address an additional challenge in that they are incapable of supporting highly dynamic changes in metrics and the variety of their possible state. In embodiments, a spontaneous architecture addresses these highly dynamic changes in metrics allowing for support of emerging ultra-bandwidth applications or artificial intelligence portals. Further examples of applications of spontaneous architectures may include military theaters, management of electrical power grids or highly distributed financial trading systems.

In embodiments, ecosystem VDAXs may construct and control genomic network topologies that support applications requiring dynamic state attributes. In embodiments, an ecosystem VDAX may be able to control engagement of cohorts in an ecosystem using different genomic constructions (for example, LNA and XNA), such that engagement (e.g., via link exchange) between cohorts in the ecosystem may be enabled, prevented, and/or revoked by a community owner by controlling the LNA and/or XNA that is provided to different members. Similarly, in these examples, the ecosystem VDAX can alter the dynamic network topology of the ecosystem by controlling the LNA and XNA that are provided to different cohorts.

In embodiments, enclave VDAXs can be configured to control respective portions of an ecosystem's genomic network topology, whereby an enclave VDAX is responsible for specific VDAX-designated functions and processes with respect to the enclave VDAX's portion of the genomic network topology. In further embodiments, genomic correlation and differentiation enable the enclave VDAXs to configure dynamic genomic network topologies without the requirement to modify physical topology. For example, in these embodiments, the Enclave VDAXs may be able to control engagement of cohorts in different enclaves using different genomic constructions (for example, LNA and XNA), such that engagement (e.g., via link exchange) between cohorts in different enclaves may be dynamically enabled or prevented or revoted by an enclave VDAX by controlling the LNA and/or XNA that is provided to different enclave members. Similarly, in these examples, the enclave VDAXs can create new dynamic spontaneous enclaves also by controlling the genomic constructions (e.g., LNA and XNA) that are provided to different cohorts. In some embodiments, cohort VDAXs may control respective portions of the ecosystem genomic network topology. In these embodiments, a cohort VDAX may be responsible for performing specific functions for a respective portion of the genomic network topology as designated by an Ecosystem VDAX and/or enclave VDAX. In further embodiments, cohort VDAXs performing such functions may enable spontaneous architectures by configuring dynamic genomic network topologies without the requirement to modify a physical network topology. For example, in these embodiments, a cohort VDAX may be able to control engagement of VDAXs for a designated portion of a genomic network topology using different genomic constructions (for example, LNA and XNA), such that engagement (e.g., via link exchange) between VDAXs in the designated portion may be dynamically enabled, prevented, and/or revoked by a designated cohort VDAX by selectively modifying the LNA and/or XNA of those VDAXs.

In embodiments, various types of interactions (e.g., ecosystem VDAX-to-enclave VDAX, enclave VDAX-to-cohort VDAX, ecosystem VDAX-to-cohort VDAX, and/or cohort VDAX-to-cohort VDAX interactions) may be controlled by specific genomic constructions (e.g., CNA, PNA, LNA and XNA) determined by the ecosystem VDAX. For example, in these embodiments, an ecosystem VDAX may control engagement between VDAXs corresponding to respective portions of a genomic network topology by dynamically modifying portions of some or all of the genomic constructions (e.g., LNA or XNA) of ecosystem, enclaves, and/or cohort VDAXs in the respective portion of the genomic network topology. In this way, VDAXs can be added, prevented, and/or revoked from different portions of the genomic network topology via their respective genomic constructions. For example, in some embodiments, an enclave VDAX that is designated with controlling a respective portion of a genomic network topology can alter that portion of the genomic network topology by selectively modifying the genomic constructions of VDAXs that are to be added and/or revoked from the respective portion of the genomic network topology. In embodiments, the genomic constructions (e.g., CNA, PNA, LNA and/or XNA) responsible for ecosystem, enclave, and cohort engagements may be modified to change the basis of differentiation and/or correlation, which in turn modifies the genomic network topology. In some embodiments, such modifications may be effected as part of updating the genomic network topology (e.g., cohort revocation). In embodiments, these genomic constructions may be modified to enable control the engagement of cohorts in the ecosystem using different genomic constructions (for example, LNA and XNA), such that engagement (e.g., via link exchange) between members in the ecosystem may be enabled or prevented or revoked by controlling the genomic constructions. Similarly, in these examples, the ecosystem CNA, PNA, LNA and/or XNA can alter the dynamic network topology of the ecosystem by controlling the genomic constructions that are provided to different cohorts.

In embodiments, spontaneous architectures retain their operational integrity irrespective of the dynamic frequency of the metric states they support (for example, time, data, condition, demand, coordinate, action, or event). For example, in some embodiments, cohorts may operate in an environment where the reporting frequency of the metrics can be variable. In these embodiments, the spontaneous architecture handles these variations in the overall metric data while maintaining the overall integrity of the ecosystem.

FIG. 9 illustrates an example of a security platform having a spontaneous architecture that serves a dynamic ecosystem 900. In embodiments, dynamic ecosystems 900 include enclaves and their cohorts that support applications and services that are subject to highly dynamic changes in state (time, data, conditions, demand, coordinates, actions, et al). Examples of dynamic ecosystems 900 include artificial intelligence applications, autonomous vehicle systems, and real-time supply chain systems. Spontaneous ecosystems 900 often require complete reconstruction in real time in response to specific states and or operator preference(s). The security requirements of these ecosystems are such that traditional cryptographic protocols are both incapable of supporting the dynamic frequency and incompatible with variety of states possibly attended to. In embodiments, a security platform is implemented as a spontaneous architecture to serve a spontaneous ecosystem 900. These architectures hold great promise for the emerging integration of ultra-bandwidth and artificial intelligence (AI) portals.

In a spontaneous architecture, an ecosystem VDAX 902 may be configured to dynamically define enclaves 904 and/or to assign cohorts 906 to one or more enclaves 904 in real time. In some of these embodiments, an AI portal may be leveraged by the VDAX 902 to define the enclaves 904 and to assign cohorts 906 thereto. For each cohort 906, the VDAX 902 may initially generate and provide genomic information for the cohort 906. This genomic information may be generated and provided each day, each time the cohort 906 is powered on, or at other suitable intervals. The genomic information may be correlated with all the other cohorts 906 in the ecosystem 900, but without being assigned to a particular enclave 904. As the cohort 906 participates in the ecosystem 900, the VDAX 902 and the AI portal 910 may determine which enclaves 904 that the cohort 906 belongs to and which enclaves 904 the cohort 906 should be revoked from. For each enclave 904 that the cohort 906 belongs to, the VDAX 902 may communicate modifications to the cohort's XNA and LNA, such that the AI portal 910 may be able to decipher VBLS generated by cohorts 906 within those enclaves 904. Similarly, for each enclave 904 that a cohort 906 has been revoked from, the VDAX may communicate modifications to the cohort's XNA and LNA, such that the cohort 906 may be no longer able to decipher VBLS generated for remaining cohorts 906 within those enclaves 904. In spontaneous ecosystems, the VDAX (or multiple VDAXs) may manage membership for the enclaves 904 within the ecosystem 900 in this manner, such that cohorts 906 within a grid 912 maintain a high level of correlation with other cohorts 906 within the enclave 904, cohorts 906 that are no longer within the grid 912 no longer maintain a high level of correlation.

In the illustrated example, the spontaneous ecosystem 900 is an autonomous vehicle environment. In such an environment, vehicles may traverse the roadways of an area (e.g., an entire city, state, or the like). At times, there may be hundreds of thousands of cars traversing the roadways and at other times there may be less vehicles. Each vehicle may be configured to report its sensor data (e.g., LIDAR, radar, video, moisture, etc.) to a cloud-based system, such that the cloud based system may maintain state data relating to the roadways (e.g., where there are vehicles, obstacles, traffic, or the like). The cloud-based system may be configured to report relevant state data to each vehicle, so as to inform the vehicle of conditions along a route of the vehicle (or other suitable data, such as instructions to particular vehicles). Because each vehicle is traveling along its own route and the amount of data collected every second from the collection of vehicles may be vast. In the illustrated example, the VDAX 902 and the AI portal facilitate the reporting of relevant state data to vehicles along the grid using VBLS. In this example, the VDAX 902 may generate a grid corresponding to an area (e.g., a city, a county a state, or the like), where the grid 912 has cells. The cells may be fixed in size or may be dynamically sized depending on the amount of traffic on the roadways. Similarly, the cells may be fixed in number or may be dynamically allocated depending on the amount of traffic on the roadways. In some embodiments, the AI portal determines the number of cells and/or the sizes of the cells in response to the conditions of the roadways (e.g., how many vehicles are on the roadways, how many vehicles are traditionally on the roadways at this time, etc.). In embodiments, each cell is considered an enclave 904 and the cloud-based system may report relevant state data to those vehicles within an enclave 904. In some embodiments, communication towers (e.g., 5G towers) may host the enclave VDAXs that communicate with cohorts 906 within an enclave 904. As a vehicle traverses the roadways, the vehicle may exit one cell and enter another. Furthermore, as a vehicle is likely to go straight, right, or left, the VDAX 902 may assign the vehicle to multiple cells (i.e., enclaves), such that a vehicle may receive relevant state data of one or more cells directly ahead of the vehicle, one or more cells to the right of the vehicle, and one or more cells to the left of the vehicle. The VDAX 902 may provide a vehicle with genomic information for each of these enclaves (e.g., one or more cells to the right, left, and ahead of the vehicle). For each cell/enclave, the vehicle (e.g., a cohort VDAX executing thereon) may generate a GEC and exchange GEC with the cloud-based system to authenticate itself for the particular cell. Once authenticated, the vehicle and the cloud-based system may exchange links to engage with respect to each cell. As the vehicle collects sensor data, the vehicle may generate VBLS based on the collected sensor data, its XNA, and the information contained in the link received from the cloud-based system. Similarly, the cloud-based system may, for each cell, broadcast VBLS that is generated in a VBLS that is specific to the cell (e.g., understood by any cohort that is assigned to the enclave). As a vehicle exits a cell, the VDAX may modify the genetic information of the vehicle for that cell, so that the vehicle will no longer be able to understand VBLS that corresponds to that cell or to generate VBLS that corresponds to that cell.

Application Ecosystems continue to evolve featuring complex services and processes which require richer resource availability and low latency networks. This is evidenced in part by the redistribution of processes and reallocation of infrastructure. Applications generally require sophisticated OS. OS services are increasingly bifurcated, where those having lesser complexity and resource requirements are locally hosted (e.g., Client OS) and those having greater complexity and resource requirements are remotely hosted (e.g., Cloud OS). This efficient OS bifurcation has other profound advantages: proliferation of very low-cost client devices that retain access to powerful non-resident capabilities, exceedingly lower cost bandwidth budgets, and free form distribution and development of powerful new applications. These decidedly new and beneficial applications, like their predecessors, will impose significantly more complex challenges to access and propriety control.

Figure 10:
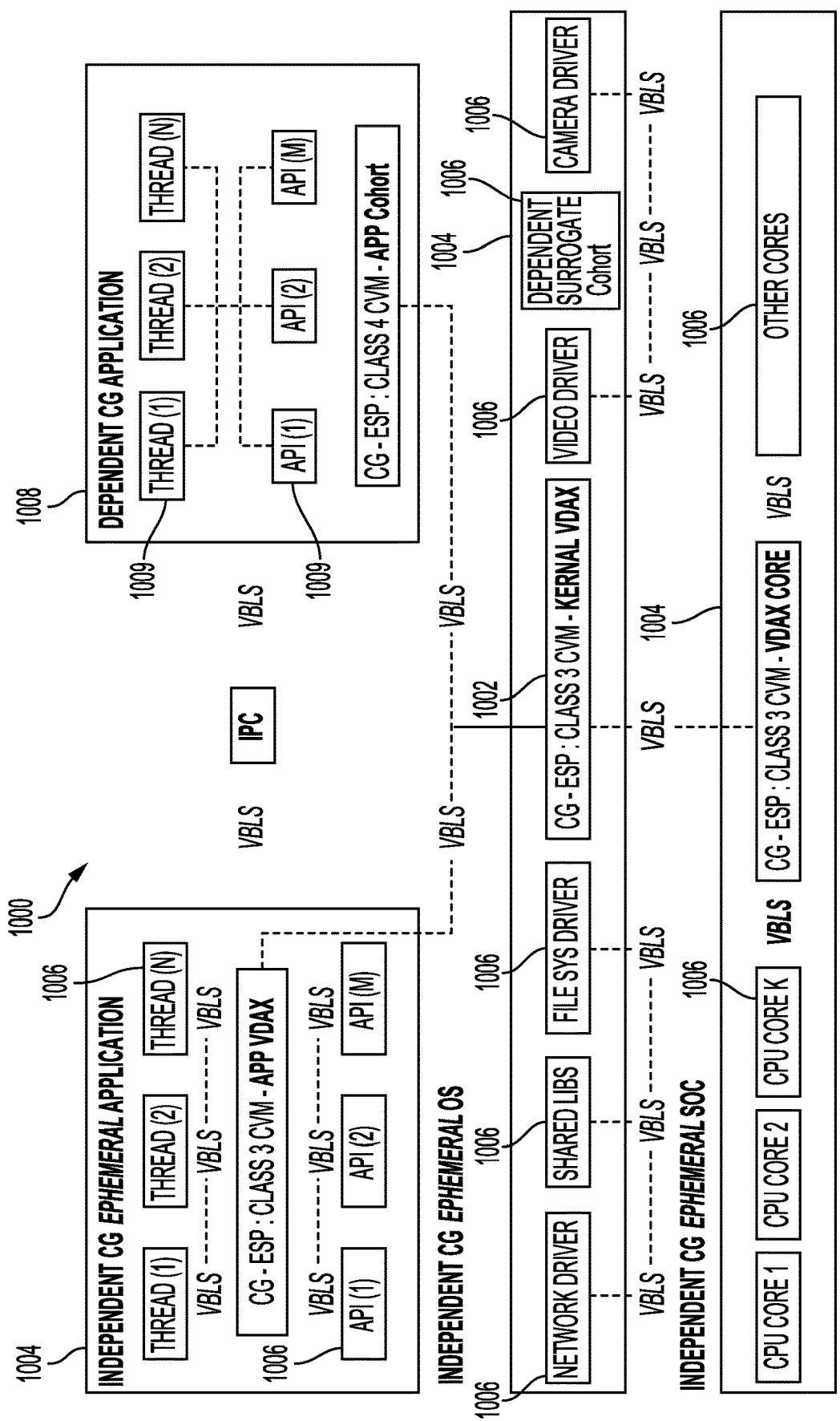
FIG. 10 illustrates an example implementation of a security platform instance that is configured in accordance with an ephemeral architecture in support of a virtual trusted execution domain, in accordance with some embodiments of the present disclosure.

Referring now to FIG. 10, by implementing computationally complex genomic constructions, CG-ESPs enable methods for uniquely transforming engagement between different software and hardware components, "Executable Ecosystems", e.g.: applications (API, libraries, and threads), operating system (kernel, services, drivers, and libraries), and System on a Chip (processing units, e.g., core). These Ecosystem components may prosecute Executable Binaries collaboratively or independently. In embodiments, the methods may enable specific designation and organization of such ecosystems and enclaves, and cohorts (independent cohorts and dependent cohorts)—which best attend their capabilities, limitations, and performance efficiencies —to form a gnomically constructed ephemeral architectures. In embodiments, ephemeral architectures are capable of transforming executable binaries to VBLS digital objects and resultant VBLS streams, which exhibit unique genomic differentiation and correlation. In some of these embodiments, CG-ESPs in ephemeral architectures are capable of computationally complex genomic construction facilitated engagement with other CG-enabled architectures, such as directed (static ecosystems and free-form ecosystems) and spontaneous (dynamic state).

In embodiments, ephemeral architectures may provide many benefits, in that many of their attributes exhibit direct correlation with other architectures (e.g., Directed, and Spontaneous). Ephemeral architectures, however, constitute a very different attack surface in that their components are generally closely coupled and the processes are highly observable and modifiable prior-to and in-process. Thus virtual variety of such conditions may benefit from VBLS facilitated dynamic virtual trusted execution domains.

In embodiments, genomic correlation and differentiation enable ephemeral architectures, which may be genomically configured by VDAX to enable Executable Ecosystems (e.g., ecosystem VDAX, enclave VDAXs, cohort VDAXs, and dependent VDAXs). In further embodiments, and ephemeral architecture based provides for an executable ecosystem where a VDAX of different hierarchical levels provides deep knowledge of source allowing for establishment of trusted components. In a further embodiment, a complex ecosystem such as an autonomous vehicle, or spaceship or mobile phone, or webs services architecture, consisting of a vast array of components that are each made of further subcomponents, in this example each layer of ecosystem allows for their respective VDAX and genomic constructions to build a system of knowledge of source of components. In further embodiments, each component can execute operations to validate the source and veracity of operation of the sub-components. In this example, the veracity of operation may be undertaken by genomic construction enabled exchanges with trusted provisioning sources.

In embodiments, genomically constructed application-specific executable ecosystems do not require modification of their underlying architectural embodiments. In further embodiments, the underlying architecture remains unaltered and executable ecosystems exist as an information overlay that can provide knowledge of source. In further embodiments, the knowledge of the source of the components of the ephemeral architecture may be applied to verify the operational parameters of the executable ecosystem.

In embodiments, an executable ecosystem VDAX may independently initiate unique genomic correlation constructions. In further embodiments, the correlation constructions may provide for verification of attribution of subcomponents within the Enclave VDAX. In some embodiments, the correlation constructions may include—LNA (genomic correlation), CNA (genomic engagement-integrity), and/or PNA (genomic engagement-eligibility. In this example, these constructions may enable virtual authentication.

In embodiments, an executable ecosystem VDAX may independently initiate unique genomic differentiation constructions (e.g., ZNA). In some of these embodiments, the executable ecosystem-initiated differentiation constructions may be applied to determine what components are responsible for specific operations within the ecosystem and/or the determination that the component is isolated. In some embodiments, the differentiation constructions may include ZNA (genomic code-isolation). In this example, these differentiations may enable virtual affiliation.

In embodiments, executable ecosystem VDAXs may acquire their unique genomic correlation constructions directly. In further embodiments, the correlation constructions may provide for verification of attribution of subcomponents within genomic descendent VDAX such as an enclave VDAX or a cohort VDAX. In some embodiments, the correlation constructions may include LNA (genomic correlation), CNA (genomic engagement-integrity), and/or PNA (genomic engagement-eligibility. In this example, these constructions may enable virtual authentication.

In embodiments, executable enclave VDAXs may acquire their unique genomic differentiation constructions directly. In further embodiments, the executable enclave-initiated differentiation constructions may be applied to determine what components are responsible for specific operational or the determination that the component is alone. In some embodiments, the differentiation constructions may include ZNA (genomic code-isolation). In this example, these differentiations may enable virtual affiliation.

In embodiments, executable enclave VDAXs may acquire their unique genomic correlation constructions directly. In further embodiments, the correlation constructions may provide for verification of attribution of subcomponents within genomic decedent VDAX such as a dependent VDAX or a cohort VDAX. In some embodiments, the correlation constructions may include LNA (genomic correlation), CNA (genomic engagement-integrity), and/or PNA (genomic engagement-eligibility. In this example, these constructions may enable virtual authentication.

In embodiments, executable cohort VDAXs may acquire their unique genomic correlation constructions directly. In further embodiments, the correlation constructions may provide for verification of attribution of subcomponents within genomic decedent VDAX such as a dependent VDAX. In some embodiments, the correlation constructions may include LNA (genomic correlation), CNA (genomic engagement-integrity), and/or PNA (genomic engagement-eligibility. In this example, these constructions may enable virtual authentication.

In embodiments, executable cohort VDAX may acquire their unique genomic differentiation constructions directly. In further embodiments, the Executable Enclave initiated differentiation constructions may be applied to determine what components are responsible for specific operational or the determination that the component is isolated. In some of these embodiments, the executable ecosystem initiated differentiation constructions may be applied to determine what components are responsible for specific operations within the ecosystem and/or the determination that the component is isolated. In some embodiments, the differentiation constructions may include ZNA (genomic code-isolation). In this example, these differentiations may enable virtual affiliation.

In embodiments, an executable VDAX (where unrelated VDAX engage) may acquire their unique genomic correlation constructions via alternate genomic sub-constructions. In further embodiments, the correlation constructions may provide for verification of attribution of unrelated components. In some embodiments, the correlation constructions may include—LNA (genomic correlation), CNA (genomic engagement-integrity), and/or PNA (genomic engagement-eligibility. In this example, these constructions may enable virtual authentication.

In embodiments, executable VDAX (where unrelated VDAXs engage) may acquire their unique genomic differentiation constructions via alternate genomic sub-constructions. In further embodiments, the Executable Enclave initiated differentiation constructions may be applied to determine what components are responsible for specific operational or the determination that the component is isolated. In some of these embodiments, the executable ecosystem-initiated differentiation constructions may be applied to determine what components are responsible for specific operations within the ecosystem and/or the determination that the component is isolated. In some embodiments, the differentiation constructions may include ZNA (genomic code-isolation). In this example, these differentiations may enable virtual affiliation.

In embodiments, multiple constructed executable genomic topologies may exist simultaneously. In some embodiments, these multiple genomic topologies may provide genomically enabled operations for different architectural functions. In these example embodiments, the different architectural functions may include, verification of source, validation of operation or validation of payment of license fees.

In embodiments, each executable ecosystem has a unique genomic construction by which correlation and differentiation attributes are derived, these attributes control the genomic topology of its enclaves. In some embodiments, each executable enclave may have a unique genomic construction by which correlation and differentiation attributes are derived, whereby these genomic attributes control the genomic topology of its cohorts. In further embodiments, these unique constructions provide for differentiation across species, progeny, and siblings.

In embodiments, ephemeral architectures, having various genomically constructed configurations are capable of transforming binary data into as VBLS based digital objects and or streams. In embodiments, the ephemeral architecture security platform provides virtual agility. In embodiments, VBLS may refer to languages spoken by an enclave or a cohort to another enclave or cohort that may be uniquely understood by the recipient enclave or cohort—that is, languages that are only understandable by the recipient enclave or cohort. In this example, interlopers aiming to include unauthorized cohorts, viruses, and/or malware, cannot produce or decipher VBLS between authorized cohorts.

In embodiments, VBLS transformed binary data may be exchanged and prosecuted by components from two or more different configurations having common genomic correlation and differentiation. In embodiments, the different configurations provide for state information for Executable Ecosystem operational parameters. In further embodiments, these different configurations are each able to operate subject to their state and functional components with knowledge of associated configuration.

In embodiments, ephemeral architectures may have a plurality of genomically constructed configurations, where certain components maybe capable of transforming executable binaries into Virtual Binary Language Script (VBLS) based digital objects and or streams. In further embodiments, executable binaries may be transformed into VBLS digital objects or VBLS streams, this transformation is accomplished by the application of genomically constructed configuration components. In further embodiments, transformation is accomplished by applying genomic sequence mapping and transformations. In embodiments, the sequences, are central to the computational transformation of digital objects into unique non-recurring genomic engagement factors. In examples, sequences may be broadly disparate, sequences may require processing resulting in specific levels of entropy. In embodiments, the sequence mapping may be compatible with a broad range of protocols and formats or may be initiated with objects exhibiting preexisting entropy, where these objects may be transformed by computationally complex genomic processes and functions into objects exhibiting specific levels of entropy.

In embodiments, VBLS transformed executable binaries may be exchanged and prosecuted by components from two or more different configurations having common genomic correlation and differentiation.

In embodiments, within a specific ephemeral architecture, components may transform VBLS executable binaries (e.g., proprietary computer application) such that the transformed executable binary may only be correctly processed by a specific hardware component (e.g., SoC Core), which components share common genomic correlation and differentiation. In further embodiments, the specific hardware is part of a genomic Ecosystem and is able to apply genomic correlation processes to enable processing of the VBLS executable binaries.

In embodiments, an ephemeral architecture VDAX resident component may transform (VBLS) executable binaries (e.g., proprietary computer application) such that the transformed executable binary may only be correctly processed by another Ephemeral Architecture VDAX specific hardware component (e.g., SoC Core), which components share common genomic correlation and differentiation. In further embodiments, another Ephemeral Architecture VDAX may be part of the genomic ecosystem.

In embodiments, within a specific ephemeral architecture, two or more components may transform executable binaries (e.g., proprietary computer application) based on unique genomic constructions, which constructions are known to another component. These transformed binaries may only be reformed as executable binaries by one of these components and no others. The reformation and prosecution of the executable binaries occur in-place. In embodiments, the components are part of the same genomic ecosystem or genomic enclave.

In embodiments, within a specific ephemeral architecture, specific components may transform executable binaries (e.g., proprietary computer application) based on unique genomic constructions, which constructions are known to specific components of another ephemeral architecture. Transformed binaries originating in one architecture may only be reformed as executable binaries by specific components of the other architecture. The reformation and prosecution of the executable binaries occur in-place. In further embodiments, the ephemeral architectures sharing components are part of the same genomic ecosystem or genomic enclave. In further embodiments, the components that are sharing transformed executable binaries conduct a genomic link exchange to provide for knowledge of the source of components. In further embodiments, the knowledge of source of components is used with further genomic constructions to establish a trust relationship between components.

In embodiments, within a specific ephemeral architecture, a component VDAX may transform executable binaries (e.g., proprietary computer application) based on specific unique genomic constructions, which constructions are known only to that component. Such transformed binaries may only be reformed as executable binaries by this specific component and no other. The reformation and prosecution of the executable binaries by this specific component occurs in-place. In embodiments, these component specific transformations apply genomic constructions based on genomic data known only the component VDAX associated. In further embodiments, the transformed components can operate in a secure way where non component applied alterations to the transformed binaries will render the transformed executable binaries inoperable.

FIG. 10 illustrates an example of a security platform having an ephemeral architecture that serves an executable ecosystem 1000. As discussed, an executable ecosystem 100 may be any ecosystem that is self-contained, such as a computing device (e.g., a server, a mobile device, a personal computer, a laptop computer, or the like). In embodiments, an ephemeral architecture provides a framework for cohorts 1006 to create and decipher VBLS based isolations of executable code instances, thereby providing a real-time virtual trusted executing domain that is not subject to intelligent external observation. For example, in a computing device, enclaves 1004 may include the system-on-chip (SoC) of the computing device, the operating system of the device, and applications. In this example, ecosystem, the independent cohorts 1006 of the system-on-chip enclave may include processor cores, memory devices (e.g., RAM, ROM), and the like. The independent cohorts 1006 of the operating system enclave may include a kernel of the operating system, various drivers (network drivers, file system driver, print driver, video driver, camera driver, dependent "surrogate" cohort, and the like), shared libraries, and the like. In the example, the dependent cohorts 1008 of an application may include threads, APIs, files, and the like. In some embodiments, each enclave (SoC, operating system, application) may be assigned a genomic data set (e.g., ZNA, LNA, CNA, and/or PNA), which is inherited by the cohorts of each respective enclave. In embodiments, an ecosystem VDAX may create an ephemeral enclave when an application is accessed, whereby the ephemeral enclave is created for the cohorts of the application, the cohorts of the operating system that are implicated by the application, and the cohorts of the SoC that are called by the operating system in executing the application. In this example, the cohorts within the ephemeral enclave can authenticate one another, exchange links, and generate VBLS. At execution time, certain threads of an application may request resources from the kernel of the operating system. When a certain thread is executed, an independent cohort VDAX representing the application thread generates VBLS based on the executable code of the certain thread that requests the resource of the kernel. In this scenario, the application thread may be authenticated by an independent cohort VDAX representing the kernel (e.g., a kernel VDAX) using an ecosystem genomic progeny data that was generated using the ecosystem CNA assigned to the thread application (and vice-versa). In response, the kernel VDAX and a thread VDAX representing the thread exchange links that were generated using the respective LNA of the kernel and the application thread. The thread VDAX may then generate VBLS based on the executable code instance(s) requesting the resource, the ZNA assigned to the application thread, and the link provided by the kernel VDAX. The thread VDAX provides the VBLS to the kernel VDAX, which in turn deciphers the VBLS. The kernel VDAX may then interface with a VDAX corresponding to the requested resource (e.g., a camera driver to access a camera of the computing device, dependent "surrogate" cohort) using VBLS that is only decipherable by the kernel or the requested resource.

In some embodiments, dependent applications (as opposed to independent applications) are not capable of secure VBLS isolation of their internal API and thread components. However, both independent and dependent applications are capable of secure VBLS inter-process communication with each other and with authenticated external resources (e.g., operating system, systems on chip). In these embodiments, ephemeral enclaves enable secure VBLS isolation of the kernel and processing cores, ensuring all digital objects on the system bus may only engage with specific application, operating system, and/or SoC cohorts.

Figure 11:
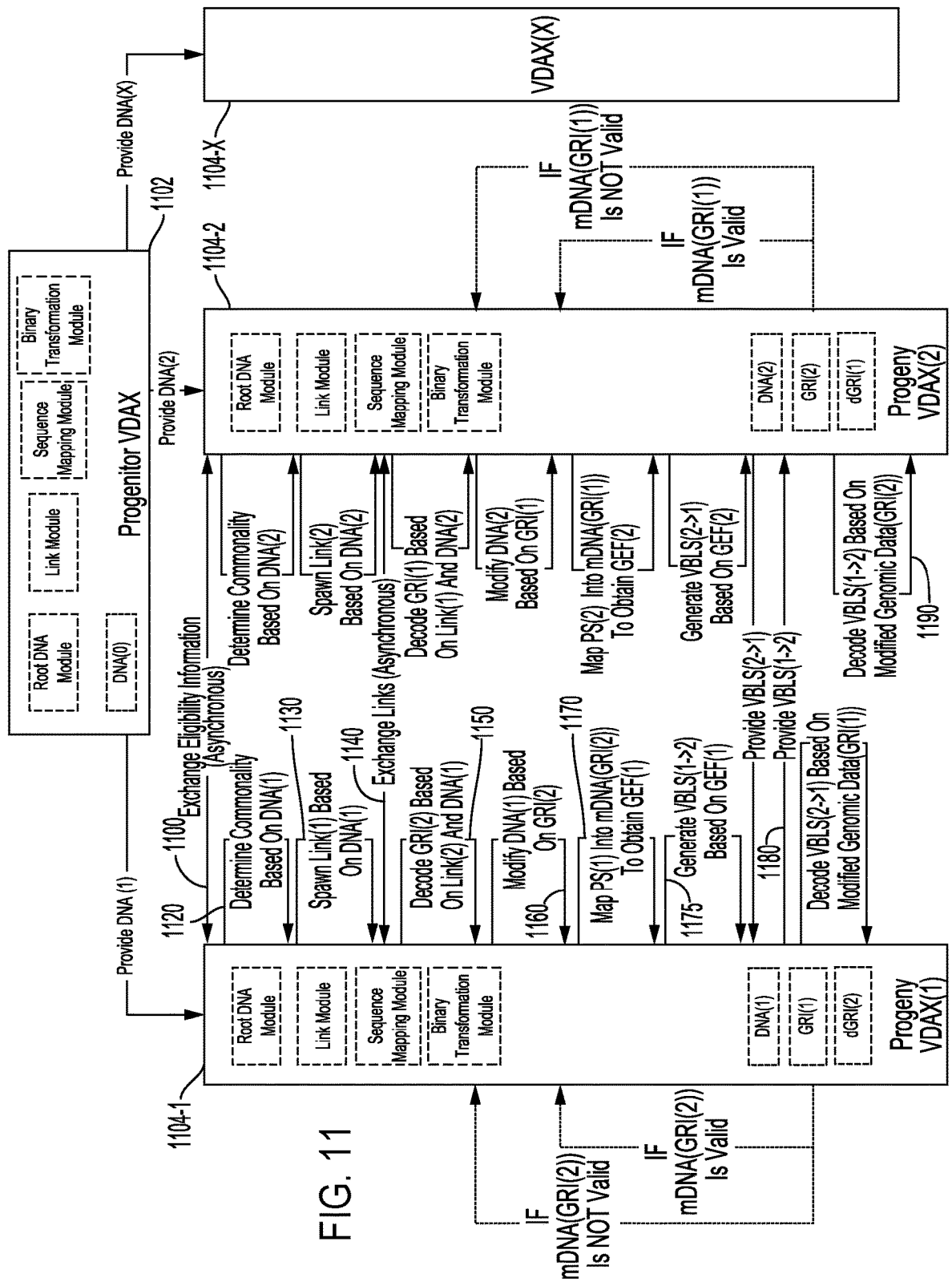
FIG. 11 illustrates example implementations of processes for forming unique non-recurring engagements and exchanging data and securely exchanging data based on the unique non-recurring engagements, in accordance with some embodiments of the present disclosure.

FIG. 11 illustrates an example set of CG-based operations of a process for facilitating VBLS-based data exchange that is executed by a set of members in a CG-enabled ecosystem. The processes, modules, and techniques described with respect to FIG. 11 are provided as example implementations of the CG-based operations that may be performed by VDAXs executing specific configurations of a CG-ESP and are not intended to limit the scope of the disclosure. It is appreciated that the different CG-ESPs may be configured to execute different CG-based operations and may achieve VBLS-based data exchange accordingly.

In the example, a progenitor VDAX 1102 (e.g., an ecosystem VDAX or enclave VDAX) may be configured to add a set of X community members (e.g., independent cohorts) to a community (e.g., an enclave) by digitally generating respective genomic data sets (DNA) for a set of progeny VDAXs 1104-1, 1104-2, . . . 1104-X that respectively correspond to a community member of the X community members, including a first progeny VDAX 1104-1 and a second progeny VDAX 1104-2. In embodiments, the progenitor VDAX 1102 and the progeny VDAXs 1104-1, 1104-2, . . . 1104-X execute respective CG-ESP instances that include a root DNA module, a link module, a sequence mapping module, and a binary transformation module (e.g., as discussed with respect to FIG. 4). It is appreciated that the CG-ESP instances may include additional and/or alternative modules without departing from the scope of the disclosure.

In some embodiments, the root DNA module of the progenitor VDAX 1102 may digitally generate a progenitor genomic data set or may be allocated the progenitor genomic data set from another VDAX. In embodiments, the root DNA module of the progenitor VDAX 1102 digitally generates a respective progeny genomic data set for each progeny VDAX 1104 in a digital community (e.g., ecosystem or enclave) and allocates each respective progeny genomic data set to a respective progeny VDAX 1104. In some of these embodiments, the progenitor VDAX 1102 may digitally generate each progeny genomic data set from a progenitor genomic data set that is assigned to the progenitor VDAX 1102 using a set of information theory-facilitated computationally complex functions.

In embodiments, the genomic data sets of the progenitor VDAX 1102 may include a progenitor genomic eligibility object (e.g., CNA and/or PNA), a progenitor genomic correlation object (e.g., LNA), and/or a progenitor genomic differentiation object (e.g., XNA or ZNA). In some of these embodiments, the progenitor VDAX 1102 may allocate highly correlated (e.g., identical or otherwise sufficiently correlated) genomic correlation and differentiation objects to each of the progeny VDAXs 1104, assuming that the progenitor VDAX 1102 has enabled all of the progeny VDAXs 1104 to communicate (e.g., the progeny VDAXs share a mutual identity of interest). In some embodiments, the progenitor VDAX 1102 may generate unique yet highly correlated genomic eligibility objects using a set of information theory-facilitated computationally complex functions.

In embodiments, the genomic data set of a progeny VDAX 1102 is provided to the progeny VDAX 1102 in the one-time "trusted" event. For example, the progeny genomic data may be provided to a device that executes the progeny VDAX 1102 on a USB stick or other connectable physical media, may be communicated via a wired communication between the progenitor VDAX 1102 and the progeny VDAX 1104 (e.g., via a physical digital communication port of a device that executes the progeny VDAX 1102), via a proximity-based wireless protocol (e.g., near-field communication), when the device that hosts the progeny VDAX 1104 is initially fabricated or configured, via VBLS that is generated and decoded using a different genomic data set, and/or the like. Once a progeny VDAX 1104 is provided with its progeny genomic data set for the particular community, the progeny VDAX 1104 may engage with any other progeny VDAX 1104 in the community via their respective progeny genomic data sets. In the illustrated example, a first progeny VDAX 1104-1 and a second progeny VDAX 1104-2 engage in a set of processes to authenticate each other as community members and facilitate further data exchange, which are discussed below.

At 1110, the first VDAX 1104-1 and second VDAX 1104-2 exchange respective eligibility information. In embodiments, the exchange of eligibility information may be an asynchronous exchange. In some embodiments, eligibility information may be any suitable data that is uniquely associated with a respective community member.

At 1120, a root DNA module of the first VDAX 1104-1 and of the second VDAX 1104-2 each determine a commonality with the other respective VDAX 1104 based on its genomic data and the eligibility information received from the other VDAX 1104 using a set of information theory-facilitated computationally complex functions. As the eligibility information provided by each respective VDAX is unique, the eligibility information provided exchanged by the first VDAX 1104-1 and the second VDAX 1104-2 are asymmetric. Each VDAX 1104, however, may use its own genomic data set (e.g., genomic eligibility object) and the received eligibility information to independently determine the commonality (e.g., an engagement integrity vector) between the pair of VDAX's that reflects a unique correlation between the genomic data sets of the first VDAX 1104-1 and second VDAX 1104-2.

At 1130, a link module of one or both of the VDAXs 1104 spawn a respective link based on its genomic data set and a set of genomic regulation instructions (GRI) that are determined specifically for data exchange with the other VDAX. As discussed, a link may be a mechanism for transporting and decoding GRI, such that each link (e.g., a first link and a second link) is generated by a link spawning VDAXs for the link hosting VDAX to instruct the hosting VDAX on how to generate VBLS that can be decoded by the spawning VDAX. In this way, the links are di-symmetric. In embodiments, the first VDAX 1104-1 may generate a first GRI and may encode the GRI into a first link that is provided to the second VDAX 1104-2. Similarly, the second VDAX 1104-2 may generate a second GRI and may include the second GRI into a second link that is provided to the first VDAX 1104-1. In embodiments, a link includes genomic engagement cargo (GEC) that includes the encoded GRI and information that is used to decode the encoded GRI. In some embodiments, the information that is used to decode the GRI includes an unencoded sequence and encoded instructions that are used to modify the genomic correlation object. In these embodiments, the encoded instructions may be encoded based on the commonality (e.g., as determined at 1120).

In embodiments, a VDAX 1104 generates respective GRI randomly and encodes the generation with a respective link engagement factor. For example, the first VDAX 1104-1 may generate a first GRI and may encode the first GRI using a link engagement factor using a set of information theory-facilitated computationally complex functions. Additionally or alternatively, the second VDAX 1104-2 may generate a second GRI and may encode the second GRI using a second link engagement factor using a set of information theory-facilitated computationally complex functions. In embodiments, a VDAX 1104 generates GRI randomly (e.g., randomly generated values) or in other suitable manners. In embodiments, a VDAX 1104 generates a link engagement factor by determining modification instructions (e.g., randomly) and then modifies its genomic correlation object based on the modification instructions using a set of information theory-facilitated computationally complex functions to obtain a modified genomic correlation object (e.g., modified LNA). In embodiments, the VDAX 1104 may then generate a sequence (e.g., a public sequence, private sequence, or any other suitable sequence) and may map the sequence into the modified genomic correlation object using a set of information theory-facilitated computationally complex functions to obtain the link engagement factor. The VDAX 1104 may then encode the GRI using the determined link engagement factor using a set of information theory-facilitated computationally complex functions to obtain the encoded GRI. In embodiments, the VDAX 1104 may also encode the modification instructions using the commonality (e.g., as determined at 1120) and may generate GEC that includes the encoded GRI, the encoded modification instructions, and the sequence used to generate the link engagement factor (where the sequence is left unencoded).

In some embodiments, the first VDAX 1104-1 may encode the GRI using a first link engagement factor and a set of information theory-facilitated computationally complex functions. In some At 1140, the first VDAX 1104-1 and the second VDAX 1104-2 exchange links. In embodiments, the link exchange is performed asynchronously. Assuming both VDAXs generated a respective link, each VDAX 1104-1, 1104-2 may provide the generated link to the other respective VDAX. For example, the first VDAX 1104-1 may provide a first link containing a first GEC to the second VDAX 1104-2, and/or the second VDAX 1104-2 may provide a second link containing a second GEC to the first VDAX 1104-1. In embodiments, a link may include additional information (e.g., metadata indicating a source of a link, application-specific metadata, and/or the like) in addition to the genomic engagement cargo. The VDAXs may exchange links in any suitable manner. For example, links may be communicated over a communication network and/or a data bus. Alternatively, links may be communicated via a physical storage medium (e.g., a USB memory drive, a CD, a DVD, or the like) or via a proximity-based protocol (e.g., NFC or Bluetooth).

At 1150, a link module of each VDAX 1104 that receives a link from the other VDAX 1104 decodes the encoded GRI included in the received link. For example, the second VDAX 1104-2 may receive the first link from the first VDAX 1104-1 and may decode the first genomic instructions from the link. In example embodiments, the second VDAX 1104-2 may initially decode the encoded modification based on the commonality (e.g., the engagement integrity vector) with the first VDAX 1104-2 using a set of information theory-facilitated computationally complex functions. The second VDAX 1104-2 may then modify its genomic data (e.g., its genomic correlation object) based on the decoded modification instructions to obtain modified genomic data (e.g., a modified genomic correlation object). Assuming that both VDAXs are of the same community, the second VDAX 1104-2 will be able to modify its genomic data (e.g., genomic correlation object) in the same manner by which the first VDAX 1104-1 modified its genomic data, such that the modified genomic data (e.g., modified correlation object) is sufficient correlated. The second VDAX 1104-1 may then map the sequence contained in the first GEC into the modified genomic data (e.g., into the modified correlation object) to obtain the first link engagement factor. The second VDAX 1104-2 may then decode the first encoded GRI using the first link engagement factor to obtain first decoded GRI (dGRI). The first GRI may then be stored on behalf of the first VDAX 1104-1 for future engagement with the first VDAX 1104-1, such that the second VDAX 1104-2 is said to host the first link. Similarly, the first VDAX 1104-1 may decode the second link based on the contents of the second GEC to obtain the second decoded GRI and may store the second decoded GRI on behalf of the second VDAX 1104-2. It is noted that the decoding of links requires that the VDAXs 1104 have highly correlated (e.g., identical or otherwise sufficiently correlated) genomic data and have functionally identical configurations. If any of these conditions are not met, the VDAXs 1104 will be unable to successfully decode the respective links. In embodiments, the link hosting VDAX may also confirm/authenticate the other VDAX based on the link by executing a set of predefined operations to verify that the spawning link has highly correlated genomic data and a functionally identical configuration (e.g., thereby authenticating the spawning VDAX as an engageable cohort)

Operations 1160-1190 describe operations that may be performed to generate VBLS after the first and second VDAX have exchanged links. For purposes of explanation, operations 1160-1190 describe a scenario where the first VDAX 1104-1 sends VBLS to the second VDAX 1104-2 and the second VDAX 1104-2 decodes the VBLS.

At 1160, the root DNA module of the first VDAX 1104-1 may modify its genomic data (e.g., genomic differentiation object) based on the second GRI provided by the second VDAX 1104-2 using a set of information theory-facilitated computationally complex functions to obtain modified genomic data. In some embodiments, the first VDAX 1104-1 modifies its XNA or ZNA based on the second GRI to obtain modified XNA or modified ZNA.

At 1170, a sequence mapping module of the first VDAX 1104-1 may map a sequence (e.g., a public sequence or a private sequence) into its modified genomic data set (resulting from the modification using the second genomic regulation instructions received from the second VDAX 1104-2) to obtain a first VBLS genomic engagement factor. In some embodiments, the first VDAX 1104-1 may obtain the sequence from a first portion of a digital object that is to be provided to the second VDAX 1102-2. For example, if the digital object is a data packet, the first portion of the data packet may include protocol specific information that is used to transmit the data packet (e.g., TCP header, UDP header, or other suitable protocol data). In embodiments, the first VDAX 1104-1 may then map the sequence into the modified genomic data (e.g., modified XNA) using a set of information theory-facilitated computationally complex functions to obtain a genomic engagement factor.

At 1175, the first VDAX 1104-1 may generate a VBLS object for the second VDAX 1104-2 based on the digital object and the genomic engagement factor. In embodiments, the binary transformation module of the first VDAX 1104-1 may encode a second portion of the digital object using the genomic engagement factor and a set of information theory-facilitated computationally complex functions. In embodiments, the second portion of the digital object may be encoded by disambiguation where the second portion of the digital object is XOR'd with the genomic engagement factor to obtain an encoded digital object. Alternatively, the binary transformation module of the first VDAX 1104-1 may encrypt the second portion of the digital object using the genomic engagement factor and an encryption function to obtain an encoded digital object.

At 1180, the first VDAX 1104-1 may provide VBLS object to the second VDAX 1104-2. In embodiments, the VBLS object may include the encoded digital object, metadata that is to be used by the first VDAX 1104-1 to decode the encoded digital object, and any other suitable data (e.g., protocol data). For example, in some embodiments, the VBLS object may include the first portion of the digital object (which includes the extracted sequence and other suitable protocol data) and the encoded digital object.

At 1190, the second VDAX 1104-2 decodes the VBLS provided by the first VDAX 1104-1 based on its own genomic data set, the second GRI (which were provided to and decoded by the first VDAX 1104-1), and the metadata contained in respective VBLS objects. In some implementations, the root DNA module of the second VDAX 1104-2 may modify its genomic data (e.g., genomic differentiation object) using the second GRI and a set of information theory-facilitated computationally complex functions to obtain modified genomic data (e.g., modified genomic differentiation object). The sequence mapping module of the second VDAX 1104-2 may then extract the sequence from the VBLS object (e.g., from a first portion of the VBLS object) and may map the sequence into the modified genomic data (e.g., modified genomic differentiation object) to obtain a genomic engagement factor using a set of information theory-facilitated computationally complex functions. The binary transformation module of the second VDAX 1104-2 may then decode the encoded digital object based on the genomic engagement factor and a set of information theory-facilitated computationally complex functions. For example, the second VDAX 1104-2 may disambiguate the encoded digital object or decrypt the encoded digital object using the genomic engagement factor to obtain a decoded digital object.

In some example implementations, a VBLS object may include verification data that is provided by the sending VDAX (e.g., first VDAX 1104-1) to the receiving VDAX (e.g., second VDAX 1104-2), such that the verification data is a value that is used to determine the genomic engagement factor that was used to encode the VBLS object. In these implementations, the receiving VDAX may, after decoding the VBLS object, may recalculate the verification data using the same set of information theory-facilitated computationally complex functions. If the recalculated verification data matches the verification data contained in the VBLS object, the receiving VDAX may confirm that the VBLS object was properly decoded and/or that the VBLS object was not tampered with by a third party.

The VDAXs 1104 may continue to exchange VBLS in this manner. In embodiments, the sending VDAX 1104 may generate a new genomic engagement factor for each digital object, such that each digital object is encoded using a unique non-recurring genomic engagement factor. Thus, the sending VDAX 1104 may iterate between blocks 1170 and 1180 and the recipient VDAX may decode the VBLS. It is noted that between data exchanges, the sending VDAX may have to modify its genomic data if the modified genomic data is no longer valid (e.g., is no longer cached or in memory). In this scenario, the sending VDAX may repeat block 1160 as well. Furthermore, as sequence mapping techniques can be applied to any suitable protocol or format, the sets described herein can be applied at various levels of a protocol stack (e.g., networking stack, application stack, or software stack), thereby providing virtual agility.

It is also noted that blocks 1110-1150 only need to be performed once between a pair of sufficiently related VDAXs 1104 (e.g., a pair of cohorts in an enclave). Once the links have been exchanged, the pair of VDAXs 1104 can continue to exchange VBLS even if their respective genomic data sets are modified (e.g., by the progenitor VDAX 1102). If one of the community members to which a VDAX 1104 corresponds is "revoked" from the community, its genomic data the genomic data sets of the other community members can be updated, such that the genomic data set of the revoked community member is no longer sufficiently correlated with the non-revoked community member because of the asymmetric updates to the genomic data sets. In this way, the pair of VDAXs 1104 will no longer be able to modify their genomic data sets in the same manner, even though both VDAXs 1104 still host valid links. Conversely, even if the progenitor VDAX 1102 updates the genomic data sets of both VDAXs in the same manner, the pair of VDAXs 1104 may still generate VBLS using the same links, as the GRI will result in the same modifications being made to the respective updated genomic data sets. As such, link exchange may be referred to as a "one-time process," even though a pair of cohorts may later exchange new links. Furthermore, in some implementations, the pair of VDAXs 1104 may update their links periodically. It is noted, however, that such updates to the links do not require performance of the process at 1140 and 1150; rather, the pair of VDAXs 1104 may encode updated genomic regulation instructions in respective VBLS objects and may decode the updated genomic regulation instructions.

It is further noted that the implementations discussed in FIG. 11 are non-limiting example implementations of a CG-ESP. For instance, genomic data assignment, authentication, and link exchange between two VDAXs 1104 may be performed in other suitable manners, provided that the VDAXs 1104 are able to sufficiently differentiate their sufficiently correlated genomic data sets from other sufficiently correlated VDAXs 1104 via secretly held genomic regulation instructions. Furthermore, in some example implementations, the secretly held genomic regulation instructions may be non-expiring and/or may be selectively updated. In this way, regardless of the manner of initial genomic data assignment, VDAX authentication, or VDAX link exchange, a community owner may selectively opt to configure a CG-ESP to allow one-time authentication and/or link exchange. In these implementations, a pair of sufficiently correlated VDAXs 1104 may be allowed to continue to securely exchange data for as long as they have a genomic data set that is sufficiently correlated and sufficiently differentiable. This type of flexibility allows a community owner to configure a CG-ESP having diverse architectures and configurations to serve diverse ecosystem and community types.

Figure 12:
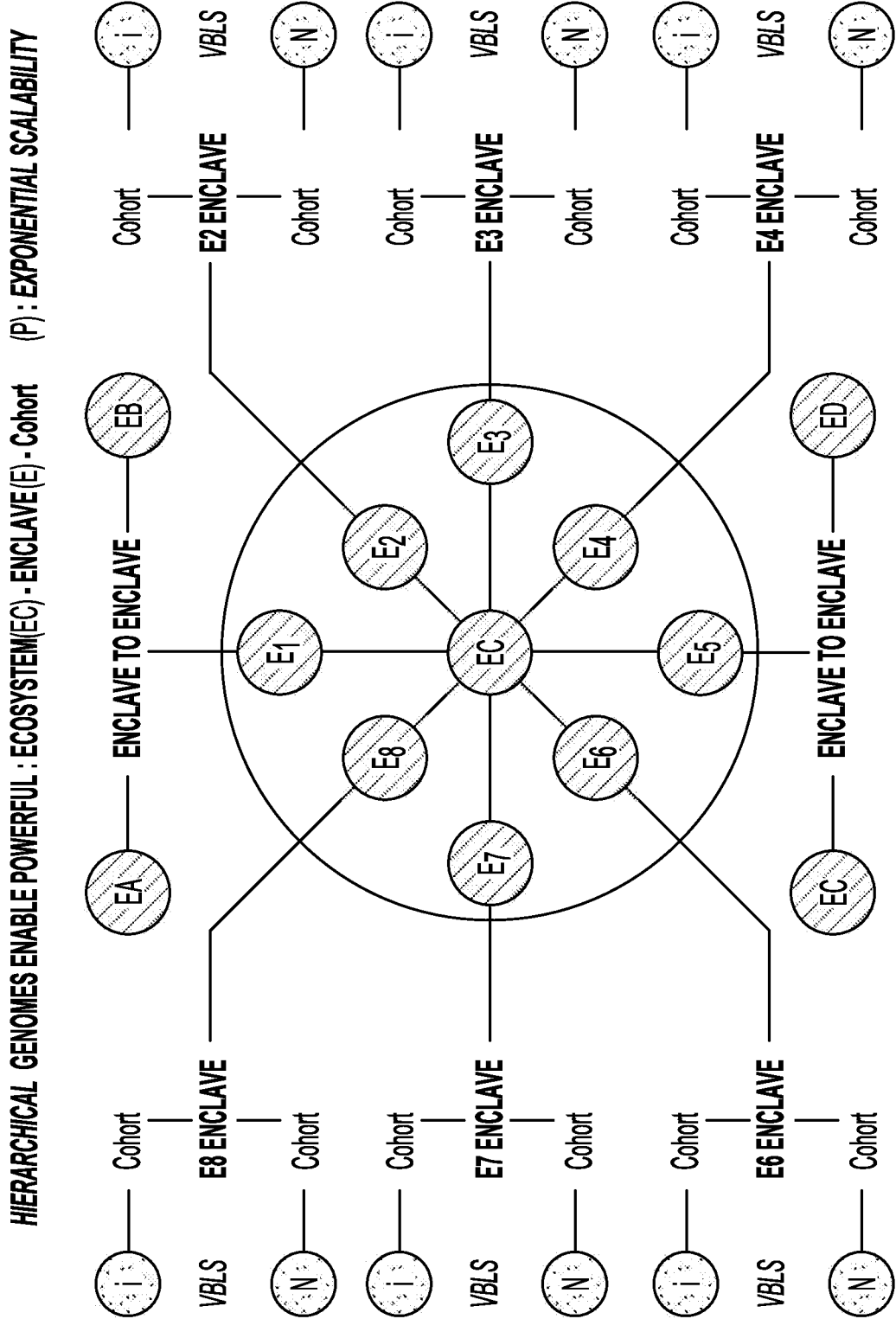
FIGS. 12 and 13 illustrate examples of different CG-enabled digital ecosystems that may be formed in accordance with some embodiments of the present disclosure.
Figure 13:
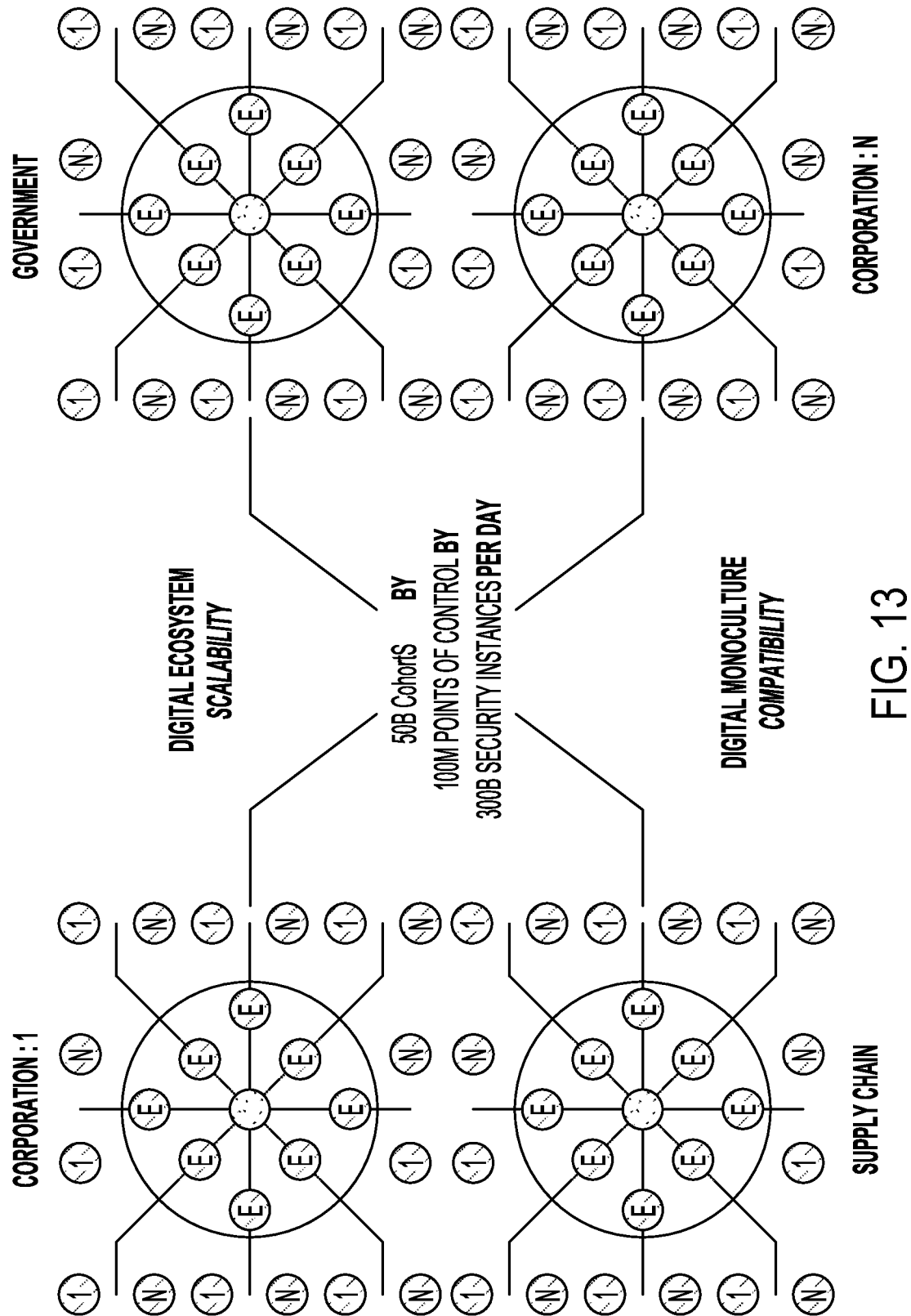

FIGS. 12 and 13 illustrate additional non-limiting examples of CG-enabled digital ecosystems that may be implemented using the teachings of the disclosure. As can be appreciated multiple genomic network topologies may be implemented at various levels of these digital ecosystems.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other type of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The methods and systems described herein may be deployed in part or in whole through a machine that executes computer software on a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM, and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

The methods and systems described herein may transform physical and/or intangible items from one state to another.

The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable code using a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions. Computer software may employ virtualization, virtual machines, containers, dock facilities, portainers, and other capabilities.

Thus, in one aspect, methods described above and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "with," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure, and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference as if fully set forth herein.

What is claimed is:

1. A system for performing genomic security-related control of a digital ecosystem, comprising:
   an ecosystem computing device associated with an owner of the digital ecosystem, the ecosystem computing device having one or more processors and being configured with an ecosystem instance of an ecosystem security platform, wherein the computing device is configured to:

maintain a progenitor genomic data set corresponding to the digital ecosystem that includes one or more different digitally generated progenitor genomic data objects, wherein each progenitor genomic data object exhibits a respective specific entropy;

generate a plurality of respective progeny genomic data sets based on the progenitor genomic data set, wherein each respective progeny genomic data set includes one or more different progeny genomic data objects that were respectively derived from the one or more digitally generated progenitor genomic data objects and exhibit the respective specific entropy of the progenitor genomic data object from which it was derived;

for each progeny genomic data set:
  allocate the progeny genomic data set to a respective progeny Virtual Digital Anonymity Exchange Controller ("VDAX") of a plurality of progeny VDAXs, wherein the respective progeny VDAX establishes unique non-recurring engagements with other progeny VDAXs in the digital ecosystem based on the progeny genomic data set allocated to the respective progeny VDAX without any further interaction from the ecosystem VDAX; and
  control a genomic topology of the digital ecosystem by selectively updating one or more of the progeny genomic data sets to affect an ability of specific progeny VDAXs to engage with other VDAXs in the digital ecosystem.

2. The system of claim 1, wherein the progenitor genomic data set includes a progenitor genomic differentiation object and each progeny genomic data set includes a respective progeny genomic differentiation object.

3. The system of claim 2, wherein a pair of progeny VDAXs from the plurality of progeny VDAXs can exchange virtual binary language script (VBLS) only if the respective progeny genomic differentiation objects of the pair of progeny VDAXs are sufficiently correlated.

4. The system of claim 3, wherein the pair of progeny VDAXs are prevented from future exchange of VBLS when a first progeny genomic differentiation object of a first progeny VDAX of the pair of progeny VDAXs is updated and a second progeny genomic differentiation object of a second progeny VDAX of the pair of progeny VDAXs is not updated.

5. The system of claim 3, wherein the progenitor genomic differentiation and the respective progeny genomic differentiation objects are XNA objects.

6. The system of claim 5, wherein the digital ecosystem is at least one of:
  a static ecosystem, wherein the ecosystem platform is configured in accordance with a directed architecture;
  an interactive ecosystem, wherein the ecosystem platform is configured in accordance with a free form architecture; or
  a dynamic ecosystem, wherein the ecosystem platform is configured in accordance with a dynamic-state spontaneous architecture.

7. The system of claim 6 wherein the plurality of progeny VDAXs include a set of one or more enclave VDAXs, wherein each enclave VDAX corresponds to a respective digital enclave of the digital ecosystem and is allocated a respective enclave-specific XNA object with which the enclave VDAX controls an enclave genomic topology of the respective enclave.

8. The system of claim 7, wherein each respective digital enclave includes one or more additional progeny VDAXs that respectively represent one or more respective cohorts that are admitted to the digital enclave, wherein each respective progeny VDAX that is included in the respective digital enclave is allocated a progeny enclave-specific XNA object that is derived from the enclave-specific XNA object of the enclave VDAX and is sufficiently correlated with respective progeny enclave XNA objects of other progeny VDAXs that are included in the digital enclave.

9. The system of claim 8, wherein a respective enclave VDAX controls membership to the corresponding respective digital enclave by allocating enclave-specific XNA objects to the cohorts of the digital enclave.

10. The system of claim 8, wherein each enclave VDAX is further allocated a respective enclave genomic correlation object that is derived from a progenitor correlation object of the progenitor genomic data set.

11. The system of claim 10, wherein for each digital enclave, each progeny VDAX in the digital enclave is allocated a respective progeny enclave-specific genomic correlation object that is derived from the enclave from the respective enclave genomic correlation object of the enclave VDAX of the digital enclave.

12. The system of claim 11, wherein each progeny VDAX is allocated the respective enclave-specific genomic correlation object directly from the enclave VDAX of the digital enclave.

13. The system of claim 11, wherein each progeny VDAX is allocated the respective enclave-specific genomic correlation object directly from the ecosystem computing device.

14. The system of claim 11, wherein each progeny VDAXs uses its respective progeny enclave-specific genomic correlation object to spawn links that respectively establish unique non-recurring engagements with other progeny VDAXs that are formed with respect to the respective digital enclave.

15. The system of claim 14, wherein each spawned link by the progeny VDAX provides unique genomic regulation instructions that define a manner by which a link hosting progeny VDAX modifies its enclave-specific XNA object to generate non-recurring VBLS that only the progeny VDAX can decode.

16. The system of claim 11, wherein each progeny VDAXs uses its respective progeny enclave-specific genomic correlation object to host links provided by other progeny VDAXs in the digital ecosystem, wherein the other progeny VDAXs provide the links to the progeny VDAX to establish unique non-recurring engagements with the progeny VDAX with respect to the respective digital enclave.

17. The system of claim 16, wherein each hosted link by the progeny VDAX provides unique genomic regulation instructions that define a manner by which the progeny VDAX modifies its enclave-specific genomic differentiation object to generate non-recurring VBLS that only the other progeny VDAX that provided the link can decode.

18. The system of claim 17, wherein the enclave VDAX controls the genomic network topology by selectively updating progeny enclave-specific genomic data objects of a subset of progeny VDAXs that participate in the digital enclave.

19. The system of claim 17, wherein the enclave VDAX controls the genomic network topology of the digital enclave without requiring modification to a physical network topology of the digital enclave.

20. The system of claim 6, wherein the digital ecosystem includes multiple genomic topologies that overlay one or more physical network topologies, wherein the multiple genomic topologies exist simultaneously and interoperably.

21. The system of claim 6, wherein the ecosystem VDAX computing device constructs and controls a genomic network topology that supports applications having dynamic state attributes.

22. The system of claim 21 wherein the plurality of progeny VDAXs includes a set of one or more enclave VDAXs, wherein each enclave VDAX corresponds to a respective digital enclave of the digital ecosystem and is allocated a respective enclave-specific genomic data set with which the enclave VDAX controls portions of the genomic network topology that are responsible for ecosystem-designated functions and processes of the digital ecosystem.

23. The system of claim 22, further comprising a set of cohort VDAXs that participate in the digital ecosystem, wherein the set of cohort VDAXs include one or more cohorts that respectively control respective sub-portions of the genomic network topology that are responsible for specific ecosystem-designated functions and process or enclave-designated functions and processes.

24. The system of claim 23, wherein interaction by the set of cohort VDAXs is controlled by respective cohort genomic data sets allocated to respective cohort VDAXs of the set of cohort VDAXs.

25. The system of claim 24, wherein the plurality of progeny VDAXs include the set of cohort VDAXs.

26. The system of claim 24, wherein the cohort genomic data set of each cohort of the set of cohort VDAXs includes:

one or more cohort genomic eligibility objects that include one or both of one unique CNA object and one unique PNA object;

one or more cohort genomic correlation objects that include one or more LNA objects, wherein each LNA object corresponds to a respective enclave to which the cohort VDAX is admitted; and one or more cohort genomic differentiation objects that include one or more XNA objects, wherein each XNA object corresponds to a respective enclave to which the cohort VDAX is admitted.

27. The system of claim 21, wherein the digital ecosystem is a dynamic ecosystem and the ecosystem security platform is configured in accordance with a spontaneous architecture that retains its operational integrity regardless a frequency in which one or more metric states of the dynamic ecosystem is updated.

28. The system of claim 27, wherein the ecosystem VDAX computing device and the progeny VDAXs collectively control the genomic network topology in response to specific dynamic metric states.

29. The system of claim 27, supports multiple genomic network topologies overlaid on a physical network topology that exist simultaneously.

30. The system of claim 27, wherein the genomic digital network topology is constructed to realize controlled levels of interoperability.

\* \* \* \* \*